US007378426B2

(12) United States Patent
Gavai et al.

(10) Patent No.: US 7,378,426 B2
(45) Date of Patent: May 27, 2008

(54) FUSED HETEROTRICYCLIC COMPOUNDS AS INHIBITORS OF 17β-HYDROXYSTEROID DEHYDROGENASE 3

(75) Inventors: Ashvinikumar V. Gavai, Princeton Junction, NJ (US); Derek J. Norris, Pennington, NJ (US); Wen-Ching Han, Newtown, PA (US); Gregory D. Vite, Titusville, NJ (US); Brian E. Fink, West Windsor, NJ (US); John S. Tokarski, Princeton, NJ (US)

(73) Assignee: Bristol-Myers Squibb Company, Princeton, NJ (US)

( * ) Notice: Subject to any disclaimer, the term of this patent is extended or adjusted under 35 U.S.C. 154(b) by 343 days.

(21) Appl. No.: 11/066,407

(22) Filed: Feb. 25, 2005

(65) Prior Publication Data

US 2005/0192310 A1    Sep. 1, 2005

Related U.S. Application Data

(60) Provisional application No. 60/549,045, filed on Mar. 1, 2004.

(51) Int. Cl.
| A01N 43/42 | (2006.01) |
| A61K 31/44 | (2006.01) |
| C07D 487/00 | (2006.01) |
| C07D 491/00 | (2006.01) |
| C07D 513/00 | (2006.01) |

(52) U.S. Cl. .................................. 514/291; 540/476
(58) Field of Classification Search .................. None
See application file for complete search history.

(56) References Cited

U.S. PATENT DOCUMENTS

| 3,336,293 | A | 8/1967 | Cusic et al. |
| 5,514,505 | A | 5/1996 | Limburg et al. |
| 2004/0176324 | A1 | 9/2004 | Salvati et al. |
| 2005/0191707 | A1 | 9/2005 | Lorenzi et al. |
| 2005/0250753 | A1 | 11/2005 | Fink et al. |

FOREIGN PATENT DOCUMENTS

| JP | 06234753 | 8/1994 |
| JP | 2001-247573 | 9/2001 |
| WO | WO 9509858 | 4/1995 |

OTHER PUBLICATIONS

King, et. al.; 2001; Encyclopedia of Reagents for Organic Synthesis; Palladium on Carbon; p. 1-12.*
Scovill et. al.; 1980; Journal of Heterocyclic Chemistry; 17, 23, p. 23-27.*
Schindler, et. al., Helvetica Chimica Acta (1966), 49(2), 985-9.*
Gheiler, E. L., et al., Current concepts in androgen deprivation therapy—is there a "best" endocrine treatment?, World J. Urology., vol. 18, pp. 190-193, (2000).
Kambe, et al., "Intramolecular 1,3-Dipolar Cycloaddition Strategy for Enantioselective Synthesis of FR-900482 Analogues", Organic Letters, vol. 3(16), pp. 2575-2578, (2001).
Cooper et al., Cyclic Amidines. Part IV. 5:6:22:23-Tetrahydro-5:11-endomethylenephenhomazines and Tröger's Base, Journal of the Chemical Society, Abstracts, pp. 991-994, (1955).
PCT International Search Report (PCT/US05/06548) mailed Dec. 7, 2005.
PCT International Search Report (PCT/US05/06549) mailed Dec. 13, 2005.
U.S. Appl. No. 11/255,484, filed Oct. 21, 2005, Kick, et al.

* cited by examiner

*Primary Examiner*—Jeffrey H Murray
(74) *Attorney, Agent, or Firm*—Gary D. Greenblatt

(57) ABSTRACT

Disclosed are fused heterotricyclic compounds of the following formula I, (I)

$$m(R_6) - \boxed{A} \begin{array}{c} O \diagdown \diagup R_9 \\ N - \\ \end{array} \boxed{C} - (R_{10})n$$
$$X_1 = X_2$$

or an enantiomer, diastereomer, tautomer or pharmaceutically acceptable salt thereof, wherein one of A ring or C ring is a 5-7 membered unsaturated heterocyclic ring. The disclosed compounds are useful as inhibitors of 17β-hydroxysteroid dehydrogenase 3 (17β-HSD3). Also disclosed are methods of using such compounds in the treatment of hormone sensitive diseases such as prostate cancer, and pharmaceutical compositions comprising such compounds.

30 Claims, No Drawings

FUSED HETEROTRICYCLIC COMPOUNDS AS INHIBITORS OF 17β-HYDROXYSTEROID DEHYDROGENASE 3

RELATED APPLICATION

This application claims priority benefit under Title 35 § 119(e) of U.S. provisional Application No. 60/549,045, filed on Mar. 1, 2004, the contents of which are herein incorporated by reference.

FIELD OF THE INVENTION

The present invention relates to fused heterotricyclic compounds, to methods of using such compounds in the treatment of hormone sensitive diseases such as prostate cancer, and to pharmaceutical compositions containing such compounds.

BACKGROUND OF THE INVENTION

17β-hydroxysteroid dehydrogenase 3 (17β-HSD3) is an essential enzyme in the biosynthesis of testosterone. It catalyzes the reduction of androstenedione, a weakly active androgen produced by the adrenal glands, to testosterone. Inano et al., *Steroids*, 48, 1-26, (1986) and Luu-The et al., *J. Steroid Biochem. Mol. Biol.*, 55, 581-587 (1995). 17β-HSD3 is expressed predominately in the adult testes and to a lesser extent in seminal vesicles and prostate tissue, an expression pattern consistent with an enzyme involved in both gonadal and peripheral target tissue androgen biosynthesis. 17β-HSD3 is responsible for the synthesis of about 60% of all active androgens in men. Labrie, *Mol. Cell. Endocrinol.* 78, C113-C118 (1991). The development and progression of hormone sensitive diseases, e.g., prostate cancer, is stimulated by androgens such as testosterone. Inhibition of 17β-HSD3 therefore provides a novel means to disrupt testosterone biosynthesis for the treatment of androgen-associated diseases. Van Weerden et al., *J. Steroid Biochem. Mol. Biol.*, 20, 903-907 (1990) and Liu et al., *J. Clin. Endocrinol.*, 77, 1472-1478 (1993).

Current pharmacological treatments to prevent androgen action in androgen-associated diseases such as prostate cancer are centered on the combined use of luteinizing hormone releasing hormone (LHRH) analogues with androgen receptor antagonists ("anti-androgens"). Labrie et al., *Endocr.-Relat. Cancer*, 3, 243-278 (1996); Gheiler et al., *World J. Urol.*, 18, 190-193 (2000); and Simard, et al., *J. Urol.*, 49, 580-586 (1997). LHRH analogues interfere with central nervous system feedback mechanisms to suppress testosterone biosynthesis in the testes to produce chemical castration. However, it is estimated that up to 50% of testosterone levels remain within prostate tissue following chemical or surgical castration indicating the existence of alternate routes of testosterone biosynthesis independent of the testes. Anti-androgens are used to block the action of this remaining testosterone in prostate cancer cells by antagonizing hormone function at the level of receptor binding. Although the combined use of LHRH analogues with anti-androgens has shown success in the management of prostate cancer, these responses are largely restricted to advanced metastatic disease. Further, patients receiving these treatments ultimately become refractory and progress to a more aggressive, hormone-independent state for which there is no effective therapy.

Inhibitors of 17β-HSD3 have been described in the art. See, e.g., Pittaway, *Contraception*, 27, 431 (1983); Labrie et al., WO99/46279; Maltais et al., *J. Med. Chem.*, 45, 640-653 (2002); and Guzi et al., WO03/022835. There remains a need for potent, selective inhibitors of 17β-HSD3 with improved pharmacological properties, physical properties and side effect profiles.

The compounds of the present invention are inhibitors of 17β-HSD3, and therefore have therapeutic use as anti-cancer agents, as well as other therapeutic agents, for example, as anti-fertility agents as described following.

SUMMARY OF THE INVENTION

The present invention provides a fused heterotricyclic compound of the following formula I, or an enantiomer, diastereomer, tautomer or pharmaceutically acceptable salt or solvate thereof, which compounds are especially useful as inhibitors of 17β-hydroxysteroid dehydrogenase 3 (17β-HSD3):

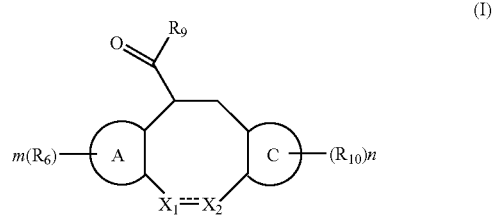

(I)

As used in formula I, and throughout the specification, the symbols have the following meanings unless otherwise indicated, and are, for each occurrence, independently selected:

$x_1$ ---- $x_2$ is —CR$_1$=CR$_3$—, —CR$_1$R$_2$—CR$_3$R$_4$—, —C(=O)—CR$_3$R$_4$—, —S—CR$_3$R$_4$—, —S(=O)—CR$_3$R$_4$—, —S(=O)$_2$—CR$_3$R$_4$—, —O—CR$_3$R$_4$—, —NR$_5$—CR$_3$R$_4$—, —CR$_1$R$_2$—S—, —CR$_1$R$_2$—S(=O)—, —CR$_1$R$_2$—S(=O)$_2$—, —CR$_1$R$_2$—C(=O)—, —CR$_1$R$_2$—O—, or —CR$_1$R$_2$—NR$_5$—;

A ring and C ring are each independently 5-7 membered unsaturated carbocyclic ring or 5-7 membered unsaturated heterocyclic ring, provided that at least one of said A ring and C ring is 5-7 membered unsaturated heterocyclic ring;

R$_2$, R$_4$, R$_6$ and R$_{10}$ are each independently hydrogen, halogen, cyano, nitro, alkyl or substituted alkyl (including CF$_3$), alkenyl or substituted alkenyl, alkynyl or substituted alkynyl, cycloalkyl or substituted cycloalkyl, cycloalkenyl or substituted cycloalkenyl, heterocycle or substituted heterocycle, aryl or substituted aryl, OR$_a$, SR$_a$, S(=O)R$_e$, S(=O)$_2$R$_e$, P(=O)$_2$R$_e$, S(=O)$_2$OR$_e$, P(=O)$_2$OR$_e$, NR$_b$R$_c$, NR$_b$S(=O)$_2$R$_e$, NR$_b$P(=O)$_2$R$_e$, S(=O)$_2$NR$_b$R$_c$, P(=O)$_2$NR$_b$R$_c$, C(=O)OR$_e$, C(=O)R$_a$, C(=O)NR$_b$R$_c$, OC(=O)R$_a$, OC(=O)NR$_b$R$_c$, NR$_b$C(=O)OR$_e$, NR$_d$C(=O)NR$_b$R$_c$, NR$_d$S(=O)$_2$NR$_b$R$_c$, NR$_d$P(=O)$_2$NR$_b$R$_c$, NR$_b$C(=O)R$_a$, or NR$_b$P(=O)$_2$R$_e$, wherein: R$_2$ and R$_4$ together may optionally form a 3-7 membered optionally substituted carbocyclic ring or 3-7 membered optionally substituted heterocyclic ring;

R$_a$ is hydrogen, alkyl or substituted alkyl, alkenyl or substituted alkenyl, alkynyl or substituted alkynyl, cycloalkyl or substituted cycloalkyl, cycloalkenyl or substituted cycloalkenyl, heterocycle or substituted heterocycle, or aryl or substituted aryl;

R$_b$, R$_c$ and R$_d$ are independently hydrogen, alkyl or substituted alkyl, cycloalkyl or substituted cycloalkyl, heterocycle or substituted heterocycle, or aryl or substituted aryl, or said $R_b$ and $R_e$ together with the N to which they are bonded optionally form a heterocycle or substituted heterocycle;

$R_e$ is alkyl or substituted alkyl, alkenyl or substituted alkenyl, alkynyl or substituted alkynyl, cycloalkyl or substituted cycloalkyl, cycloalkenyl or substituted cycloalkenyl, heterocycle or substituted heterocycle, or aryl or substituted aryl;

$R_1$ and $R_3$ are each independently hydrogen, cyano, nitro, alkyl or substituted alkyl, alkenyl or substituted alkenyl, alkynyl or substituted alkynyl, cycloalkyl or substituted cycloalkyl, heterocycle or substituted heterocycle, aryl or substituted aryl, $OR_a$, $SR_a$, $S(=O)R_e$, $S(=O)_2R_e$, $C(=O)OR_e$, $C(=O)R_a$, $NR_bR_c$, $NR_bC(=O)R_a$, $NR_bC(=O)OR_e$, $C(=O)NR_bR_c$, $OC(=O)R_a$, or $OC(=O)NR_bR_c$, wherein $R_1$ and $R_3$ together may optionally form a 3-7 membered optionally substituted carbocyclic ring or 3-7 membered optionally substituted heterocyclic ring;

$R_5$ is hydrogen, alkyl or substituted alkyl, cycloalkyl or substituted cycloalkyl, heterocycle or substituted heterocycle, aryl or substituted aryl, $OR_a$, $S(=O)_2R_e$, $C(=O)OR_e$, $C(=O)R_a$, or $C(=O)NR_bR_c$;

$R_9$ is H, alkyl or substituted alkyl (including $CF_3$), cycloalkyl or substituted cycloalkyl, cycloalkenyl or substituted cycloalkenyl, heterocycle or substituted heterocycle, aryl or substituted aryl, $OR_e$, or $NR_bR_c$;

m is 1-4; and n is 1-4;

provided that:

when $x_1$‑‑‑‑‑$x_2$ is $—CH_2—CH_2—$ and when C ring is thiophene, at least one of $R_6$ and $R_{10}$ is not H.

FURTHER DESCRIPTION OF THE INVENTION

The following are definitions of terms used in the present specification. The initial definition provided for a group or term herein applies to that group or term throughout the present specification individually or as part of another group, unless otherwise indicated.

The terms "alkyl" and "alk" refers to a straight or branched chain alkane (hydrocarbon) radical containing from 1 to 12 carbon atoms, preferably 1 to 6 carbon atoms. Exemplary "alkyl" groups include methyl, ethyl, propyl, isopropyl, n-butyl, t-butyl, isobutyl pentyl, hexyl, isohexyl, heptyl, 4,4-dimethylpentyl, octyl, 2,2,4-trimethylpentyl, nonyl, decyl, undecyl, dodecyl, and the like. The term "$C_1$-$C_4$ alkyl" refers to a straight or branched chain alkane (hydrocarbon) radical containing from 1 to 4 carbon atoms, such as methyl, ethyl, propyl, isopropyl, n-butyl, t-butyl, and isobutyl. "Substituted alkyl" refers to an alkyl group substituted with one or more substituents, preferably 1 to 4 substituents, at any available point of attachment. Exemplary substituents include but are not limited to one or more of the following groups: hydrogen, halogen (e.g., a single halogen substituent or multiple halo substitutents forming, in the latter case, groups such as $CF_3$ or an alkyl group bearing $Cl_3$), cyano, nitro, cycloalkyl, alkenyl, cycloalkenyl, alkynyl, heterocycle, aryl, $OR_a$, $SR_a$, $S(=O)R_e$, $S(=O)_2R_e$, $P(=O)_2R_e$, $S(=O)_2OR_e$, $P(=O)_2OR_e$, $NR_bR_c$, $NR_bS(=O)_2R_e$, $NR_bP(=O)_2R_e$, $S(=O)_2NR_bR_c$, $P(=O)_2NR_bR_c$, $C(=O)OR_e$, $C(=O)R_a$, $C(=O)NR_bR_c$, $OC(=O)R_a$, $OC(=O)NR_bR_c$, $NR_bC(=O)OR_e$, $NR_dC(=O)NR_bR_c$, $NR_dS(=O)_2NR_bR_c$, $NR_dP(=O)_2NR_bR_c$, $NR_bC(=O)R_a$, or $NR_bP(=O)_2R_e$, wherein $R_a$ is hydrogen, alkyl, cycloalkyl, alkenyl, cycloalkenyl, alkynyl, heterocycle, or aryl; $R_b$, $R_e$ and $R_d$ are independently hydrogen, alkyl, cycloalkyl, heterocycle, aryl, or said $R_b$ and $R_c$ together with the N to which they are bonded optionally form a heterocycle; and $R_e$ is alkyl, cycloalkyl, alkenyl, cycloalkenyl, alkynyl, heterocycle, or aryl. In the aforementioned exemplary substitutents, groups such as alkyl, cycloalkyl, alkenyl, alkynyl, cycloalkenyl, heterocycle and aryl can themselves be optionally substituted.

The term "alkenyl" refers to a straight or branched chain hydrocarbon radical containing from 2 to 12 carbon atoms and at least one carbon-carbon double bond. Exemplary such groups include ethenyl or allyl. "Substituted alkenyl" refers to an alkenyl group substituted with one or more substituents, preferably 1 to 4 substituents, at any available point of attachment. Exemplary substituents include, but are not limited to, alkyl or substituted alkyl, as well as those groups recited above as exemplary alkyl substituents.

The term "alkynyl" refers to a straight or branched chain hydrocarbon radical containing from 2 to 12 carbon atoms and at least one carbon to carbon triple bond. Exemplary such groups include ethynyl. "Substituted alkynyl" refers to an alkynyl group substituted with one or more substituents, preferably 1 to 4 substituents, at any available point of attachment. Exemplary substituents include, but are not limited to, alkyl or substituted alkyl, as well as those groups recited above as exemplary alkyl substituents.

The term "cycloalkyl" refers to a fully saturated cyclic hydrocarbon group containing from 1 to 4 rings and 3 to 8 carbons per ring. Exemplary such groups include cyclopropyl, cyclobutyl, cyclopentyl, cyclohexyl, cycloheptyl, etc. "Substituted cycloalkyl" refers to a cycloalkyl group substituted with one or more substituents, preferably 1 to 4 substituents, at any available point of attachment. Exemplary substituents include, but are not limited to, nitro, cyano, alkyl or substituted alkyl, as well as those groups recited above as exemplary alkyl substituents. Exemplary substituents also include spiro-attached or fused cylic substituents, especially spiro-attached cycloalkyl, spiro-attached cycloalkenyl, spiro-attached heterocycle (excluding heteroaryl), fused cycloalkyl, fused cycloalkenyl, fused heterocycle, or fused aryl, where the aforementioned cycloalkyl, cycloalkenyl, heterocycle and aryl substitutents can themselves be optionally substituted.

The term "cycloalkenyl" refers to a partially unsaturated cyclic hydrocarbon group containing 1 to 4 rings and 3 to 8 carbons per ring. Exemplary such groups include cyclobutenyl, cyclopentenyl, cyclohexenyl, etc. "Substituted cycloalkenyl" refers to a cycloalkenyl group substituted with one more substituents, preferably 1 to 4 substituents, at any available point of attachment. Exemplary substituents include but are not limited to nitro, cyano, alkyl or substituted alkyl, as well as those groups recited above as exemplary alkyl substituents. Exemplary substituents also include spiro-attached or fused cylic substituents, especially spiro-attached cycloalkyl, spiro-attached cycloalkenyl, spiro-attached heterocycle (excluding heteroaryl), fused cycloalkyl, fused cycloalkenyl, fused heterocycle, or fused aryl, where the aforementioned cycloalkyl, cycloalkenyl, heterocycle and aryl substituents can themselves be optionally substituted.

The term "aryl" refers to cyclic, aromatic hydrocarbon groups that have 1 to 5 aromatic rings, especially monocyclic or bicyclic groups such as phenyl, biphenyl or naphthyl. Where containing two or more aromatic rings (bicyclic, etc.), the aromatic rings of the aryl group may be joined at a single point (e.g., biphenyl), or fused (e.g., naphthyl, phenanthrenyl and the like). "Substituted aryl" refers to an aryl group substituted by one or more substituents, preferably 1 to 3 substituents, at any point of attachment. Exemplary substituents include, but are not limited to, nitro, cycloalkyl or substituted cycloalkyl, cycloalkenyl or substituted cycloalkenyl, cyano, alkyl or substituted alkyl, as well as those groups recited above as exemplary alkyl substituents. Exemplary substituents also include fused cylic groups, especially fused cycloalkyl, fused cycloalkenyl, fused heterocycle, or fused aryl, where the aforementioned cycloalkyl, cycloalkenyl, heterocycle and aryl substituents can themselves be optionally substituted.

The terms "heterocycle" and "heterocyclic" refer to fully saturated, or partially or fully unsaturated, including aromatic (i.e., "heteroaryl") cyclic groups (for example, 4 to 7 membered monocyclic, 7 to 11 membered bicyclic, or 10 to 16 membered tricyclic ring systems) which have at least one heteroatom in at least one carbon atom-containing ring. Each ring of the heterocyclic group containing a heteroatom may have 1, 2, 3, or 4 heteroatoms selected from nitrogen atoms, oxygen atoms and/or sulfur atoms, where the nitrogen and sulfur heteroatoms may optionally be oxidized and the nitrogen heteroatoms may optionally be quaternized. (The term "heteroarylium" refers to a heteroaryl group bearing a quaternary nitrogen atom and thus a positive charge.) The heterocyclic group may be attached to the remainder of the molecule at any heteroatom or carbon atom of the ring or ring system. Exemplary monocyclic heterocyclic groups include azetidinyl, pyrrolidinyl, pyrrolyl, pyrazolyl, oxetanyl, pyrazolinyl, imidazolyl, imidazolinyl, imidazolidinyl, oxazolyl, oxazolidinyl, isoxazolinyl, isoxazolyl, thiazolyl, thiadiazolyl, thiazolidinyl, isothiazolyl, isothiazolidinyl, furyl, tetrahydrofuryl, thienyl, oxadiazolyl, piperidinyl, piperazinyl, 2-oxopiperazinyl, 2-oxopiperidinyl, 2-oxopyrrolodinyl, 2-oxoazepinyl, azepinyl, hexahydrodiazepinyl, 4-piperidonyl, pyridyl, pyrazinyl, pyrimidinyl, pyridazinyl, triazinyl, triazolyl, tetrazolyl, tetrahydropyranyl, morpholinyl, thiamorpholinyl, thiamorpholinyl sulfoxide, thiamorpholinyl sulfone, 1,3-dioxolane and tetrahydro-1,1-dioxothienyl, and the like. Exemplary bicyclic heterocyclic groups include indolyl, isoindolyl, benzothiazolyl, benzoxazolyl, benzoxadiazolyl, benzothienyl, quinuclidinyl, quinolinyl, tetrahydroisoquinolinyl, isoquinolinyl, benzimidazolyl, benzopyranyl, indolizinyl, benzofuryl, benzofurazanyl, chromonyl, coumarinyl, benzopyranyl, cinnolinyl, quinoxalinyl, indazolyl, pyrrolopyridyl, furopyridinyl (such as furo[2,3-c]pyridinyl, furo[3,2-b]pyridinyl] or furo[2,3-b]pyridinyl), dihydroisoindolyl, dihydroquinazolinyl (such as 3,4-dihydro-4-oxoquinazolinyl), triazinylazepinyl, tetrahydroquinolinyl and the like. Exemplary tricyclic heterocyclic groups include carbazolyl, benzidolyl, phenanthrolinyl, acridinyl, phenanthridinyl, xanthenyl and the like.

"Substituted heterocycle" and "substituted heterocyclic" (such as "substituted heteroaryl") refer to heterocycle or heterocyclic groups substituted with one or more substituents, preferably 1 to 4 substituents, at any available point of attachment. Exemplary substituents include, but are not limited to, cycloalkyl or substituted cycloalkyl, cycloalkenyl or substituted cycloalkenyl, nitro, oxo (i.e., =O), cyano, alkyl or substituted alkyl, as well as those groups recited above as exemplary alkyl substituents. Exemplary substituents also include spiro-attached or fused cylic substituents at any available point or points of attachment, especially spiro-attached cycloalkyl, spiro-attached cycloalkenyl, spiro-attached heterocycle (excluding heteroaryl), fused cycloalkyl, fused cycloalkenyl, fused heterocycle, or fused aryl, where the aforementioned cycloalkyl, cycloalkenyl, heterocycle and aryl substituents can themselves be optionally substituted.

The term "quaternary nitrogen" refers to a tetravalent positively charged nitrogen atom including, for example, the positively charged nitrogen in a tetraalkylammonium group (e.g., tetramethylammonium, N-methylpyridinium), the positively charged nitrogen in protonated ammonium species (e.g., trimethyl-hydroammonium, N-hydropyridinium), the positively charged nitrogen in amine N-oxides (e.g., N-methyl-morpholine-N-oxide, pyridine-N-oxide), and the positively charged nitrogen in an N-amino-ammonium group (e.g., N-aminopyridinium).

The terms "halogen" or "halo" refer to chlorine, bromine, fluorine or iodine.

The term "carbocyclic" refers to aromatic or non-aromatic 3 to 7 membered monocyclic and 7 to 11 membered bicyclic groups, in which all atoms of the ring or rings are carbon atoms. "Substituted carbocyclic" refers to a carbocyclic group substituted with one or more substituents, preferably 1 to 4 substituents, at any available point of attachment. Exemplary substituents include, but are not limited to, nitro, cyano, $OR_a$, wherein $R_a$ is as defined hereinabove, as well as those groups recited above as exemplary cycloalkyl substituents.

When a functional group is termed "protected", this means that the group is in modified form to mitigate, especially preclude, undesired side reactions at the protected site. Suitable protecting groups for the methods and compounds described herein include, without limitation, those described in standard textbooks, such as Greene, T. W. et al., *Protective Groups in Organic Synthesis*, Wiley, N.Y. (1999).

Unless otherwise indicated, any heteroatom with unsatisfied valences is assumed to have hydrogen atoms sufficient to satisfy the valences.

The compounds of formula I form salts which are also within the scope of this invention. Reference to a compound of the formula I herein is understood to include reference to salts thereof, unless otherwise indicated. The term "salt(s)", as employed herein, denotes acidic and/or basic salts formed with inorganic and/or organic acids and bases. In addition, when a compound of formula I contains both a basic moiety, such as but not limited to a pyridine or imidazole, and an acidic moiety such as but not limited to a carboxylic acid, zwitterions ("inner salts") may be formed and are included within the term "salt(s)" as used herein. Pharmaceutically acceptable (i.e., non-toxic, physiologically acceptable) salts are preferred, although other salts are also useful, e.g., in isolation or purification steps which may be employed during preparation. Salts of the compounds of the formula I may be formed, for example, by reacting a compound I with an amount of acid or base, such as an equivalent amount, in a medium such as one in which the salt precipitates or in an aqueous medium followed by lyophilization.

The compounds of formula I which contain a basic moiety, such as but not limited to an amine or a pyridine or imidazole ring, may form salts with a variety of organic and inorganic acids. Exemplary acid addition salts include acetates (such as those formed with acetic acid or trihaloacetic acid, for example, trifluoroacetic acid), adipates, alginates, ascorbates, aspartates, benzoates, benzenesulfonates, bisulfates, borates, butyrates, citrates, camphorates, camphorsulfonates, cyclopentanepropionates, digluconates, dodecylsulfates, ethanesulfonates, fumarates, glucoheptanoates, glycerophosphates, hemisulfates, heptanoates, hexanoates, hydrochlorides, hydrobromides, hydroiodides, hydroxyethanesulfonates (e.g., 2-hydroxyethanesulfonates), lactates, maleates, methanesulfonates, naphthalenesulfonates (e.g., 2-naphthalenesulfonates), nicotinates, nitrates, oxalates, pectinates, persulfates, phenylpropionates (e.g., 3-phenylpropionates), phosphates, picrates, pivalates, propionates, salicylates, succinates, sulfates (such as those formed with sulfuric acid), sulfonates, tartrates, thiocyanates, toluenesulfonates such as tosylates, undecanoates, and the like.

The compounds of formula I which contain an acidic moiety, such but not limited to a carboxylic acid, may form salts with a variety of organic and inorganic bases. Exemplary basic salts include ammonium salts, alkali metal salts such as sodium, lithium and potassium salts, alkaline earth metal salts such as calcium and magnesium salts, salts with organic bases (for example, organic amines) such as benzathines, dicyclohexylamines, hydrabamines (formed with N,N-bis(dehydroabietyl) ethylenediamine), N-methyl-D-glucamines, N-methyl-D-glycamides, t-butyl amines, and salts with amino acids such as arginine, lysine and the like. Basic nitrogen-containing groups may be quaternized with agents such as lower alkyl halides (e.g. methyl, ethyl, propyl, and butyl chlorides, bromides and iodides), dialkyl sulfates (e.g. dimethyl, diethyl, dibutyl, and diamyl sulfates), long chain halides (e.g. decyl, lauryl, myristyl and stearyl chlorides, bromides and iodides), aralkyl halides (e.g. benzyl and phenethyl bromides), and others.

Prodrugs and solvates of the compounds of the invention are also contemplated herein. The term "prodrug" as employed herein denotes a compound that, upon administration to a subject, undergoes chemical conversion by metabolic or chemical processes to yield a compound of the formula I, or a salt and/or solvate thereof. Solvates of the compounds of formula I include, for example, hydrates.

Compounds of the formula I, and salts thereof, may exist in their tautomeric form (for example, as an amide or imino ether). All such tautomeric forms are contemplated herein as part of the present invention.

All stereoisomers of the present compounds (for example, those which may exist due to asymmetric carbons on various substituents), including enantiomeric forms and diastereomeric forms, are contemplated within the scope of this invention. Individual stereoisomers of the compounds of the invention may, for example, be substantially free of other isomers (e.g., as a pure or substantially pure optical isomer having a specified activity), or may be admixed, for example, as racemates or with all other, or other selected, stereoisomers. The chiral centers of the present invention may have the S or R configuration as defined by the IUPAC 1974 Recommendations. The racemic forms can be resolved by physical methods, such as, for example, fractional crystallization, separation or crystallization of diastereomeric derivatives or separation by chiral column chromatography. The individual optical isomers can be obtained from the racemates by any suitable method, including without limitation, conventional methods, such as, for example, salt formation with an optically active acid followed by crystallization.

Compounds of the formula I are, subsequent to their preparation, preferably isolated and purified to obtain a composition containing an amount by weight equal to or greater than 99% formula I compound ("substantially pure" compound I), which is then used or formulated as described herein. Such "substantially pure" compounds of the formula I are also contemplated herein as part of the present invention.

All configurational isomers of the compounds of the present invention are contemplated, either in admixture or in pure or substantially pure form. The definition of compounds of the present invention embraces both cis (Z) and trans (E) alkene isomers, as well as cis and trans isomers of cyclic hydrocarbon or heterocyclic rings.

Throughout the specifications, groups and substituents thereof may be chosen to provide stable moieties and compounds.

METHODS OF PREPARATION

The compounds of the present invention may be prepared by methods such as those illustrated in the following schemes. Solvents, temperatures, pressures, and other reaction conditions may readily be selected by one of ordinary skill in the art. Starting materials are commercially available or readily prepared by one of ordinary skill in the art.

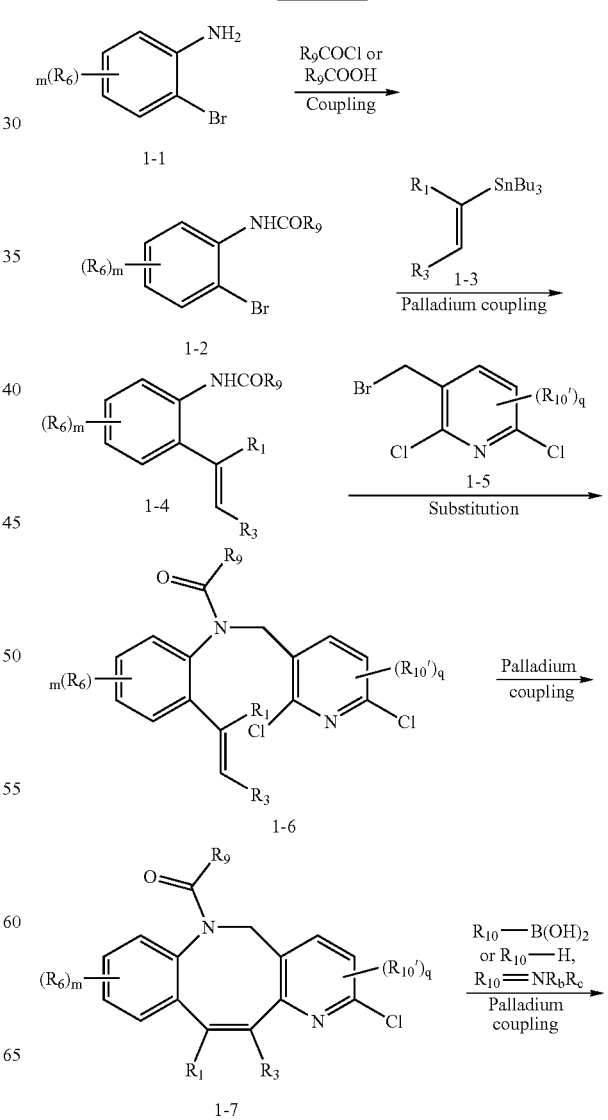

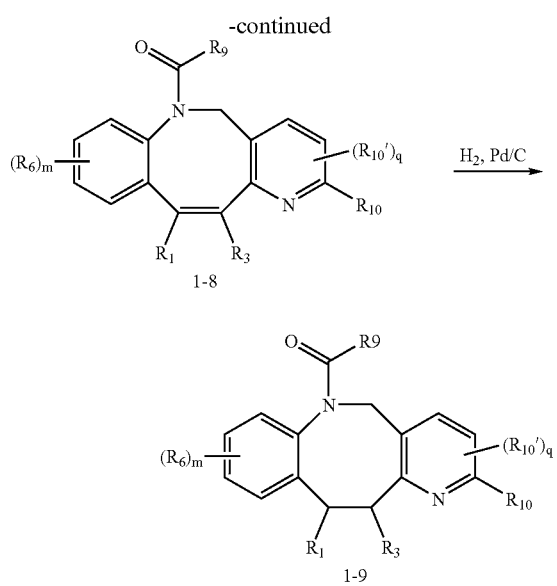

substituted alkyl, alkenyl or substituted alkenyl, alkynyl or substituted alkynyl, cycloalkyl or substituted cycloalkyl, heterocycle or substituted heterocycle, or aryl or substituted aryl. The definition contained herein also applies to Scheme 2 through Scheme 5a and FIG. 1, unless otherwise noticed.

Amide coupling of starting material 1-1 yields intermediate 1-2, which gives compound 1-4 upon treating with tin reagent 1-3. The tin reagent 1-3 is either commercially available or can be prepared by one skilled in the art. Nuclear substitution of intermediate 1-5 using compound 1-4 affords intermediate 1-6, which can be cyclized via a palladium coupling to offer compound 1-7. Reacting compound 1-7 with a borane reagent such as $R_{10}$—$B(OH)_2$, or an amine such as $R_{10}$—H (i.e., $HNR_bR_c$, when $R_{10}$ is —$NR_bR_c$), in a palladium coupling condition, generates compound 1-8, which can be converted to compound 1-9 through hydrogenation.

Intermediate 1-5 can be prepared according to Scheme 1a. Reduction of starting material 1-10 yields compound 1-11, which can be converted into bromo-substituted intermediate 1-5 via bromination.

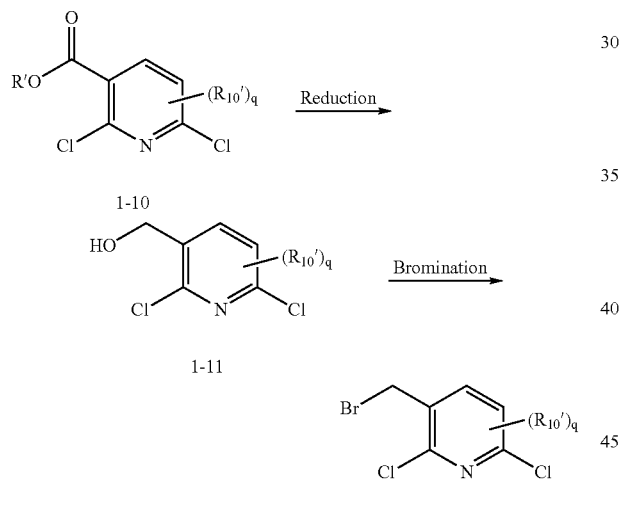

As illustrated in Schemes 1 and 1a, compounds of formula I can be made from 1-1; $R_1$, $R_3$, $R_6$, $R_9$, $R_b$, $R_c$ and m are defined as above ($R_6$ is preferably not Br); $R_{10}'$ is hydrogen, hagogen (perferably F and Cl), cyano, nitro, alkyl or substituted alkyl, alkenyl or substituted alkenyl, alkynyl or substituted alkynyl, cycloalkyl or substituted cycloalkyl, cycloalkenyl or substituted cycloalkenyl, heterocycle or substituted heterocycle, aryl or substituted aryl, $OR_a$, $SR_a$, $S(=O)R_e$, $S(=O)_2R_e$, $P(=O)_2R_e$, $S(=O)_2OR_e$, $P(=O)_2OR_e$, $NR_bR_c$, $NR_bS(=O)_2R_e$, $NR_bP(=O)_2R_e$, $S(=O)_2NR_bR_c$, $P(=O)_2NR_bR_c$, $C(=O)OR_e$, $C(=O)R_a$, $C(=O)NR_bR_c$, $OC(=O)R_a$, $OC(=O)NR_bR_c$, $NR_bC(=O)OR_e$, $NR_dC(=O)NR_bR_c$, $NR_dS(=O)_2NR_bR_c$, $NR_dP(=O)_2NR_bR_c$, $NR_bC(=O)R_a$, or $NR_bP(=O)_2R_e$, wherein $R_a$, $R_b$, $R_c$, $R_d$ and $R_e$ are as defined above; q=1-2; and $R_{10}$ is alkyl or

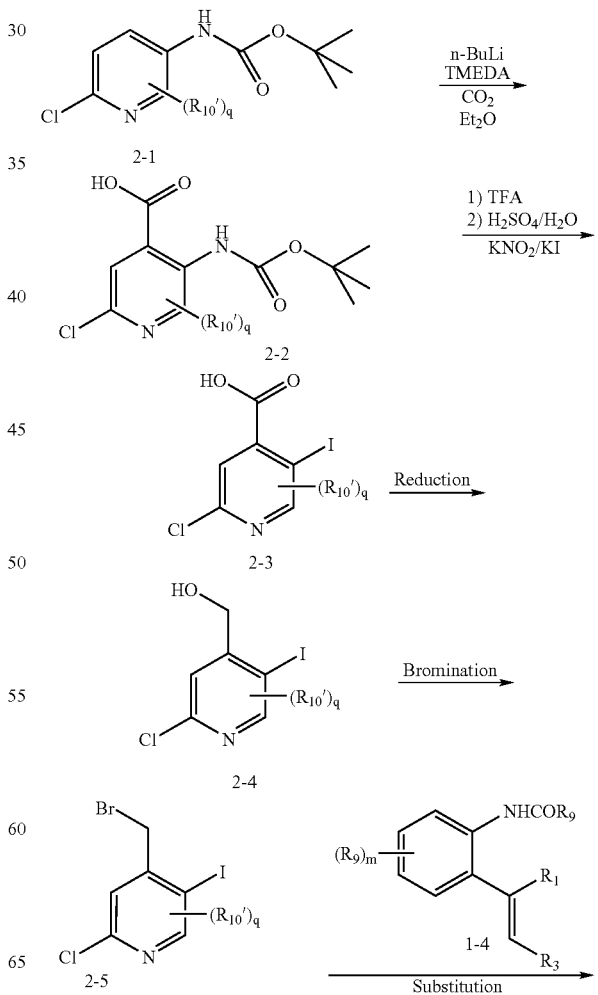

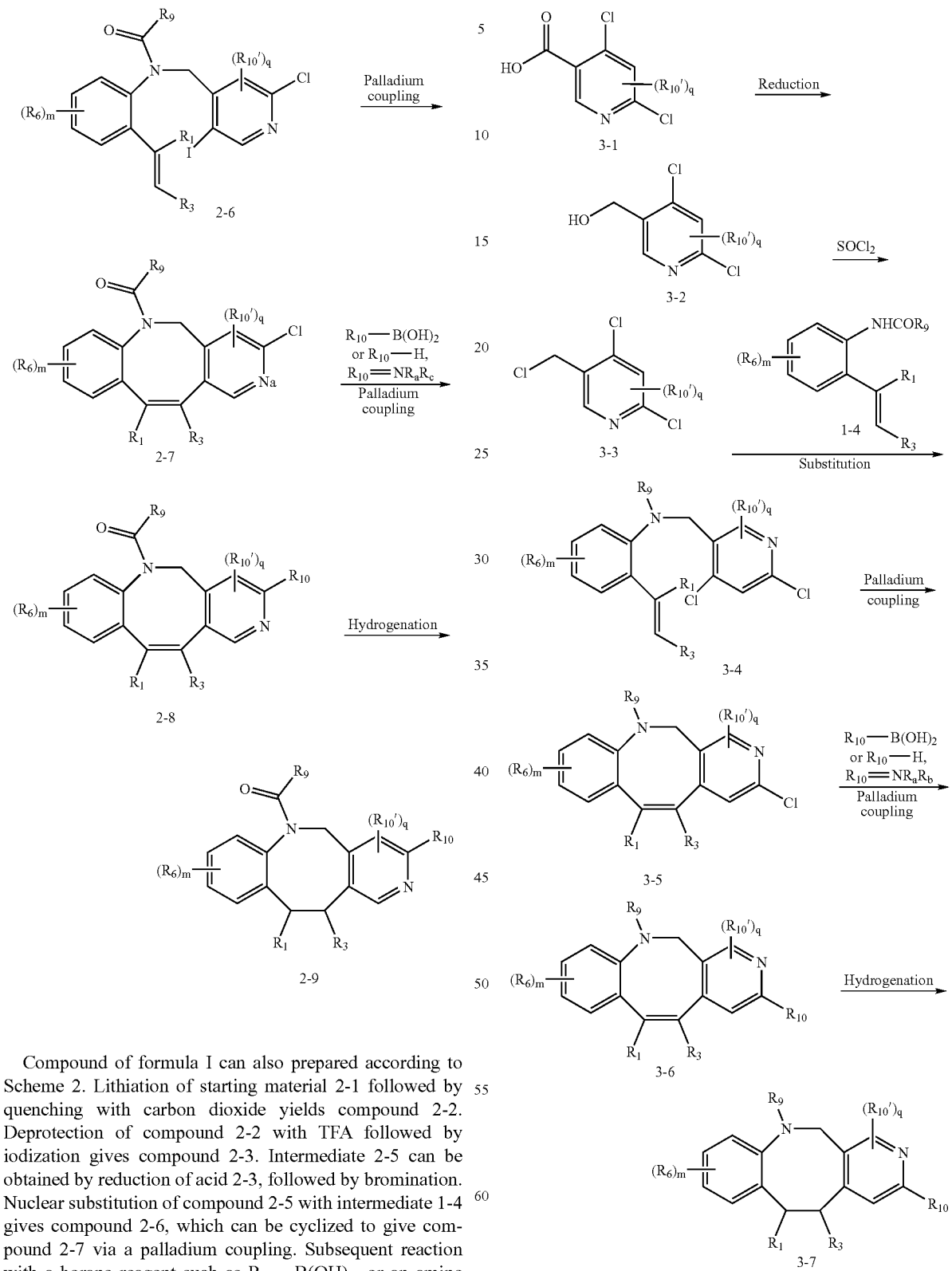

Compound of formula I can also prepared according to Scheme 2. Lithiation of starting material 2-1 followed by quenching with carbon dioxide yields compound 2-2. Deprotection of compound 2-2 with TFA followed by iodization gives compound 2-3. Intermediate 2-5 can be obtained by reduction of acid 2-3, followed by bromination. Nuclear substitution of compound 2-5 with intermediate 1-4 gives compound 2-6, which can be cyclized to give compound 2-7 via a palladium coupling. Subsequent reaction with a borane reagent such as $R_{10}$—$B(OH)_2$, or an amine $HNR_aR_b$, in a palladium coupling condition, generates compound 2-8. Compound 2-9 can be obtained through hydrogenation of compound 2-8.

Similarly, compounds 3-6 and 3-7 can be prepared as shown in Schemes 3.

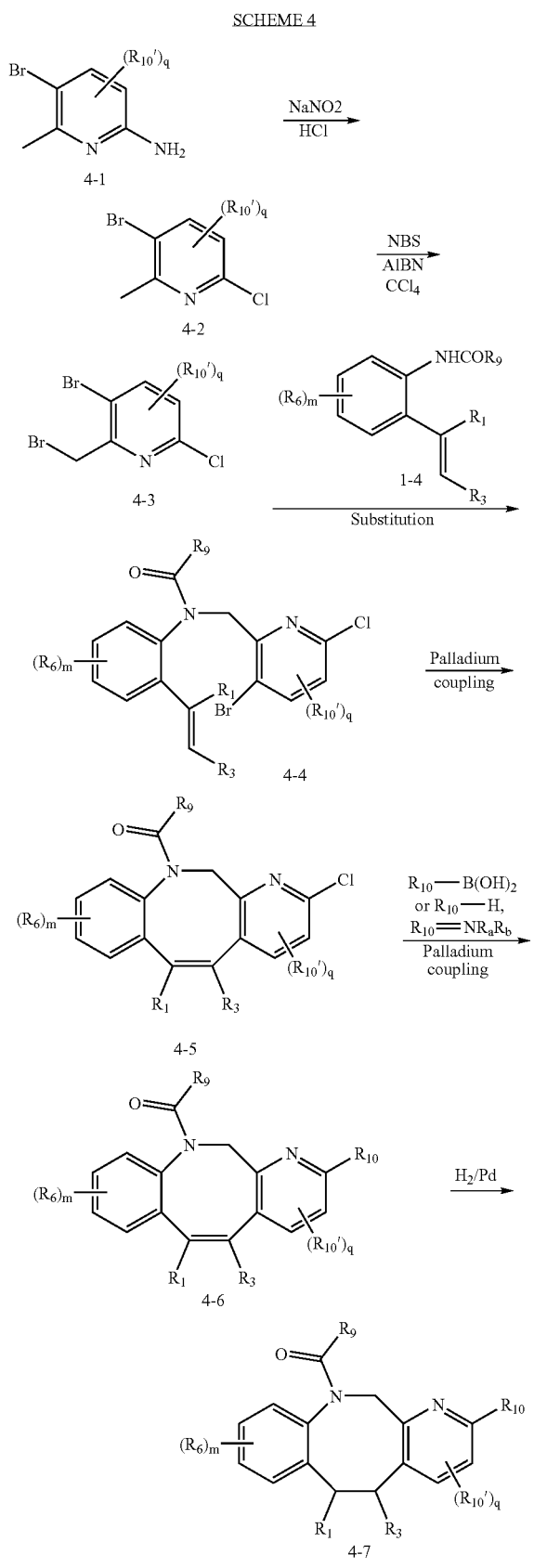

Likewise, compounds 4-6 and 4-7 can be prepared according to Scheme 4. Diazotization of starting material 4-1 followed by yields compound 4-2, which further reacts with a brominating reagent to give intermediate 4-3. Compound 4-5 can be obtained via an internal palladium coupling from intermediate 4-4, which is readily prepared from the nuclear substitution of intermediate 4-3 with compound 1-4. Compound 4-6 can be synthesized from compound 4-5 through a palladium coupling reaction with a borane reagent such as $R_{10}$—$B(OH)_2$, or an amine $HNR_aR_b$. Compound 4-7 can be prepared from 4-6 via hydrogenation.

Compound 5-9 and 5-10-can be prepared according to Scheme 5. Lithiation of starting material 5-1 followed by quenching with dibromoethane affords compound 5-2. Deprotection of 5-2 gives compound 5-3, which can be converted to compound 5-4 through amide coupling. Treatment of 5-4 with a tin reagent 1-3 in the presence of a palladium catalyst yields compound 5-5, which can undergo a nuclear substitution with intermediate 5-6 to give compound 5-7, which can further undergo an internal palladium coupling to offer compound 5-8. Compound 5-9 can be synthesized from compound 5-8 through a palladium coupling reaction with a borane reagent such as $R_{10}$—$B(OH)_2$, or an amine $HNR_aR_b$. Compound 5-10 can be prepared from 5-9 via hydrogenation. Intermediate 5-6 can be readily prepared from reduction of starting material 5-11, followed by bromination.

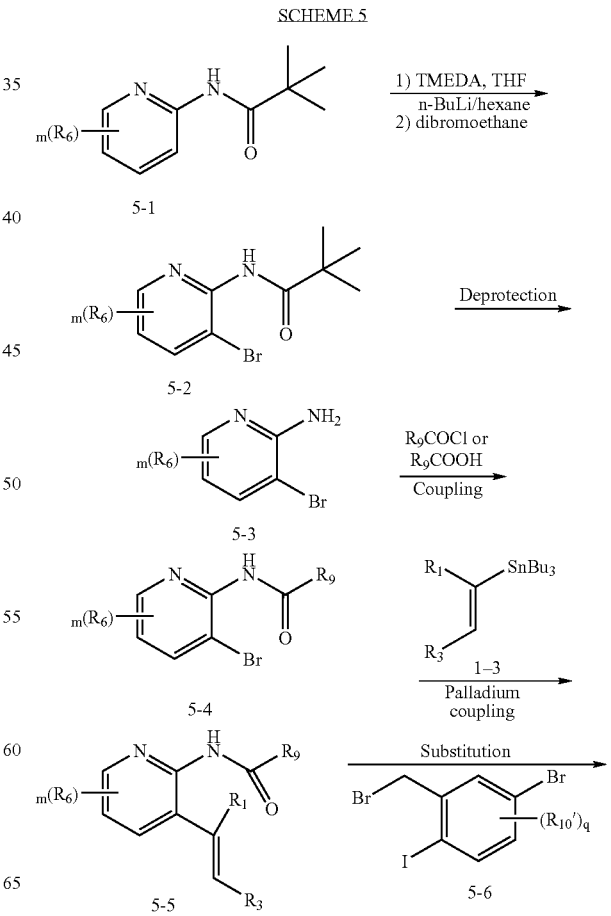

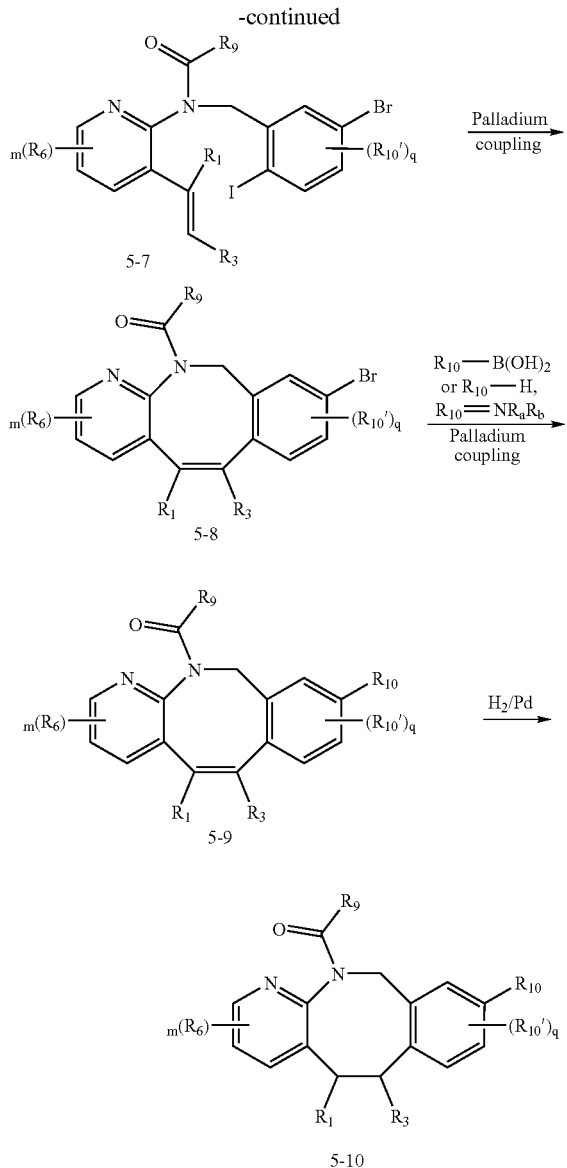

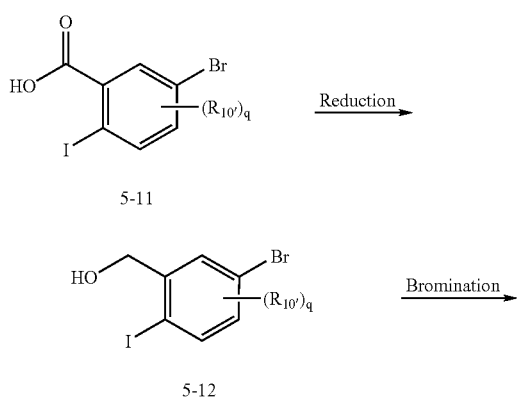

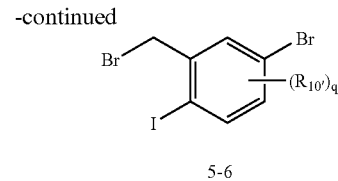

5-6

Compounds C-1, C-2 and C-3 as shown in FIG. 1, can be prepared using a method analogous to that used for the preparation of compound 5-9 and 5-10.

FIG. 1

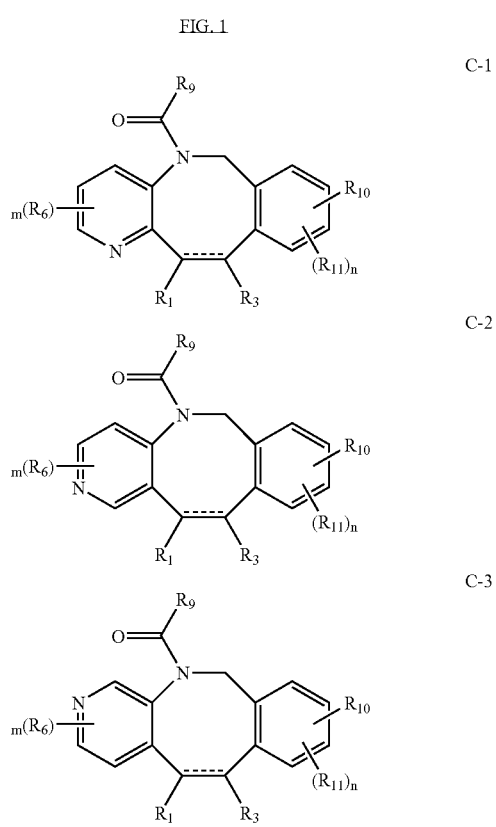

PREFERRED COMPOUNDS

A preferred subgenus of the compounds of the present invention includes compounds of the formula I or salts thereof wherein one or more, preferably all, of the following substituents are as defined below:

$x_1\text{---}x_2$ is —$CR_1$=$CR_3$—, —$CR_1R_2$—$CR_3R_4$—, —C(=O)—$CR_3R_4$—, —S—$CR_3R_4$—, —S(=O)—$CR_3R_4$—, —S(=O)_2—$CR_3R_4$—, —O—$CR_3R_4$—, —$CR_1R_2$—S—, —$CR_1R_2$—S(=O)—, —$CR_1R_2$—S(=O)_2—, —$CR_1R_2$—C(=O)—, or —$CR_1R_2$—O—;

A ring and C ring are each independently phenyl or 5-6 membered heteroaryl, provided that at least one of said A ring and C ring is 5-6 membered heteroaryl;

$R_2$, $R_4$, $R_6$ and $R_{10}$ are each independently hydrogen, cyano, alkyl or substituted alkyl (including $CF_3$), alkenyl or substituted alkenyl, alkynyl or substituted alkynyl, cycloalkyl or substituted cycloalkyl, heterocycle or substituted heterocycle, aryl or substituted aryl, $OR_a$, $SR_a$, $S(=O)R_e$, $S(=O)_2R_e$, $S(=O)_2OR_e$, $NR_bR_c$, $NR_bS(=O)_2R_e$, $S(=O)_2NR_bR_c$, $C(=O)OR_e$, $C(=O)R_a$, $C(=O)NR_bR_c$, $OC(=O)R_a$, $OC(=O)NR_bR_c$, $NR_bC(=O)OR_e$, $NR_dC(=O)NR_bR_c$, $NR_dS(=O)_2NR_bR_c$, $NR_dP(=O)_2NR_bR_c$, $NR_bC(=O)R_a$, $NR_bP(=O)_2R_e$, wherein: $R_2$ and $R_4$ together may optionally form a 3-7 membered optionally substituted carbocyclic ring or 3-7 membered optionally substituted heterocyclic ring; $R_a$, $R_b$, $R_c$, $R_d$ and $R_e$ are as defined above;

$R_1$ and $R_3$ are each independently hydrogen, cyano, nitro, alkyl or substituted alkyl (including $CF_3$), alkenyl or substituted alkenyl, alkynyl or substituted alkynyl, cycloalkyl or substituted cycloalkyl, heterocycle or substituted heterocycle, aryl or substituted aryl, $OR_a$, $SR_a$, $S(=O)R_e$, $S(=O)_2R_e$, $C(=O)OR_e$, $C(=O)R_a$, $NR_bR_c$, $NR_bC(=O)R_a$, $C(=O)NR_bR_c$, $OC(=O)R_a$, or $OC(=O)NR_bR_c$, wherein $R_1$ and $R_3$ together may optionally form a 3-7 membered optionally substituted carbocyclic ring or 3-7 membered optionally substituted heterocyclic ring; $R_a$, $R_b$, $R_c$ and $R_e$ are as described hereinabove;

$R_9$ is H, alkyl or substituted alkyl (including $CF_3$), cycloalkyl or substituted cycloalkyl;

m is 1-4; and n is 1-4;

provided that:

when $x_1\text{-----}x_2$ is $-CH_2-CH_2-$ and when C ring is thiophene, at least one of $R_6$ and $R_{10}$ is not H.

A more preferred subgenus of the compounds of the invention includes compounds of the formula I or an enantiomer, diastereomer, tautomer or pharmaceutically acceptable salt or solvate thereof, wherein one or more, preferably all, of the following substituents are as defined below:

$x_1\text{-----}x_2$ is $-CR_1=CR_3-$, $-CR_1R_2-CR_3R_4-$, $-C(=O)-CR_3R_4-$, $-S-CR_3R_4-$, $-S(=O)-CR_3R_4-$, $-O-CR_3R_4-$, $-CR_1R_2-S-$, $-CR_1R_2-S(=O)-$, $CR_1R_2-C(=O)-$, or $-CR_1R_2-O-$;

A ring and C ring are each independently phenyl or 5-6 membered heteroaryl, provided that at least one of said A ring and C ring is 5-6 membered heteroaryl;

$R_6$ and $R_{10}$ are each independently hydrogen, cyano, nitro, alkyl or substituted alkyl, alkenyl or substituted alkenyl, alkynyl or substituted alkynyl, cycloalkyl or substituted cycloalkyl, heterocycle or substituted heterocycle, aryl or substituted aryl, $OR_a$, $SR_a$, $S(=O)R_e$, $S(=O)_2R_e$, $S(=O)_2OR_e$, $NR_bR_c$, $NR_bS(=O)_2R_e$, $S(=O)_2NR_bR_c$, $C(=O)OR_e$, $C(=O)R_a$, $C(=O)NR_bR_c$, $OC(=O)R_a$, $OC(=O)NR_bR_c$, $NR_bC(=O)OR_e$, $NR_dC(=O)NR_bR_c$, $NR_dS(=O)_2NR_bR_c$, $NR_dP(=O)_2NR_bR_c$, $NR_bC(=O)R_a$, $NR_bP(=O)_2R_e$, wherein $R_a$, $R_b$, $R_c$, $R_d$ and $R_e$ are as defined above;

$R_2$ and $R_4$ are each independently hydrogen, cyano, nitro, alkyl or substituted alkyl (including $CF_3$), cycloalkyl or substituted cycloalkyl, heterocycle or substituted heterocycle, aryl or substituted aryl, $OR_a$, $SR_a$, $S(=O)R_e$, $S(=O)_2R_e$, $NR_bR_c$, $NR_bS(=O)_2R_e$, $S(=O)_2NR_bR_c$, $C(=O)OR_e$, $C(=O)R_a$, $C(=O)NR_bR_c$, $OC(=O)R_a$, $OC(=O)NR_bR_c$, $NR_bC(=O)OR_e$, $NR_dC(=O)NR_bR_c$, $NR_dS(=O)_2NR_bR_c$, $NR_bC(=O)R_a$, wherein $R_2$ and $R_4$ together may optionally form a 3-6 membered optionally substituted carbocyclic ring or 3-6 membered optionally substituted heterocyclic ring, and wherein $R_a$, $R_b$, $R_c$, $R_d$ and $R_e$ are as described hereinabove;

$R_1$ and $R_3$ are each independently hydrogen, cyano, nitro, alkyl or substituted alkyl (including $CF_3$), alkenyl or substituted alkenyl, alkynyl or substituted alkynyl, cycloalkyl or substituted cycloalkyl, heterocycle or substituted heterocycle, aryl or substituted aryl, $OR_a$, $SR_a$, $S(=O)R_e$, $S(=O)_2R_e$, $C(=O)OR_e$, $C(=O)R_a$, $NR_bR_c$, $NR_bC(=O)R_a$, $C(=O)NR_bR_c$, $OC(=O)R_a$, or $OC(=O)NR_bR_c$, wherein $R_1$ and $R_3$ together may optionally form a 3-6 membered optionally substituted carbocyclic ring or 3-6 membered optionally substituted heterocyclic ring; $R_a$, $R_b$, $R_c$ and $R_e$ are as described hereinabove;

$R_9$ is H, $C_1$-$C_4$ alkyl or substituted $C_1$-$C_4$ alkyl (including $CF_3$), cycloalkyl or substituted cycloalkyl;

m is 1-4; and n is 1-4.

provided that:

when $x_1\text{-----}x_2$ is $-CH_2-CH_2-$ and when C ring is thiophene, at least one of $R_6$ and $R_{10}$ is not H.

Another more preferred subgenus of the compounds of the invention includes compounds of the formula I, or an enantiomer, diastereomer, tautomer or pharmaceutically acceptable salt or solvate thereof, wherein one or more, preferably all, of the following substituents are as defined below:

$x_1\text{-----}x_2$ is $-CR_1=CR_3-$, $-CR_1R_2-CR_3R_4-$, $-C(=O)-CR_3R_4-$, $-S-CR_3R_4-$, $-S(=O)-CR_3R_4-$, $-O-CR_3R_4-$, $-CR_1R_2-S-$, or $-CR_1R_2-O-$;

A ring and C ring are each independently phenyl or 5-6 membered heteroaryl, provided that at least one of said A ring and C ring is 5-6 membered heteroaryl;

$R_6$ and $R_{10}$ are each independently hydrogen, cyano, nitro, alkyl or substituted alkyl (including $CF_3$), alkenyl or substituted alkenyl, alkynyl or substituted alkynyl, cycloalkyl or substituted cycloalkyl, heterocycle or substituted heterocycle, aryl or substituted aryl, $OR_a$, $SR_a$, $S(=O)R_e$, $S(=O)_2R_e$, $S(=O)_2OR_e$, $NR_bR_c$, $NR_bS(=O)_2R_e$, $S(=O)_2NR_bR_c$, $C(=O)OR_e$, $C(=O)R_a$, $C(=O)NR_bR_c$, $OC(=O)R_a$, $OC(=O)NR_bR_c$, $NR_bC(=O)OR_e$, $NR_dC(=O)NR_bR_c$, $NR_dS(=O)_2NR_bR_c$, or $NR_bC(=O)R_a$, wherein $R_a$, $R_b$, $R_c$, $R_d$ and $R_e$ are as described hereinabove;

$R_2$ and $R_4$ are each independently hydrogen, cyano, nitro, alkyl or substituted alkyl (including $CF_3$), cycloalkyl or substituted cycloalkyl, heterocycle or substituted heterocycle, aryl or substituted aryl, $OR_a$, $SR_a$, $S(=O)R_e$, $S(=O)_2R_e$, $NR_bR_c$, $NR_bS(=O)_2R_e$, $S(=O)_2NR_bR_c$, $C(=O)OR_e$, $C(=O)R_a$, $C(=O)NR_bR_c$, $OC(=O)R_a$, $OC(=O)NR_bR_c$, $NR_bC(=O)OR_e$, $NR_dC(=O)NR_bR_c$, $NR_dS(=O)_2NR_bR_c$, $NR_bC(=O)R_a$, wherein $R_2$ and $R_4$ together may optionally form a 3-6 membered optionally substituted carbocyclic ring or 3-6 membered optionally substituted heterocyclic ring; $R_a$, $R_b$, $R_c$, $R_d$ and $R_e$ are as described hereinabove;

$R_1$ and $R_3$ are each independently hydrogen, cyano, nitro, alkyl or substituted alkyl (including $CF_3$), alkenyl or substituted alkenyl, alkynyl or substituted alkynyl, cycloalkyl or substituted cycloalkyl, heterocycle or substituted heterocycle, aryl or substituted aryl, $OR_a$, $SR_a$, $S(=O)R_e$, $S(=O)_2R_e$, $C(=O)OR_e$, $C(=O)R_a$, $NR_bR_c$, $NR_bC(=O)R_a$, $C(=O)NR_bR_c$, $OC(=O)R_a$, or $OC(=O)NR_bR_c$, wherein $R_1$ and $R_3$ together may optionally form a 3-6 membered optionally substituted carbocyclic ring or 3-6 membered optionally substituted heterocyclic ring; $R_a$, $R_b$, $R_c$ and $R_e$ are as described hereinabove;

$R_9$ is H, methyl, ethyl, isopropyl, $CF_3$, or cyclopropyl;

m is 1-3; and n is 1-3;

provided that:

when $x_1\text{-----}x_2$ is $-CH_2-CH_2-$ and when C ring is thiophene, at least one of $R_6$ and $R_{10}$ is not H.

A particularly preferred subgenus of the compounds of the invention includes compounds of the formula I, or an enantiomer, diastereomer, tautomer or pharmaceutically acceptable salt or solvate thereof, wherein one or more, preferably all, of the following substituents are as defined below:

$x_1\text{-----}x_2$ is —CR$_1$=CR$_3$—, —CR$_1$R$_2$—CR$_3$R$_4$—, —C(=O)—CR$_3$R$_4$—;

A ring and C ring are each independently phenyl or 5-6 membered heteroaryl, provided that at least one of said A ring and C ring is 5-6 membered heteroaryl;

R$_6$ is hydrogen, halogen, cyano, nitro, SMe, S(=O)$_2$Me, or OMe;

R$_{10}$ is hydrogen, cyano, nitro, alkyl or substituted alkyl (including CF$_3$), alkenyl or substituted alkenyl, alkynyl or substituted alkynyl, cycloalkyl or substituted cycloalkyl, heterocycle or substituted heterocycle, aryl or substituted aryl, OR$_a$, SR$_a$, S(=O)R$_e$, S(=O)$_2$R$_e$, S(=O)$_2$OR$_e$, NR$_b$R$_c$, NR$_b$S(=O)$_2$R$_e$, S(=O)$_2$NR$_b$R$_c$, C(=O)OR$_e$, C(=O)R$_a$, C(=O)NR$_b$R$_c$, OC(=O)R$_a$, OC(=O)NR$_b$R$_c$, NR$_b$C(=O)OR$_e$, NR$_d$C(=O)NR$_b$R$_c$, NR$_d$S(=O)$_2$NR$_b$R$_c$, NR$_d$P(=O)$_2$NR$_b$R$_c$, NR$_b$C(=O)R$_a$, or NR$_b$P(=O)$_2$R$_e$, wherein R$_a$, R$_b$, R$_c$, R$_d$ and R$_e$ are as described hereinabove;

R$_2$ and R$_4$ are each independently hydrogen, cyano, nitro, alkyl or substituted alkyl (including CF$_3$), cycloalkyl or substituted cycloalkyl, heterocycle or substituted heterocycle, aryl or substituted aryl, OR$_a$, SR$_a$, S(=O)R$_e$, S(=O)$_2$R$_e$, NR$_b$R$_c$, NR$_b$S(=O)$_2$R$_e$, S(=O)$_2$NR$_b$R$_c$, C(=O)OR$_e$, C(=O)R$_a$, C(=O)NR$_b$R$_c$, OC(=O)R$_a$, OC(=O)NR$_b$R$_c$, NR$_b$C(=O)OR$_e$, NR$_d$C(=O)NR$_b$R$_c$, NR$_d$S(=O)$_2$NR$_b$R$_c$, NR$_b$C(=O)R$_a$, wherein R$_2$ and R$_4$ together may optionally form a 3-6 membered optionally substituted carbocyclic ring or 3-6 membered optionally susbtituted heterocyclic ring; R$_a$, R$_b$, R$_c$, R$_d$ and R$_e$ are as described hereinabove;

R$_1$ and R$_3$ are each independently hydrogen, cyano, nitro, alkyl or substituted alkyl (including CF$_3$), alkenyl or substituted alkenyl, alkynyl or substituted alkynyl, cycloalkyl or substituted cycloalkyl, heterocycle or substituted heterocycle, aryl or substituted aryl, OR$_a$, SR$_a$, S(=O)R$_e$, S(=O)$_2$R$_e$, C(=O)OR$_e$, C(=O)R$_a$, NR$_b$R$_c$, NR$_b$C(=O)R$_a$, C(=O)NR$_b$R$_c$, OC(=O)R$_a$, or OC(=O)NR$_b$R$_c$, wherein R$_1$ and R$_3$ together may optionally form a 3-7 membered optionally susbtituted carbocyclic ring or 3-7 membered optionally susbtituted heterocyclic ring; R$_a$, R$_b$, R$_c$ and R$_e$ are as described hereinabove;

R$_9$ is methyl;

m is 1-3; and n is 1-3;

provided that:

when $x_1\text{-----}x_2$ is —CH$_2$—CH$_2$— and when C ring is thiophene, at least one of R$_6$ and R$_{10}$ is not H.

Another particularly preferred subgenus of the compounds of the invention includes compounds of the formula I, or an enantiomer, diastereomer, tautomer or pharmaceutically acceptable salt or solvate thereof, wherein one or more, preferably all, of the following substituents are as defined below:

$x_1\text{-----}x_2$ is —S—CR$_3$R$_4$—;

A ring and C ring are each independently phenyl or 5-6 membered heteroaryl, provided that at least one of said A ring and C ring is 5-6 membered heteroaryl;

R$_6$ is hydrogen, halogen, cyano, nitro, SMe, S(=O)$_2$Me, or OMe;

R$_{10}$ is hydrogen, cyano, alkyl or substituted alkyl (including CF$_3$), alkenyl or substituted alkenyl, alkynyl or substituted alkynyl, cycloalkyl or substituted cycloalkyl, heterocycle or substituted heterocycle, aryl or substituted aryl, OR$_a$, SR$_a$, S(=O)R$_e$, S(=O)$_2$R$_e$, S(=O)$_2$OR$_e$, NR$_b$R$_c$, NR$_b$S(=O)$_2$R$_e$, S(=O)$_2$NR$_b$R$_c$, C(=O)OR$_e$, C(=O)R$_a$, C(=O)NR$_b$R$_c$, OC(=O)R$_a$, OC(=O)NR$_b$R$_c$, NR$_b$C(=O)OR$_e$, NR$_d$C(=O)NR$_b$R$_c$, NR$_d$S(=O)$_2$NR$_b$R$_c$, or NR$_b$C(=O)R$_a$, wherein R$_a$, R$_b$, R$_c$, R$_d$ and R$_e$ are as described hereinabove;

R$_3$ and R$_4$ are each independently hydrogen, cyano, nitro, alkyl or substituted alkyl (including CF$_3$), alkenyl or substituted alkenyl, alkynyl or substituted alkynyl, cycloalkyl or substituted cycloalkyl, heterocycle or substituted heterocycle, aryl or substituted aryl, OR$_a$, SR$_a$, S(=O)R$_e$, S(=O)$_2$R$_e$, C(=O)OR$_e$, C(=O)R$_a$, C(=O)NR$_b$R$_c$, OC(=O)R$_a$, or OC(=O)NR$_b$R$_c$, wherein R$_a$, R$_b$, R$_c$ and R$_e$ are as described hereinabove;

R$_9$ is methyl;

m is 1-3; and n is 1-3;

Another particularly preferred subgenus of the compounds of the invention includes compounds of the formula I having the structure Ib as shown above, or an enantiomer, diastereomer, tautomer or pharmaceutically acceptable salt or solvate thereof, wherein one or more, preferably all, of the following substituents are as defined below:

$x_1\text{-----}x_2$ is —O—CR$_3$R$_4$—, —CR$_1$R$_2$—S—, or —CR$_1$R$_2$—O—;

A ring and C ring are each independently phenyl or 5-6 membered heteroaryl, provided that at least one of said A ring and C ring is 5-6 membered heteroaryl;

R$_6$ is hydrogen, halogen, cyano, nitro, SMe, S(=O)$_2$Me, or OMe;

R$_{10}$ is hydrogen, cyano, nitro, alkyl or substituted alkyl (including CF$_3$), alkenyl or substituted alkenyl, alkynyl or substituted alkynyl, cycloalkyl or substituted cycloalkyl, heterocycle or substituted heterocycle, aryl or substituted aryl, OR$_a$, SR$_a$, S(=O)R$_e$, S(=O)$_2$R$_e$, S(=O)$_2$OR$_e$, NR$_b$R$_c$, NR$_b$S(=O)$_2$R$_e$, S(=O)$_2$NR$_b$R$_c$, C(=O)OR$_e$, C(=O)R$_a$, C(=O)NR$_b$R$_c$, OC(=O)R$_a$, OC(=O)NR$_b$R$_c$, NR$_b$C(=O)OR$_e$, NR$_d$C(=O)NR$_b$R$_c$, NR$_d$S(=O)$_2$NR$_b$R$_c$, NR$_d$P(=O)$_2$NR$_b$R$_c$, NR$_b$C(=O)R$_a$, NR$_b$P(=O)$_2$R$_e$, wherein R$_a$, R$_b$, R$_c$, R$_d$ and R$_e$ are as described hereinabove;

R$_1$, R$_2$, R$_3$ and R$_4$ are each independently hydrogen, cyano, nitro, alkyl or substituted alkyl (including CF$_3$), alkenyl or substituted alkenyl, alkynyl or substituted alkynyl, cycloalkyl or substituted cycloalkyl, heterocycle or substituted heterocycle, aryl or substituted aryl, OR$_a$, SR$_a$, S(=O)R$_e$, S(=O)$_2$R$_e$, C(=O)OR$_e$, C(=O)R$_a$, NR$_b$R$_c$, NR$_b$C(=O)R$_a$, C(=O)NR$_b$R$_c$, OC(=O)R$_a$, or OC(=O)NR$_b$R$_c$, wherein R$_a$, R$_b$, R$_c$ and R$_e$ are as described hereinabove;

R$_9$ is methyl;

m is 1-3; and n is 1-3.

Especially preferred subgenus of the compounds of the invention includes compounds of the formula I having the following structure Ia, or an enantiomer, diastereomer, tautomer or pharmaceutically acceptable salt or solvate thereof, wherein one or more, preferably all, of the following substituents are as defined below:

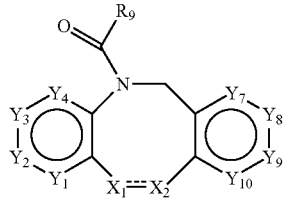

$x_1 \text{-----} x_2$ is —CH=CH—, —CH$_2$—CH$_2$—;
Y$_1$, Y$_4$, Y$_7$ and Y$_{10}$ are each independently CH or N;
Y$_2$ is CR$_7$ or N;
Y$_3$ is CR$_8$ or N;
Y$_8$ is CR$_{10}$ or N;
Y$_9$ is CR$_{11}$ or N;
provided that at least one of Y$_1$, Y$_2$, Y$_3$, Y$_4$, Y$_7$, Y$_8$, Y$_9$ and Y$_{10}$ is N;
R$_7$ and R$_8$ are each independently hydrogen, halogen, cyano, nitro, SMe, S(=O)$_2$Me, or OMe;
R$_{10}$ and R$_{11}$ are each independently hydrogen, cyano, nitro, alkyl or substituted alkyl (including CF$_3$), alkenyl or substituted alkenyl, alkynyl or substituted alkynyl, cycloalkyl or substituted cycloalkyl, heterocycle or substituted heterocycle, aryl or substituted aryl, OR$_e$, SR$_e$, S(=O)R$_e$, S(=O)$_2$R$_e$, S(=O)$_2$OR$_e$, NR$_b$R$_c$, NR$_b$S(=O)$_2$R$_e$, S(=O)$_2$NR$_b$R$_c$, C(=O)OR$_e$, C(=O)R$_a$, C(=O)NR$_b$R$_c$, OC(=O)R$_a$, OC(=O)NR$_b$R$_c$, NR$_b$C(=O)OR$_e$, NR$_d$C(=O)NR$_b$R$_c$, NR$_d$S(=O)$_2$NR$_b$R$_c$, NR$_b$C(=O)R$_a$, wherein R$_a$, R$_b$, R$_c$, R$_d$ and R$_e$ are as described hereinabove; and
R$_9$ is methyl.

Another especially preferred subgenus of the compounds of the invention includes compounds of the formula I having the following structure Ib, or an enantiomer, diastereomer, tautomer or pharmaceutically acceptable salt or solvate thereof, wherein one or more, preferably all, of the following substituents are as defined below:

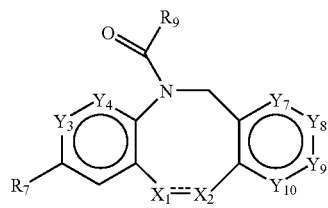

$x_1 \text{-----} x_2$ is —CH=CH—, —CH$_2$—CH$_2$—;
Y$_4$, Y$_7$ and Y$_{10}$ are each independently CH or N;
Y$_3$ is CR$_8$ or N;
Y$_8$ is CR$_{10}$ or N;
Y$_9$ is CR$_{11}$ or N;
provided that the total number of N atoms among Y$_3$, Y$_4$, Y$_7$, Y$_8$, Y$_9$ and Y$_{10}$ is one, two, or three;
R$_7$ and R$_8$ are each independently hydrogen, halogen, cyano, nitro, S(=O)$_2$Me, or OMe;
R$_{10}$ and R$_{11}$ are each independently hydrogen, halogen, cyano, nitro, alkyl or substituted alkyl (including CF$_3$), cycloalkyl or substituted cycloalkyl, heterocycle or substituted heterocycle, aryl or substituted aryl, OR$_e$, SR$_e$, S(=O)R$_e$, S(=O)$_2$R$_e$, NR$_b$R$_c$, C(=O)OR$_e$, C(=O)R$_a$, C(=O)NR$_b$R$_c$, NR$_b$C(=O)OR$_e$, NR$_b$C(=O)R$_a$, wherein R$_a$, R$_b$, R$_c$, R$_d$ and R$_e$ are as described hereinabove; and
R$_9$ is methyl.

USE AND UTILITY

The compounds of present invention are inhibitors of 17β-hydroxysteroid dehydrogenase 3 (17β-HSD3). They are useful in the treatment of androgen-associated conditions. An "androgen-associated condition," as used herein, denotes a condition or disorder that is caused or aided by modulation of the activity of the androgen receptor. The androgen-associated conditions can be treated by the reduction of androgen biosynthesis through inhibiting 17β-HSD3, wherein treatment comprises prevention, partial alleviation or cure of the condition or disorder.

The present compounds are also useful in the treatment of estrogen-associated conditions. An "estrogen-associated condition," as used herein, refers to a condition or disorder that is caused or aided by modulation of the activity of the estrogen receptor. The estrogen-associated conditions can also be treated by the reduction of androgen biosynthesis through inhibiting 17β-HSD3 because many androgens are precursors to estrogens. The treatment herein comprises prevention, partial alleviation or cure of the condition or disorder.

Further, estrogen-associated conditions may respond differently to androgens, i.e., they may respond adversely, favorably or neutrally to androgens. Similarly, androgen-associated conditions may vary in their responses to estrogens. Hence, treatment of a hormone sensitive disorder may adjust (i.e., increase or decrease) androgenic activity depending on whether the disorder reacts favorably or adversely toward androgenic activity. Likewise, treatment may also employ adjusting (i.e., increasing or decreasing) estrogenic activity depending on whether the disorder reacts favorably or adversely toward estrogenic activity. For example, prostate cancer responds adversely to androgenic activity and favorably to estrogenic activity; and breast cancer responds favorably to androgenic activity and adversely to estrogenic activity.

The treatment in both androgen- and estrogen-associated conditions may occur locally, for example, within certain tissues of the subject, or more extensively throughout a subject being treated for such a condition disorder.

The compounds of the present invention are useful for the treatment of a variety of conditions and disorders including, but not limited to, those described following.

Compounds of formula I can be used as inhibitors of 17β-HSD3 enzyme, preferably selectively to that enzyme, in an array of androgen-associated conditions. Applications of said compounds include but are not limited to: prostate cancer, hirsutism, acne, seborrhea, precocious puberty, Alzheimer's disease, androgenic alopecia, hypogonadism, hyperpilosity, benign prostate hypertrophia, benign prostatic hyperplasia, adenomas and neoplasies of the prostate (such as advanced metastatic prostate cancer), treatment of benign or malignant tumor cells containing the androgen receptor such as is the case for breast, brain, skin, ovarian, bladder, lymphatic, liver and kidney cancers, pancreatic cancers modulation of VCAM expression and applications therein for the treatment of heart disease, inflammation and immune modulations, modulation of VEGF expression and the applications therein for use as antiandrogenic agents, osteoporosis, suppressing spermatogenesis, libido, cachexia, endometriosis, polycystic ovary syndrome, anorexia, androgen supplement for age related decreased testosterone levels in men, male menopause, male hormone replacement, male and female sexual dysfunction, and inhibition of muscular atrophy in ambulatory patients.

Compounds of formula I can also be applied in an array of estrogen-associated conditions. Applications of said compounds include but are not limited to: osteoporosis, hot flushes, vaginal dryness, breast cancer, ovarian cancer, uterine cancer, endometrial cancer, cancers expressing the estrogen receptor such as the aforementioned cancers and others, endometriosis, endometrial leiomyoma, contraception, pregnancy termination, menopause, amennoreahea, and dysmennoreahea.

The present invention thus provides methods for the treatment of androgen-associated or estrogen-associated conditions, comprising the step of administering to a subject in need thereof at least one compound of formula I in an amount effective therefor. Other therapeutic agents such as those described below may be employed with the inventive compounds in the present methods (for example, separately, or formulated together as a fixed dose). In the methods of the present invention, such other therapeutic agent(s) can be administered prior to, simultaneously with or following the administration of the compound(s) of the present invention.

The present invention also provides pharmaceutical compositions comprising at least one of the compounds of the formula I capable of treating an androgen-associated or estrogen-associated condition in an amount effective therefor, and a pharmaceutically acceptable carrier (vehicle or diluent). The compositions of the present invention can contain other therapeutic agents as described below, and can be formulated, for example, by employing conventional solid or liquid vehicles or diluents, as well as pharmaceutical additives of a type appropriate to the mode of desired administration (for example, excipients, binders, preservatives, stabilizers, flavors, etc.) according to techniques such as those well known in the art of pharmaceutical formulation.

It should be noted that the compounds of the present invention are, without limitation as to their mechanism of action, useful in treating any of the conditions or disorders listed or described herein such as inflammatory diseases or cancers, or other proliferate diseases, and in compositions for treating such conditions or disorders. Such conditions and disorders include, without limitation, any of those described previously, as well as those described following such as: maintenance of muscle strength and function (e.g., in the elderly); reversal or prevention of frailty or age-related functional decline ("ARFD") in the elderly (e.g., sarcopenia); treatment of catabolic side effects of glucocorticoids; prevention and/or treatment of reduced bone mass, density or growth (e.g., osteoporosis and osteopenia); treatment of chronic fatigue syndrome (CFS); chronic malagia; treatment of acute fatigue syndrome and muscle loss following elective surgery (e.g., post-surgical rehabilitation); acceleration of wound healing; accelerating bone fracture repair (such as accelerating the recovery of hip fracture patients); accelerating healing of complicated fractures, e.g. distraction osteogenesis; in joint replacement; prevention of post-surgical adhesion formation; acceleration of tooth repair or growth; maintenance of sensory function (e.g., hearing, sight, olefaction and taste); treatment of periodontal disease; treatment of wasting secondary to fractures and wasting in connection with chronic obstructive pulmonary disease (COPD), chronic liver disease, AIDS, weightlessness, cancer cachexia, burn and trauma recovery, chronic catabolic state (e.g., coma), eating disorders (e.g., anorexia) and chemotherapy; treatment of cardiomyopathy; treatment of thrombocytopenia; treatment of growth retardation in connection with Crohn's disease; treatment of short bowel syndrome; treatment of irritable bowel syndrome; treatment of inflammatory bowel disease; treatment of Crohn's disease and ulcerative colits; treatment of complications associated with transplantation; treatment of physiological short stature including growth hormone deficient children and short stature associated with chronic illness; treatment of obesity and growth retardation associated with obesity; treatment of anorexia (e.g., associated with cachexia or aging); treatment of hypercortisolism and Cushing's syndrome; Paget's disease; treatment of osteoarthritis; induction of pulsatile growth hormone release; treatment of osteochondrodysplasias; treatment of depression, nervousness, irritability and stress; treatment of reduced mental energy and low self-esteem (e.g., motivation/assertiveness); improvement of cognitive function (e.g., the treatment of dementia, including Alzheimer's disease and short term memory loss); treatment of catabolism in connection with pulmonary dysfunction and ventilator dependency; treatment of cardiac dysfunction (e.g., associated with valvular disease, myocardial infarction, cardiac hypertrophy or congestive heart failure); lowering blood pressure; protection against ventricular dysfunction or prevention of reperfusion events; treatment of adults in chronic dialysis; reversal or slowing of the catabolic state of aging; attenuation or reversal of protein catabolic responses following trauma (e.g., reversal of the catabolic state associated with surgery, congestive heart failure, cardiac myopathy, burns, cancer, COPD etc.); reducing cachexia and protein loss due to chronic illness such as cancer or AIDS; treatment of hyperinsulinemia including nesidioblastosis; treatment of immunosuppressed patients; treatment of wasting in connection with multiple sclerosis or other neurodegenerative disorders; promotion of myelin repair; maintenance of skin thickness; treatment of metabolic homeostasis and renal homeostasis (e.g., in the frail elderly); stimulation of osteoblasts, bone remodeling and cartilage growth; regulation of food intake; treatment of insulin resistance, including NIDDM, in mammals (e.g., humans); treatment of insulin resistance in the heart; improvement of sleep quality and correction of the relative hyposomatotropism of senescence due to high increase in REM sleep and a decrease in REM latency; treatment of hypothermia; treatment of congestive heart failure; treatment of lipodystrophy (e.g., in patients taking HIV or AIDS therapies such as protease inhibitors); treatment of muscular atrophy (e.g., due to physical inactivity, bed rest or reduced weight-bearing conditions); treatment of musculoskeletal impairment (e.g., in the elderly); improvement of the overall pulmonary function; treatment of sleep disorders; and the treatment of the catabolic state of prolonged critical illness; treatment of hirsutism, acne, seborrhea, androgenic alopecia, anemia, hyperpilosity, benign prostate hypertrophy, adenomas and neoplasies of the prostate (e.g., advanced metastatic prostate cancer) and malignant tumor cells containing the androgen receptor, such as is the case for breast, brain, skin, ovarian, bladder, lymphatic, liver and kidney cancers; cancers of the skin, pancreas, endometrium, lung and colon; osteosarcoma; hypercalcemia of malignancy; metastatic bone disease; treatment of spermatogenesis, endometriosis and polycystic ovary syndrome; counteracting preeclampsia, eclampsia of pregnancy and preterm labor; treatment of premenstrual syndrome; treatment of vaginal dryness; age related decreased testosterone levels in men, male menopause, hypogonadism, male hormone replacement, male and female sexual dysfunction (e.g., erectile dysfunction, decreased sex drive, sexual well-being, decreased libido), male and female contraception, hair loss, Reaven's Syndrome and the enhancement of bone and muscle performance/strength; and the conditions, diseases, and maladies collectively referenced to as "Syndrome X" or Metabolic Syndrome as detailed in Johannsson *J. Clin. Endocrinol. Metab.*, 82, 727-34 (1997).

The present compounds have therapeutic utility in the modulation of immune cell activation/proliferation, e.g., as competitive inhibitors of intercellular ligand/receptor binding reactions involving CAMs (Cellular Adhesion Molecules) and Leukointegrins. For example, the present compounds modulate LFA-ICAM 1, and are particularly useful as LFA-ICAM 1 antagonists, and in the treatment of all conditions associated with LFA-ICAM 1 such as immunological disorders. Preferred utilities for the present compounds include, but are not limited to: inflammatory conditions such as those resulting from a response of the non-specific immune system in a mammal (e.g., adult respiratory distress syndrome, shock, oxygen toxicity, multiple organ injury syndrome secondary to septicemia, multiple organ injury syndrome secondary to trauma, reperfusion injury of tissue due to cardiopulmonary bypass, myocardial infarction or use with thrombolysis agents, acute glomerulonephritis, vasculitis, reactive arthritis, dermatosis with acute inflammatory components, stroke, thermal injury, hemodialysis, leukapheresis, ulcerative colitis, necrotizing enterocolitis and granulocyte transfusion associated syndrome) and conditions resulting from a response of the specific immune system in a mammal (e.g., psoriasis, organ/tissue transplant rejection, graft vs. host reactions and autoimmune diseases including Raynaud's syndrome, autoimmune thyroiditis, dermatitis, multiple sclerosis, rheumatoid arthritis, insulin-dependent diabetes mellitus, uveitis, inflammatory bowel disease including Crohn's disease and ulcerative colitis, and systemic lupus erythematosus). The present compounds can be used in treating asthma or as an adjunct to minimize toxicity with cytokine therapy in the treatment of cancers. The present compounds can be employed in the treatment of all diseases currently treatable through steroid therapy. The present compounds may be employed for the treatment of these and other disorders alone or with other immunosuppressive or antiinflammatory agents. In accordance with the invention, a compound of the formula I can be administered prior to the onset of inflammation (so as to suppress an anticipated inflammation) or after the initiation of inflammation. When provided prophylactically, the immunosuppressive compound(s) are preferably provided in advance of any inflammatory response or symptom (for example, prior to, at, or shortly after the time of an organ or tissue transplant but in advance of any symptoms or organ rejection). The prophylactic administration of a compound of the formula I prevents or attenuates any subsequent inflammatory response (such as, for example, rejection of a transplanted organ or tissue, etc.) Administration of a compound of the formula I attenuates any actual inflammation (such as, for example, the rejection of a transplanted organ or tissue).

The compounds of the formula I can be administered for any of the uses described herein by any suitable means, for example, orally, such as in the form of tablets, capsules, granules or powders; sublingually; bucally; parenterally, such as by subcutaneous, intravenous, intramuscular, or intrasternal injection or infusion techniques (e.g., as sterile injectable aqueous or non-aqueous solutions or suspensions); nasally, including administration to the nasal membranes, such as by inhalation spray; topically, such as in the form of a cream or ointment; or rectally such as in the form of suppositories; in dosage unit formulations containing non-toxic, pharmaceutically acceptable vehicles or diluents. The present compounds can, for example, be administered in a form suitable for immediate release or extended release. Immediate release or extended release can be achieved by the use of suitable pharmaceutical compositions comprising the present compounds, or, particularly in the case of extended release, by the use of devices such as subcutaneous implants or osmotic pumps. The present compounds can also be administered liposomally.

Exemplary compositions for oral administration include suspensions which can contain, for example, microcrystalline cellulose for imparting bulk, alginic acid or sodium alginate as a suspending agent, methylcellulose as a viscosity enhancer, and sweeteners or flavoring agents such as those known in the art; and immediate release tablets which can contain, for example, microcrystalline cellulose, dicalcium phosphate, starch, magnesium stearate and/or lactose and/or other excipients, binders, extenders, disintegrants, diluents and lubricants such as those known in the art. The compounds of formula I can also be delivered through the oral cavity by sublingual and/or buccal administration. Molded tablets, compressed tablets or freeze-dried tablets are exemplary forms that may be used. Exemplary compositions include those formulating the present compound(s) with fast dissolving diluents such as mannitol, lactose, sucrose and/or cyclodextrins. Also included in such formulations may be high molecular weight excipients such as celluloses (avicel) or polyethylene glycols (PEG). Such formulations can also include an excipient to aid mucosal adhesion such as hydroxy propyl cellulose (HPC), hydroxy propyl methyl cellulose (HPMC), sodium carboxy methylcellulose (SCMC), maleic anhydride copolymer (e.g., Gantrez), and agents to control release such as polyacrylic copolymer (e.g. Carbopol 934). Lubricants, glidants, flavors, coloring agents and stabilizers may also be added for ease of fabrication and use.

Exemplary compositions for nasal aerosol or inhalation administration include solutions in saline which can contain, for example, benzyl alcohol or other suitable preservatives, absorption promoters to enhance bioavailability, and/or other solubilizing or dispersing agents such as those known in the art.

Exemplary compositions for parenteral administration include injectable solutions or suspensions which can contain, for example, suitable non-toxic, parenterally acceptable diluents or solvents, such as mannitol, ethanol, 1,3-butanediol, water, Ringer's solution, an isotonic sodium chloride solution, or other suitable dispersing or wetting and suspending agents, including synthetic mono- or diglycerides, and fatty acids, including oleic acid, or Cremaphor.

Exemplary compositions for rectal administration include suppositories which can contain, for example, a suitable non-irritating excipient, such as cocoa butter, synthetic glyceride esters or polyethylene glycols, which are solid at ordinary temperatures, but liquify and/or dissolve in the rectal cavity to release the drug.

Exemplary compositions for topical administration include a topical carrier such as Plastibase (mineral oil gelled with polyethylene).

The effective amount of a compound of the present invention can be determined by one of ordinary skill in the art, and includes exemplary dosage amounts for a adult human of from about 1 to 100 (for example, 15) mg/kg of body weight of active compound per day, which can be administered in a single dose or in the form of individual divided doses, such as from 1 to 4 times per day. It will be understood that the specific dose level and frequency of dosage for any particular subject can be varied and will depend upon a variety of factors including the activity of the specific compound employed, the metabolic stability and length of action of that compound, the species, age, body weight, general health, sex and diet of the subject, the mode and time of administration, rate of excretion, drug combination, and severity of the particular condition. Preferred subjects for treatment include animals, most preferably mammalian species such as humans, and domestic animals such as dogs, cats and the like, subject to androgen-associated and/or estrogen-associated conditions.

As mentioned above, the compounds of the present invention can be employed alone or in combination with each other and/or other suitable therapeutic agents useful in the treatment of androgen-associated and/or estrogen-associated conditions, e.g., an antibiotic or other pharmaceutically active material.

For example, the compounds of the present invention can be combined with growth promoting agents, such as, but not limited to, TRH (Thyroid Receptor Hormone), diethylstilbesterol, theophylline, enkephalins, E series prostaglandins, compounds disclosed in U.S. Pat. No. 3,239,345, e.g., zeranol, and compounds disclosed in U.S. Pat. No. 4,036,979, e.g., sulbenox or peptides disclosed in U.S. Pat. No. 4,411,890.

The compounds of the invention can also be used in combination with growth hormone secretagogues such as GHRP-6, GHRP-1 (as described in U.S. Pat. No. 4,411,890 and publications WO 89/07110 and WO 89/07111), GHRP-2 (as described in WO 93/04081), NN703 (Novo Nordisk), LY444711 (Lilly), MK-677 (Merck), CP424391 (Pfizer) and B-HT920, or with growth hormone releasing factor and its analogs or growth hormone and its analogs or somatomedins including IGF-1 and IGF-2, or with alpha-adrenergic agonists, such as clonidine or serotinin 5-HT$_D$ agonists, such as sumatriptan, or agents which inhibit somatostatin or its release, such as physostigmine and pyridostigmine. A still further use of the disclosed compounds of the invention is in combination with parathyroid hormone, PTH(1-34) or bis-phosphonates, such as MK-217 (alendronate).

A still further use of the compounds of the invention is in combination with estrogen, testosterone, a selective estrogen receptor modulator, such as tamoxifen or raloxifene, or other androgen receptor modulators, such as those disclosed in Edwards, J. P. et al., *Bio. Med. Chem. Let.*, 9, 1003-1008 (1999) and Hamann, L. G. et al., *J. Med. Chem.*, 42, 210-212 (1999).

A further use of the compounds of this invention is in combination with progesterone receptor agonists ("PRA"), such as levonorgestrel, medroxyprogesterone acetate (MPA).

The compounds of the present invention can be employed alone or in combination with each other and/or other modulators of nuclear hormone receptors or other suitable therapeutic agents useful in the treatment of the aforementioned disorders including: anti-diabetic agents; anti-osteoporosis agents; anti-obesity agents; anti-inflammatory agents; anti-anxiety agents; anti-depressants; anti-hypertensive agents; anti-platelet agents; anti-thrombotic and thrombolytic agents; cardiac glycosides; cholesterol/lipid lowering agents; mineralocorticoid receptor antagonists; phospodiesterase inhibitors; protein tyrosine kinase inhibitors; thyroid mimetics (including thyroid receptor agonists); anabolic agents; HIV or AIDS therapies; therapies useful in the treatment of Alzheimer's disease and other cognitive disorders; therapies useful in the treatment of sleeping disorders; anti-proliferative agents; and anti-tumor agents.

Examples of suitable anti-diabetic agents for use in combination with the compounds of the present invention include biguanides (e.g., metformin), glucosidase inhibitors (e,g,. acarbose), insulins (including insulin secretagogues or insulin sensitizers), meglitinides (e.g., repaglinide), sulfonylureas (e.g., glimepiride, glyburide and glipizide), biguanide/glyburide combinations (eg., Glucovance®), thiazolidinediones (e.g., troglitazone, rosiglitazone and pioglitazone), PPAR-alpha agonists, PPAR-gamma agonists, PPAR alpha/gamma dual agonists, SGLT2 inhibitors, glycogen phosphorylase inhibitors, inhibitors of fatty acid binding protein (aP2) such as those disclosed in U.S. Pat. No. 6,548,529 filed Mar. 6, 2000, glucagon-like peptide-1 (GLP-1), and dipeptidyl peptidase IV (DP4) inhibitors.

Examples of suitable anti-osteoporosis agents for use in combination with the compounds of the present invention include alendronate, risedronate, PTH, PTH fragment, raloxifene, calcitonin, steroidal or non-steroidal progesterone receptor agonists, RANK ligand antagonists, calcium sensing receptor antagonists, TRAP inhibitors, selective estrogen receptor modulators (SERM), estrogen and AP-1 inhibitors.

Examples of suitable anti-obesity agents for use in combination with the compounds of the present invention include aP2 inhibitors, such as those disclosed in U.S. Ser. No. 09/519,079 filed Mar. 6, 2000, PPAR gamma antagonists, PPAR delta agonists, beta 3 adrenergic agonists, such as AJ9677 (Takeda/Dainippon), L750355 (Merck), or CP331648 (Pfizer) or other known beta 3 agonists as disclosed in U.S. Pat. Nos. 5,541,204, 5,770,615, 5,491,134, 5,776,983 and 5,488,064, a lipase inhibitor, such as orlistat or ATL-962 (Alizyme), a serotonin (and dopamine) reuptake inhibitor, such as sibutramine, topiramate (Johnson & Johnson) or axokine (Regeneron), a thyroid receptor beta drug, such as a thyroid receptor ligand as disclosed in WO 97/21993 (U. Cal SF), and WO 99/00353 (KaroBio), and/or an anorectic agent, such as dexamphetamine, phentermine, phenylpropanolamine or mazindol.

Examples of suitable anti-inflammatory agents for use in combination with the compounds of the present invention include prednisone, dexamethasone, ENBREL (etanercept), cyclooxygenase inhibitors (i.e., COX-1 and/or COX-2 inhibitors such as NSAIDs, aspirin, indomethacin, ibuprofen, piroxicam, naproxen, CELEBREX (celecoxib), VIOXX (rofecoxib), CTLA4-Ig agonists/antagonists, CD40 ligand antagonists, IMPDH inhibitors, such as mycophenolate (CELLCEPT (myconhenolate mofetil) integrin antagonists, alpha-4 beta-7 integrin antagonists, cell adhesion inhibitors, interferon gamma antagonists, ICAM-1, tumor necrosis factor (TNF) antagonists (e.g., infliximab, OR1384), prostaglandin synthesis inhibitors, budesonide, clofazimine, CNI-1493, CD4 antagonists (e.g., priliximab), p38 mitogen-activated protein kinase inhibitors, protein tyrosine kinase (PTK) inhibitors, IKK inhibitors, and therapies for the treatment of irritable bowel syndrome (e.g., ZELMAC (tegaserod) and maxi-K openers such as those disclosed in U.S. Pat. No. 6,184,231 B1).

Example of suitable anti-anxiety agents for use in combination with the compounds of the present invention include diazepam, lorazepam, buspirone, oxazepam, and hydroxyzine pamoate.

Examples of suitable anti-depressants for use in combination with the compounds of the present invention include citalopram, fluoxetine, nefazodone, sertraline, and paroxetine.

Examples of suitable anti-hypertensive agents for use in combination with the compounds of the present invention include beta adrenergic blockers, calcium channel blockers (L-type and T-type; e.g. diltiazem, verapamil, nifedipine, amlodipine and mybefradil), diuretics (e.g., chlorothiazide, hydrochlorothiazide, flumethiazide, hydroflumethiazide, bendroflumethiazide, methylchlorothiazide, trichloromethiazide, polythiazide, benzthiazide, ethacrynic acid tricrynafen, chlorthalidone, furosemide, musolimine, bumetanide, triamtrenene, amiloride, spironolactone), renin inhibitors, ACE inhibitors (e.g., captopril, zofenopril, fosinopril, enalapril, ceranopril, cilazopril, delapril, pentopril, quinapril, ramipril, lisinopril), AT-1 receptor antagonists (e.g., losartan, irbesartan, valsartan), ET receptor antagonists (e.g., sitaxsentan, atrsentan and compounds disclosed in U.S. Pat. Nos. 5,612,359 and 6,043,265), Dual ET/AII antagonist (e.g., compounds disclosed in WO 00/01389), neutral endopeptidase (NEP) inhibitors, vasopepsidase inhibitors (dual NEP-ACE inhibitors) (e.g., omapatrilat and gemopatrilat), and nitrates.

Examples of suitable anti-platelet agents for use in combination with the compounds of the present invention include GPIIb/IIIa blockers (e.g., abciximab, eptifibatide, tirofiban), P2Y12 antagonists (e.g., clopidogrel, ticlopidine, CS-747), thromboxane receptor antagonists (e.g., ifetroban), aspirin, and PDE-III inhibitors (e.g., dipyridamole) with or without aspirin.

Examples of suitable cardiac glycosides for use in combination with the compounds of the present invention include digitalis and ouabain.

Examples of suitable cholesterol/lipid lowering agents for use in combination with the compounds of the present invention include HMG-CoA reductase inhibitors (e.g., pravastatin, lovastatin, atorvastatin, simvastatin, NK-104 (a.k.a. itavastatin, or nisvastatin or nisbastatin) and ZD-4522 (a.k.a. rosuvastatin, or atavastatin or visastatin)), squalene synthetase inhibitors, fibrates, bile acid sequestrants, ACAT inhibitors, MTP inhibitors, lipooxygenase inhibitors, cholesterol absorption inhibitors, and cholesterol ester transfer protein inhibitors (e.g., CP-529414).

Examples of suitable mineralocorticoid receptor antagonists for use in combination with the compounds of the present invention include spironolactone and eplerinone.

Examples of suitable phospodiesterase inhibitors for use in combination with the compounds of the present invention include PDEIII inhibitors such as cilostazol, and PDE V inhibitors such as sildenafil.

Examples of suitable thyroid mimetics for use in combination with the compounds of the present invention include thyrotropin, polythyroid, KB-130015, and dronedarone.

Examples of suitable anabolic agents for use in combination with the compounds of the present invention include testosterone, TRH diethylstilbesterol, estrogens, β-agonists, theophylline, anabolic steroids, dehydroepiandrosterone, enikephalins, E-series prostagladins, retinoic acid and compounds as disclosed in U.S. Pat. No. 3,239,345, e.g., zeranol; U.S. Pat. No. 4,036,979, e.g., sulbenox or peptides as disclosed in U.S. Pat. No. 4,411,890.

Examples of suitable HIV or AIDS therapies for use in combination with the compounds of the present invention include indinavir sulfate, saquinavir, saquinavir mesylate, ritonavir, lamivudine, zidovudine, lamivudine/zidovudine combinations, zalcitabine, didanosine, stavudine, and megestrol acetate.

Examples of suitable therapies for treatment of Alzheimer's disease and cognitive disorders for use in combination with the compounds of the present invention include donepezil, tacrine, revastigmine, 5HT6, gamma secretase inhibitors, beta secretase inhibitors, SK channel blockers, Maxi-K blockers, and KCNQs blockers.

Examples of suitable therapies for treatment of sleeping disorders for use in combination with the compounds of the present invention include melatonin analogs, melatonin receptor antagonists, ML1B agonists, and GABA/NMDA receptor antagonists.

Examples of suitable anti-proliferative agents for use in combination with the compounds of the present invention include cyclosporin A, paclitaxel, FK 506, and adriamycin.

Examples of suitable anti-tumor agents for use in combination with the compounds of the present invention include paclitaxel, adriamycin, epothilones, cisplatin and carboplatin.

Compounds of the present invention can further be used in combination with nutritional supplements such as those described in U.S. Pat. No. 5,179,080, especially in combination with whey protein or casin, amino acids (such as leucine, branched amino acids and hydroxymethylbutyrate), triglycerides, vitamins (e.g., A, B6, B12, folate, C, D and E), minerals (e.g., selenium, magnesium, zinc, chromium, calcium and potassium), carnitine, lipoic acid, creatine, and coenzyme Q-10.

In addition, compounds of the present invention can be used in combination with therapeutic agents used in the treatment of sexual dysfunction, including but not limited to PDE5 inhibitors, such as sildenafil or IC-351; with an antiresorptive agent, hormone replacement therapies, vitamin D analogues, calcitonins, elemental calcium and calcium supplements, cathepsin K inhibitors, MMP inhibitors, vitronectin receptor antagonists, Src $SH_2$ antagonists, vacular —$H^+$— ATPase inhibitors, progesterone receptor agonists, ipriflavone, fluoride, RANK antagonists, PTH and its analogues and fragments, Tibolone, HMG-CoA reductase inhibitors, SERM's, p38 inhibitors, prostanoids, 17-beta hydroxysteroid dehydrogenase inhibitors and Src kinase inhibitors.

Compounds of the present invention can be used in combination with male contraceptives, such as nonoxynol 9 or therapeutic agents for the treatment of hair loss, such as minoxidil and finasteride or chemotherapeutic agents, such as with LHRH agonists.

For their preferred anticancer or antiangiogenic use, the compounds of the present invention can be administered either alone or in combination with other anti-cancer and cytotoxic agents and treatments useful in the treatment of cancer or other proliferative diseases, for example, where the second drug has the same or different mechanism of action than the present compounds of formula I. Examples of classes of anti-cancer and cytotoxic agents useful in combination with the present compounds include but are not limited to: alkylating agents such as nitrogen mustards, alkyl sulfonates, nitrosoureas, ethylenimines, and triazenes; antimetabolites such as folate antagonists, purine analogues, and pyrimidine analogues; antibiotics such as anthracyclines, bleomycins, mitomycin, dactinomycin, and plicamycin; enzymes such as L-asparaginase; farnesyl-protein transferase inhibitors; 5α reductase inhibitors; inhibitors of 17β-hydroxy steroid dehydrogenase type 3; hormonal agents such as glucocorticoids, estrogens/antiestrogens, androgens/antiandrogens, progestins, and luteinizing hormone-releasing hormone antagonists, octreotide acetate; microtubule-disruptor agents, such as ecteinascidins or their analogs and derivatives; microtubule-stabilizing agents such as taxanes, for example, paclitaxel (TAXOL), docetaxel (TAXOTERE), and their analogs, and epothilones, such as epothilones A-F and their analogs; plant-derived products, such as vinca alkaloids, epipodophyllotoxins, taxanes; and topiosomerase inhibitors; prenyl-protein transferase inhibitors; and miscellaneous agents such as hydroxyurea, procarbazine, mitotane, hexamethylmelamine, platinum coordination complexes such as cisplatin and carboplatin; and other agents used as anti-cancer and cytotoxic agents such as biological response modifiers, growth factors; immune modulators and monoclonal antibodies. The compounds of the invention may also be used in conjunction with radiation therapy.

Representative examples of these classes of anti-cancer and cytotoxic agents include but are not limited to mechlorethamine hydrochloride, cyclophosphamide, chlorambucil, melphalan, ifosfamide, busulfan, carmustin, lomustine, semustine, streptozocin, thiotepa, dacarbazine, methotrexate, thioguanine, mercaptopurine, fludarabine, pentastatin, cladribin, cytarabine, fluorouracil, doxorubicin hydrochloride, daunorubicin, idarubicin, bleomycin sulfate, mitomycin C, actinomycin D, safracins, saframycins, quinocarcins, discodermolides, vincristine, vinblastine, vinorelbine tartrate, etoposide, etoposide phosphate, teniposide, paclitaxel, tamoxifen, estramustine, estramustine phosphate sodium, flutamide, buserelin, leuprolide, pteridines, diyneses, levamisole, aflacon, interferon, interleukins, aldesleukin, filgrastim, sargramostim, rituximab, BCG, tretinoin, irinotecan hydrochloride, betamethosone, gemcitabine hydrochloride, altretamine, and topoteca and any analogs or derivatives thereof.

Preferred member of these classes include, but are not limited to, paclitaxel, cisplatin, carboplatin, doxorubicin, carminomycin, daunorubicin, aminopterin, methotrexate, methopterin, mitomycin C, ecteinascidin 743, or porfiromycin, 5-fluorouracil, 6-mercaptopurine, gemcitabine, cytosine arabinoside, podophyllotoxin or podophyllotoxin derivatives such as etoposide, etoposide phosphate or teniposide, melphalan, vinblastine, vincristine, leurosidine, vindesine and leurosine.

Examples of anticancer and other cytotoxic agents include the following: epothilone derivatives as found in German Patent No. 4138042.8; WO 97/19086, WO 98/22461, WO 98/25929, WO 98/38192, WO 99/01124, WO 99/02224, WO 99/02514, WO 99/03848, WO 99/07692, WO 99/27890, WO 99/28324, WO 99/43653, WO 99/54330, WO 99/54318, WO 99/54319, WO 99/65913, WO 99/67252, WO 99/67253 and WO 00/00485; cyclin dependent kinase inhibitors as found in WO 99/24416 (see also U.S. Pat. No. 6,040,321); and prenyl-protein transferase inhibitors as found in WO 97/30992 and WO 98/54966; and agents such as those described generically and specifically in U.S. Pat. No. 6,011,029 (the compounds of which U.S. Patent can be employed together with any NHR (nuclear hormone receptor) modulators such as AR (androgen receptor) modulators, ER (estrogen receptor) modulators, with LHRH modulators, or with surgical castration, especially in the treatment of cancer).

The combinations of the present invention can also be formulated or co-administered with other therapeutic agents that are selected for their particular usefulness in administering therapies associated with the aforementioned conditions. For example, the compounds of the invention may be formulated with agents to prevent nausea, hypersensitivity and gastric irritation, such as antiemetics, and $H_1$ and $H_2$ antihistaminics.

As it pertains to the treatment of cancer, the compounds of this invention are most preferably used alone or in combination with anti-cancer treatments such as radiation therapy and/or with cytostatic and/or cytotoxic agents, such as, but not limited to, DNA interactive agents, such as cisplatin or doxorubicin; inhibitors of farnesyl protein transferase, such as those described in U.S. Pat. No. 6,011,029; topoisomerase II inhibitors, such as etoposide; topoisomerase I inhibitors, such as CPT-11 or topotecan; tubulin stabilizing agents, such as paclitaxel, docetaxel, other taxanes, or epothilones; hormonal agents, such as tamoxifen; thymidilate synthase inhibitors, such as 5-fluorouracil; antimetabolites, such as methoxtrexate; antiangiogenic agents, such as angiostatin, ZD6474, ZD6126 and comberstatin A2; kinase inhibitors, such as her2 specific antibodies, Iressa and CDK inhibitors; histone deacetylase inhibitors, such as CI-994 and MS-27-275. Such compounds may also be combined with agents which suppress the production of circulating testosterone such as LHRH agonists or antagonists or with surgical castration.

For example, known therapies for advanced metastatic prostate cancer include "complete androgen ablation therapy" wherein tumor growth is inhibited by controlling the supply of androgen to the prostate tissues via chemical castration (castration serves to inhibit the production of circulating testosterone (T) and dihydrotestosterone (DHT)) followed by the administration of androgen receptor (AR) antagonists (which inhibit the function T/DHT derived from the conversion of circulating androgen precursors to T/DHT by the prostate tissue). The compounds of the present invention can be employed as AR antagonists in complete ablation therapy, alone or in combination with other AR antagonists such as Flutamide, Casodex, Nilutamide, or Cyproterone acetate.

Another application of the present compounds is in combination with antibody therapy such as but not limited to antibody therapy against PSCA. An additional application is in concert with vaccine/immune modulating agents for the treatment of cancer.

Compounds of the present invention can be employed in accordance with the methods described in U.S. Pat. No. 6,960,474, entitled "Selective Androgen Receptor Modulators and Methods for their Identification, Design and Use" filed Jun. 20, 2001 which Patent is incorporated herein by reference in its entirety; U.S. Patent Application Publication No. US 2004/0176324 A1, entitled "Fused Heterocyclic Succinimide Compounds and Analogs Thereof, Modulators of Nuclear Hormone Receptor Function" filed Jun. 20, 2001 which Patent Application Publication is incorporated herein by reference in its entirety; and U.S. Patent Application Ser. No. 09/885,798, now abandoned, entitled "Fused Cyclic Modulators of Nuclear Hormone Receptor Function" filed Jun. 20, 2001, which Patent Application is incorporated herein by reference in its entirety (including, but not limited to, reference to all specific compounds within formula I of the present invention).

The above other therapeutic agents, when employed in combination with the compounds of the present invention, can be used, for example, in those amounts indicated in the Physicians' Desk Reference (PDR) or as otherwise determined by one of ordinary skill in the art.

The following assays can be employed in ascertaining the activity of a compound as a 17β-HSD3 inhibitor. Various compounds of the present invention were determined to have 17β-HSD3 inhibition activity utilizing the enzymatic and transactivation assays as described below.

ASSAYS

17β-HSD3 enzymatic activity and its inhibition through various compounds were determined in cell extracts using a scintillation proximity assay (SPA) or within cells using a 17β-HSD3 driven secreted alkaline phosphatase (SEAP) reporter assay. In the 17β-HSD3 SPA assay, 17β-HSD3 enzyme was prepared from HEK293 cells, a human kidney epithelial cell line that does not express endogenous 17β-HSD3 protein, engineered to over express a cDNA clone encoding full length human 17β-HSD3. Stable clonal populations of HEK293 cells expressing 17β-HSD3 were established upon antibiotic selection with G418 (500 μg/ml). Individual 17β-HSD3 HEK293 transfectants were analyzed by Western blotting for 17β-HSD3 protein levels and assay for androstenedione to testosterone conversion activity. Clonal populations with significant 17β-HSD3 activity were expanded and cellular lysates were prepared by homogenization followed by high-speed centrifugation for use in the 17β-HSD3 SPA.

The inhibitory activity of compounds was first evaluated in the 17β-HSD3 SPA format. Briefly, HEK293 lysates containing recombinant 17β-HSD3 were incubated with {3H} androstenedione for 60 minutes with gentle rocking in the presence or absence of compound (up to 30 μM) in a total volume of 30 μl. The enzymatic reaction of 17β-HSD3 was terminated by the addition of 10 μl of 0.1 N HCL. The {3H}-testosterone converted by 17β-HSD3 was captured and quantified using a monoclonal antibody against testosterone that was pre-conjugated to anti-mouse IgG Yttrium silicate SPA beads.

A 17β-HSD3-driven cell based assay was established using MB-MDA231 cells and an androgen-responsive gene promoter reporter construct. In this assay, 17β-HSD3 converted testosterone is monitored by the transcriptional activity of the endogenous androgen receptor through the introduction of androgen responsive prostate specific antigen (PSA) promoter. To set up this system, MB-MDA231, which do not express 17β-HSD3, were transfected with human 17β-HSD3 and clonal populations were selected and analyzed as described above. Clonal cell lines showing moderate androstenedione to testosterone conversion activity by thin layer chromatography (TLC) analysis were used to determine the inhibitory activity of compounds. 17β-HSD3-MB-MDA-231 transfectants were transfected with a PSA SEAP reporter and grown in cell culture overnight. The PSA promoter contains several androgen receptor-binding elements which are sufficient to drive an androgen responsive transcriptional response. The following day, 17β-HSD3 transfectants containing the PSA-SEAP promoter were incubated with 10 nM androstenedione in the presence or absence of compound for 18 hours. Cellular media was harvested and analyzed for alkaline phosphatase activity by standard methods.

EXAMPLES

Abbreviations

The following abbreviations are used herein.
Ac Acetyl
AcOH Acetic acid
aq. Aqueous
$BH_3 \cdot DMS$ Borane-dimethyl sulfide complex
BINAP 2,2'-bis(diphenylphosphino)-1,1'-binaphthylbenzyl
Bn Benzyl
Boc tert-Butoxycarbonyl
BOP Benzotriazol-1-yloxytris(dimethylamino)phosphonium hexaflurophosphate
n-BuOH n-Butanol
CDI Carbonyldiimidazole
DIEA N,N-Diisopropyl ethylamine
DMAP Dimethylaminopyridine
DMF Dimethylformamide
DMSO Dimethylsulfoxide
EDCI 1-(3-Dimethylaminopropyl)-3-ethylcarbodiimide hydrochloride
Et Ethyl
$Et_2O$ Ether
EtOAc Ethyl acetate
EtOH Ethanol
h Hours
HOBt 1-Hydroxybenzotriazole
HPLC High pressure liquid chromatography
i iso
LC/MS High performance liquid chromatography/mass spectrometry
LDA Lithium diisopropylamide
mCPBA 3-Chloroperoxybenzoic acid
Me Methyl
MeI Methyl iodide
MeOH Methanol
min. Minutes
m/z Mass spectrometry
n Normal
Pd/C Palladium on carbon
Ph Phenyl
Prep HPLC Preparative reverse phase HPLC
p-TsOH para-Toluenesulonic acid
Rh/C Rhodium on carbon
$R_t$ Retention time
rt or RT Room temperature
sat. Saturated
Tf trifluoromethanesulfonyl
TFA Trifluoroacetic acid
THF Tetrahydrofuran
YMC YMC Inc, Wilmington, N.C. 28403
HPLC condition: YMC S5 ODS column 4.6×50 mm, 10-90% aqueous methanol over 4 minutes containing 0.2% $H_3PO_4$, 3 ml/min, monitoring at 220 nm. This is the default HPLC condition unless otherwise noticed.
HPLC condition (a): YMC S5 ODS column 4.6×50 mm, 50-90% aqueous methanol over 2 minutes containing 0.2% $H_3PO_4$, 3 ml/min, monitoring at 220 nm.
HPLC condition: (b): YMC S5 ODS column 4.6×50 mm, 10-90% aqueous methanol over 2 minutes containing 0.2% $H_3PO_4$, 3 ml/min, monitoring at 220 nm.

Compounds prepared are referred to in places herein by the step with which they are prepared. For example, the compound prepared in step 2A is referred to herein as "2A." The title compound of an Example can be referred to by the Example number (e.g., "Example 64").

Example 1

6-Acetyl-2-chloro-3-fluoro-5,6-dihydro-pyrido[3,2-c][1]benzazocine

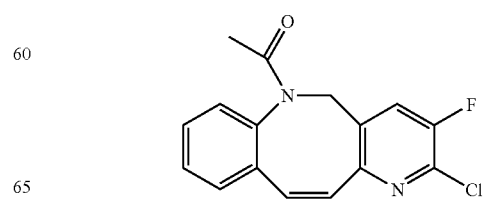

1A. Preparation of (2,6-dichloro-5-fluoro-pyridin-3-yl)-methanol

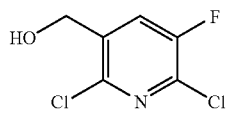

To a stirred mixture of 2,6-dichloro-5-fluoro-nicotinic acid (1.0 g, 4.76 mmol) in dry THF (50 mL) under argon was added neat BH$_3$.DMS (1.35 mL, 14.29 mmol) dropwise. The resulting mixture was heated to reflux for 3 hours, cooled to room temperature and quenched by the dropwise addition of water (4 mL). The reaction mixture was concentrated in vacuo. The crude alcohol was diluted with EtOAc, washed with 1N NaOH, 1N HCl, saturated aqueous NaHCO$_3$ solution and brine. The EtOAc layer was dried (MgSO$_4$), filtered and concentrated in vacuo to give 1A (0.93 g, 97%). HPLC R$_t$=1.79 min (Column: YMC ODS-A 4.6×50 mm (4 min.); Solvent A=10% MeOH, 90% H$_2$O, 0.1% TFA; Solvent B=90% MeOH, 10% H$_2$O, 0.1% TFA); LCMS Found: (M+H)$^+$=210.

1B. Preparation of 3-bromomethyl-2,6-dichloro-5-fluoro-pyridine

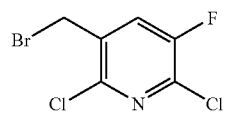

To a stirred mixture of alcohol 1A (3.52 g, 17.9 mmol) in CHCl$_3$ (100 mL) under argon was added 1M PBr$_3$ in CH$_2$Cl$_2$ (18.0 mL, 18.0 mmol). The reaction mixture was heated to reflux for 15 minutes, cooled to room temperature, then poured into a mixture of ice and saturated NaHCO$_3$ solution (200 mL). The pH was adjusted to basic by addition of solid NaHCO$_3$. The aqueous layer was extracted with EtOAc. The combined EtOAc extracts were washed with brine. The organic layer was dried (MgSO$_4$), filtered and concentrated in vacuo to give 1B (4.11 g, 88%). HPLC R$_t$=2.78 min. (Column: YMC ODS-A 4.6×50 mm (4 min.); Solvent A=10% MeOH, 90% H$_2$O, 0.1% TFA; Solvent B=90% MeOH, 10% H$_2$O, 0.1% TFA).

aa. Preparation of N-(2-bromo-phenyl)-acetamide

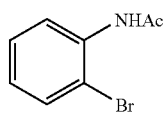

A solution of 2-bromoaniline (22.0 g, 12.8 mmol), acetic anhydride (13.06 g, 12.8 mmol) and a catalytic amount of DMAP in CH$_2$Cl$_2$ (100 mL) was stirred at 0° C. The mixture was slowly warmed to room temperature and stirred overnight. The reaction mixture was washed with saturated aqueous NaHCO$_3$ solution and concentrated. The residue was triturated with hexanes/CH$_2$Cl$_2$, the solid was filtered and rinsed with hexanes to give aa (25.4 g, 92.8%). HPLC R$_t$=1.523 min.

bb. Preparation of N-(2-Vinyl-phenyl)-acetamide

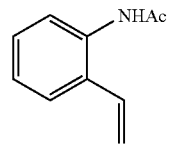

A mixture of aa (2.0 g, 9.34 mmol), tributylvinyl stannane (3.55 mL, 12.15 mmol) and Pd(PPh$_3$)$_2$Cl$_2$ (1.64 g, 2.335 mmol) in toluene was heated at 95° C. under nitrogen after degassing. After 1 hour, the reaction mixture was concentrated and purified by flash chromatography (SiO$_2$, 100% CH$_2$Cl$_2$ to 50% EtOAc/CH$_2$CL$_2$) followed by recrystalization from EtOH/H$_2$O to give bb (732 mg, 49%). HPLC R$_t$=1.45 min.

1C. Preparation of N-(2,6-dichloro-5-fluoro-pyridin-3-ylmethyl)-N-(2-vinyl-phenyl)-acetamide

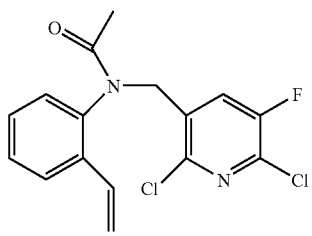

To a stirred mixture of 1B (0.5 g, 1.93 mmol) and N-(2-vinyl-phenyl)-acetamide bb (0.314 g, 1.95 mmol) in DMF (5 mL) was added NaH (47 mg, 1.95 mmol) at 0° C. The reaction mixture was stirred for 30 minutes at room temperature, then poured into H$_2$O (50 mL) and extracted with Et$_2$O (20 mL). The Et$_2$O layer was washed with H$_2$O (2×20 mL), dried (MgSO$_4$), filtered and concentrated in vacuo to give 1C (0.63 g, 96%). HPLC R$_t$=3.212 min. (Column: YMC ODS-A 4.6×50 mm (4 min.); Solvent A=10% MeOH, 90% H$_2$O, 0.1% TFA; Solvent B=90% MeOH, 10% H$_2$O, 0.1% TFA).

1D. Preparation of 6-Acetyl-2-chloro-3-fluoro-5,6-dihydro-pyrido[3,2-c][1]benzazocine

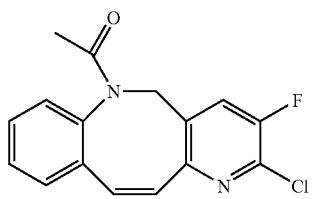

To a stirred solution of 1C (0.63 g, 1.85 mmol) and Et$_3$N (0.78 mL, 5.55 mmol) in DMF (15 mL) was added PdCl$_2$ (49 mg, 0.28 mmol) and the reaction was heated to 120° C. When the reaction was complete by HPLC, the mixture was poured into H$_2$O and extracted with Et$_2$O. The Et$_2$O layer was washed with H$_2$O (2×20 mL) and brine (20 mL), dried (MgSO$_4$), filtered and concentrated in vacuo. The residue obtained was purified by flash chromatography (SiO$_2$, 100% CH$_2$Cl$_2$ to 10% EtOAc/CH$_2$Cl$_2$) to give 1D (0.12 g, 21%). HPLC R$_t$=2.77 min. (Column: YMC ODS-A 4.6×50 mm (4 min.); Solvent A=10% MeOH, 90% H$_2$O, 0.1% TFA; Solvent B=90% MeOH, 10% H$_2$O, 0.1% TFA); LCMS Found: (M+H)$^+$=303.

Example 2

6-Acetyl-3-fluoro-5,6-dihydro-2-(6-methoxy-3-pyridinyl)-pyrido[3,2-c][1]benzazocine

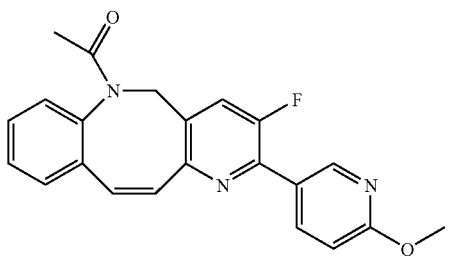

2A. Preparation of 2-methoxy-5-(4,4,5,5-tetramethyl-[1,3,2]dioxaborolan-2-yl)-pyridine

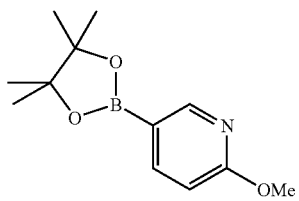

To a solution of 5-bromo-2-methoxy-pyridine (1.453 g, 7.73 mmol) in THF (50 mL) at −78° C. under N$_2$ was added n-BuLi (3.4 mL, 2.5 M in hexanes, 8.5 mmol) dropwise. The mixture was stirred at −78° C. for 30 minutes, then 2-isopropoxy-4,4,5,5-tetramethyl-[1,3,2]dioxaborolane (2.4 mL, 11.60 mmol) was added. The reaction mixture was warmed to room temperature for 1 hour, then poured into water and extracted with EtOAc. The combined extracts were washed with water and brine, dried (MgSO$_4$), filtered and concentrated to give 2A (1.221 g, 67.5%) as a colorless oil.

2B. Preparation of 6-Acetyl-3-fluoro-5,6-dihydro-2-(6-methoxy-3-pyridinyl)-pyrido[3,2-c][1]benzazocine

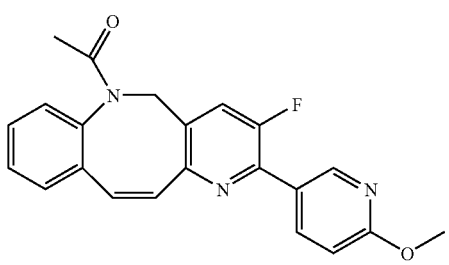

To a solution of 1D (20 mg, 0.066 mmol) in toluene (0.5 mL) and EtOH (0.3 mL) was added a 2M aqueous solution of Na$_2$CO$_3$ (0.3 mL, 0.6 mmol). The resulting solution was purged with argon for 30 minutes and 2A (23.3 mg, 0.099 mmol) was added, followed by a catalytic amount of Pd(PPh$_3$)$_4$. The reaction was heated to 100° C. for 15 minutes, then cooled to ambient temperature. EtOAc and H$_2$O were added, the layers were separated and the organic phase was washed with saturated aqueous NaHCO$_3$ solution, dried (Na$_2$SO$_4$), filtered and concentrated. The residue was purified by flash chromatography (SiO$_2$, 100% CH$_2$Cl$_2$ then 100% EtOAc) to afford 2B (23.7 mg, 96%). HPLC R$_t$=3.182 min; LCMS Found: (M+H)$^+$=376.

Example 3

6-Acetyl-3-fluoro-5,6,11,12-tetrahydro-2-(6-methoxy-3-pyridinyl)-pyrido[3,2-c][1]benzazocine

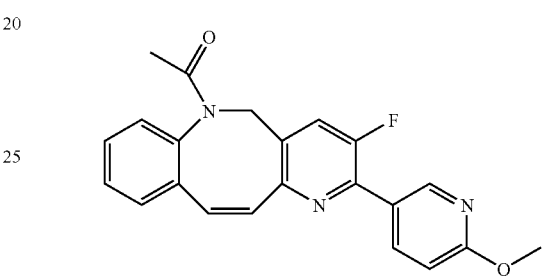

To a solution of compound 2B (13.6 mg, 0.036 mmol) in MeOH (5 mL) was added 10% Pd/C (3 mg) and the mixture was stirred under a balloon filled with hydrogen for 1 hour. The reaction was filtered through a 0.45 micron filter membrane and concentrated in vacuo to give the title compound (13.6 mg, 100%). HPLC R$_t$=2.996 min. (Column: YMC ODS-A 4.6×50 mm (4 min.); Solvent A=10% MeOH, 90% H$_2$O, 0.1% TFA; Solvent B=90% MeOH, 10% H$_2$O, 0.1% TFA); LCMS Found: (M+H)$^+$=378.

Example 4

6-Acetyl-3-fluoro-5,6-dihydro-2-phenylpyrido[3,2-c][1]benzazocine

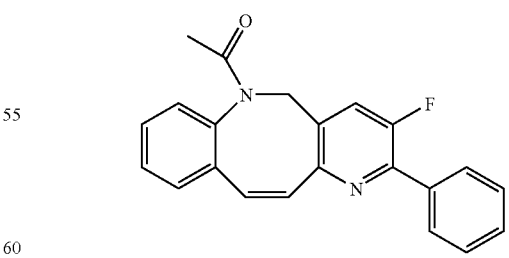

The title compound (20.1 mg, 88.5%) was prepared from 1D (20.0 mg, 0.066 mmol) and phenylboronic acid (12.1 mg, 0.099 mmol) by a route analogous to that used for the preparation of 2B. HPLC R$_t$=3.326 min; LCMS Found: (M+H)$^+$=345.

Example 5

6-Acetyl-3-fluoro-5,6-dihydro-2-[6-(4-morpholinyl)-3-pyridinyl]pyrido[3,2-c][1]benzazocine

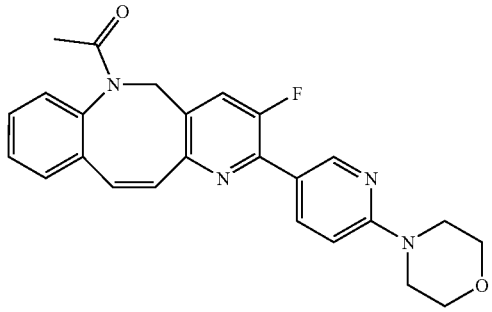

5A. Preparation of 4-[5-(4,4,5,5-tetramethyl-[1,3,2]dioxaborolan-2-yl)-pyridin-2-yl]-morpholine

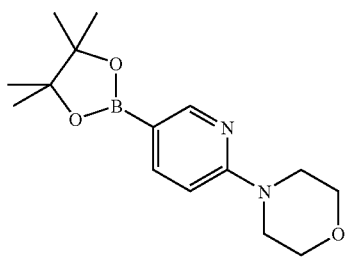

Compound 5A (616 mg, 71%) was prepared from 4-(5-bromo-pyridin-2-yl)-morpholine (727 mg, 2.99 mmol) and 2-isopropoxy-4,4,5,5-tetramethyl-[1,3,2]dioxaborolane (0.915 mL, 4.49 mmol) by a route analogous to that used for the preparation of 2A.

5B. Preparation of 6-Acetyl-3-fluoro-5,6-dihydro-2-[6-(4-morpholinyl)-3-pyridinyl]pyrido[3,2-c][1]benzazocine

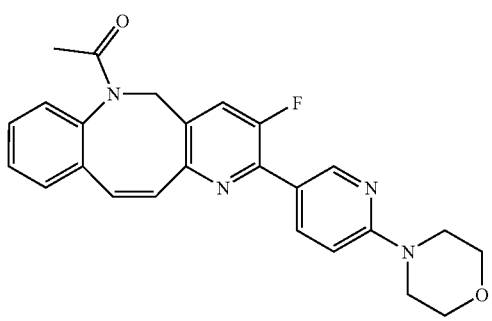

Compound 5B (20.5 mg, 72.2%) was prepared from 1D (20.0 mg, 0.066 mmol) and 5A (28.7 mg, 0.099 mmol) by a route analogous to that used for the preparation of 2B. HPLC $R_t$=2.336 min; LCMS Found: (M+H)$^+$=431.

Example 6

6-Acetyl-2,8-dichloro-3-fluoro-5,6-dihydropyrido[3,2-c][1]benzazocine

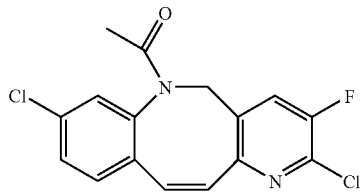

6A. Preparation of 2-bromo-5-chloro-phenylamine

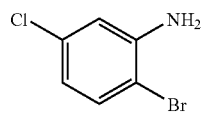

A mixture of 1-bromo-4-chloro-2-nitro-benzene (10.0 g, 42.3 mmol) and SnCl$_2$ (24.0 g, 127 mmol) in EtOAc (100 mL) was heated to reflux for 1 hour. After cooling to room temperature, water and NaHCO$_3$ were added slowly at 0° C. until the reaction was basic. The mixture was filtered through celite and rinsed with EtOAc. The filtrate was washed with aqueous NaHCO$_3$ solution and brine, dried (MgSO$_4$), filtered and concentrated to give 6A (8.7 g, 100%) as black crystals. $R_t$=2.489 min.

6B. Preparation of N-(2-bromo-5-chloro-phenyl)-acetamide

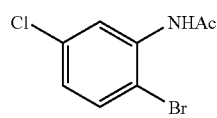

Compound 6B (8.48 g, 80.7%) was prepared from 6A (8.7 g, 42.3 mmol) by a route analogous to that used for the preparation of aa. $R_t$=2.093 min.

6C. Preparation of N-(5-chloro-2-vinyl-phenyl)-acetamide

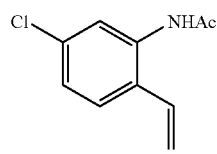

Compound 6C (1.97 g, 62.7%) was prepared from 6B (4.0 g, 16.1 mmol) by a route analogous to that used for the preparation of bb.

6D. Preparation of 6-Acetyl-2,8-dichloro-3-fluoro-5,6-dihydropyrido[3,2-c][1]benzazocine

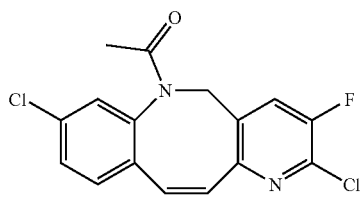

Compound 6D was prepared from 6C and 1B in two steps by a route analogous to that used for the preparation of 1D. HPLC $R_t$=3.032 min; LCMS Found: (M+H)$^+$=337.

Example 7

6-Acetyl-8-chloro-3-fluoro-5,6-dihydro-2-(6-methoxy-3-pyridinyl) pyrido[3,2-c][1]benzazocine

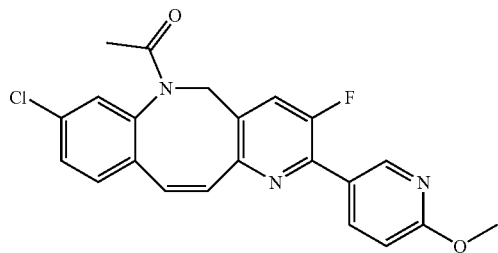

The title compound was prepared from 6D and 2A by a route analogous to that used for the preparation of 2B. HPLC $R_t$=3.412 min; LCMS Found: (M+H)$^+$=410.

Example 8

6-Acetyl-8-chloro-3-fluoro-5,6-dihydro-2-[6-(4-morpholinyl)-3-pyridinyl]pyrido[3,2-c][1]benzazocine

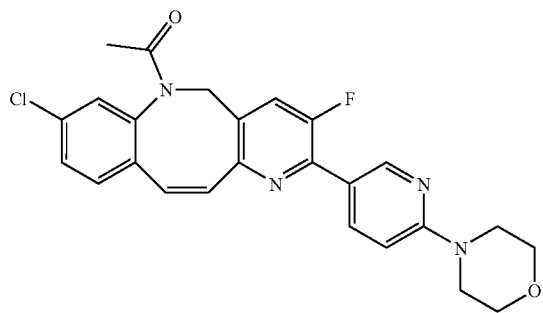

The title compound (16.6 mg, 52%) was prepared from 6D (23.2 mg, 0.0688 mmol) and 5A (22 mg, 0.0722 mmol) by a route analogous to that used for the preparation of 2B. HPLC $R_t$=2.612 min; LCMS Found: (M+H)$^+$=465.

Example 9

6-Acetyl-2,9-dichloro-3-fluoro-5,6-dihydropyrido[3,2-c][1]benzazocine

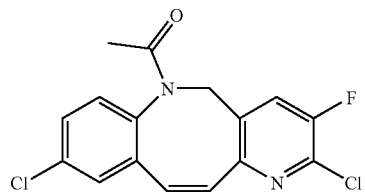

9A. Preparation of N-(2-bromo-4-chloro-phenyl)-acetamide

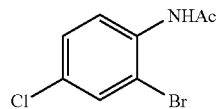

Compound 9A (5.2 g, 86.4%) was prepared from 2-bromo-4-chloro-phenylamine (5.0 g, 24.2 mmol) by a route analogous to that used for the preparation of aa. $R_t$=2.266 min.

9B. Preparation of N-(4-chloro-2-vinyl-phenyl)-acetamide

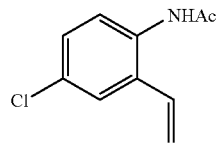

Compound 9B (1.0 g, 64%) was prepared from 9A (2.0 g, 8.05 mmol) by a route analogous to that used for the preparation of bb. HPLC $R_t$=2.169 min.

9C. Preparation of 6-Acetyl-2,9-dichloro-3-fluoro-5,6-dihydropyrido[3,2-c][1]benzazocine

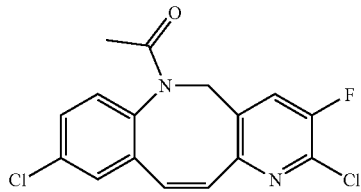

Compound 9C was prepared from 9B and 1B by a route analogous to that used for the preparation of 1D. HPLC $R_t$=3.146 min; LCMS Found: (M+H)$^+$=337.

Example 10

6-Acetyl-9-chloro-3-fluoro-5,6-dihydro-2-(6-methoxy-3-pyridinyl) pyrido[3,2-c][1]benzazocine

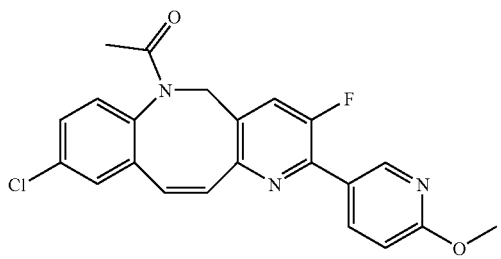

The title compound was prepared from 9C and 2A by a route analogous to that used for the preparation of 2B. HPLC $R_t$=3.496 min; LCMS Found: (M+H)$^+$=410.

Example 11

6-Acetyl-9-chloro-3-fluoro-5,6-dihydro-2-[6-(4-morpholinyl)-3-pyridinyl]pyrido[3,2-c][1]benzazocine

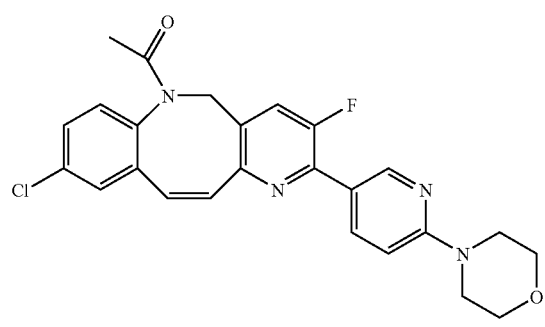

The title compound (21.6 mg, 64.3%) was prepared from 9C (24.4 mg, 0.072 mmol) and 5A (22 mg, 0.072 mmol) by a route analogous to that used for the preparation of 2B. HPLC $R_t$=2.649 min; LCMS Found: $(M+H)^+$=465.

Example 12

6-Acetyl-5,6-dihydropyrido[3,2-c][1]benzazocine

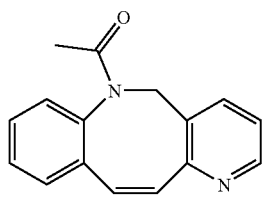

12A. Preparation of (2-chloro-pyridin-3-yl)-methanol

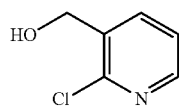

Compound 12A (0.20 g, 44%) was prepared from 2-chloro-nicotinic acid (0.5 g, 3.17 mmol) using a procedure similar to the synthesis of 1A. HPLC $R_t$=0.77 min.

12B. Preparation of 3-bromomethyl-2-chloro-pyridine

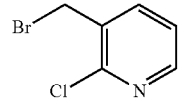

Compound 12B (0.22 g, 78%) was prepared from 12A (0.20 g, 1.39 mmol) using a procedure similar to the synthesis of 1B. HPLC $R_t$=1.94 min.

12C. Preparation of 6-Acetyl-5,6-dihydropyrido[3,2-c][1]benzazocine

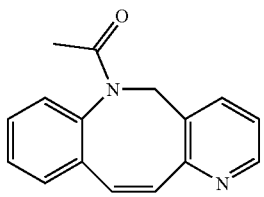

Compound 12C was prepared from bb and 12B by a route analogous to that used for the preparation of 1D. HPLC $R_t$=1.326 min; LCMS Found: $(M+H)^+$=251.

Example 13

6-Acetyl-2-chloro-5,6-dihydropyrido[3,2-c][1]benzazocine

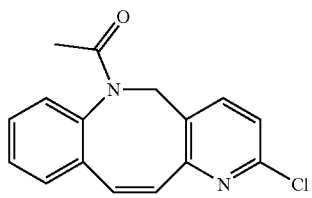

13A. Preparation of (2,6-dichloro-pyridin-3-yl)-methanol

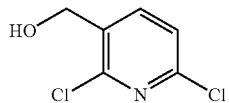

Compound 13A (0.82 g, 89%) was prepared from 2,6-dichloro-nicotinic acid (1.0 g, 5.2 mmol) using a procedure similar to the synthesis of 1A. HPLC $R_t$=1.39 min.

13B. Preparation of 3-bromomethyl-2,6-dichloro-pyridine

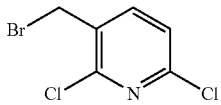

Compound 13B (0.88 g, 80%) was prepared from 13A (0.82 g, 4.6 mmol) using a procedure similar to the synthesis of 1B. HPLC $R_t$=2.44 min.

13C. Preparation of 6-Acetyl-2-chloro-5,6-dihydropyrido[3,2-c][1]benzazocine

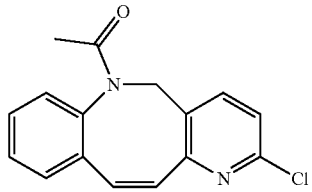

Compound 13C was prepared from bb and 13B by a route analogous to that used for the preparation of 1D. HPLC $R_t$=2.493 min; LCMS Found: $(M+H)^+$=285.

Example 14

6-Acetyl-5,6-dihydro-2-phenylpyrido[3,2-c][1]benzazocine

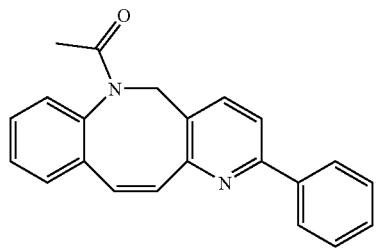

The title compound (19.9 mg, 87%) was prepared from 13C (20.0 mg, 0.07 mmol) and phenylboronic acid (12.8 mg, 0.105 mmol) by a route analogous to that used for the preparation of 2B. HPLC $R_t$=2.353 min; LCMS Found: $(M+H)^+$=327.

Example 15

6-Acetyl-5,6-dihydro-2-(6-methoxy-3-pyridinyl)pyrido[3,2-c][1]benzazocine

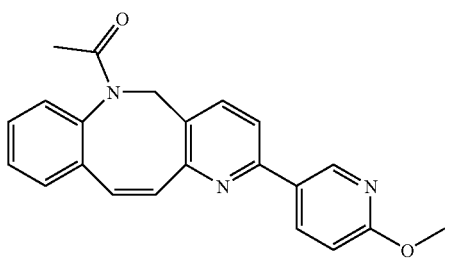

The title compound (14.8 mg, 59%) was prepared from 13C (20.0 mg, 0.07 mmol) and 2A (24.7 mg, 0.105 mmol) by a route analogous to that used for the preparation of 2B. HPLC $R_t$=2.612 min; LCMS Found: $(M+H)^+$=358.

Example 16

6-Acetyl-5,6-dihydro-2-[6-(4-morpholinyl)-3-pyridinyl]pyrido[3,2-c][1]benzazocine

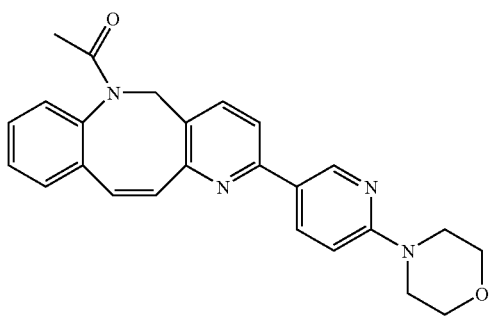

The title compound (26.2 mg, 91%) was prepared from 13C (20.0 mg, 0.07 mmol) and 5A (30.5 mg, 0.105 mmol) by a route analogous to that used for the preparation of 2B. HPLC $R_t$=2.159 min; LCMS Found: $(M+H)^+$=413.

Example 17

6-Acetyl-2,8-dichloro-5,6-dihydropyrido[3,2-c][1]benzazocine

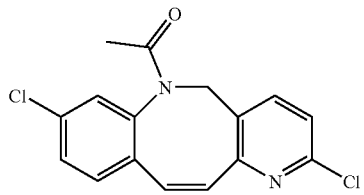

The title compound was prepared from 6C and 13B by a route analogous to that used for the preparation of 1D. HPLC $R_t$=2.769 min; LCMS Found: $(M+H)^+$=319.

Example 18

6-Acetyl-8-chloro-5,6-dihydro-2-(6-methoxy-3-pyridinyl)pyrido[3,2-c][1]benzazocine

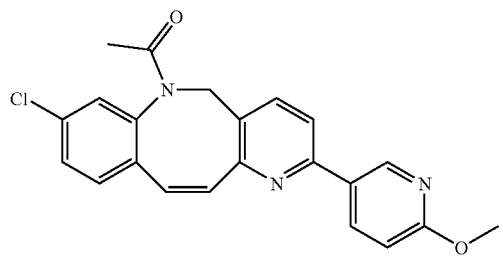

The title compound was prepared from Example 17 and 2A by a route analogous to that used for the preparation of 2B. HPLC $R_t$=2.962 min; LCMS Found: $(M+H)^+$=392.

Example 19

6-Acetyl-2,9-dichloro-5,6-dihydropyrido[3,2-c][1]benzazocine

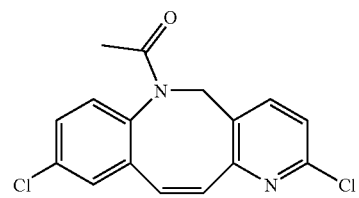

The title compound was prepared from 9B and 13B by a route analogous to that used for the preparation of 1D. HPLC $R_t$=2.842 min; LCMS Found: $(M+H)^+$=319.

Example 20

6-Acetyl-9-chloro-5,6-dihydro-2-(6-methoxy-3-pyridinyl)pyrido[3,2-c][1]benzazocine

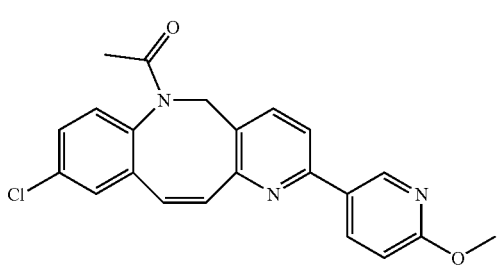

The title compound was prepared from Example 19 and 2A by a route analogous to that used for the preparation of 2B. HPLC $R_t$=3.112 min; LCMS Found: (M+H)$^+$=392.

Example 21

6-Acetyl-3-fluoro-5,6-dihydro-2,8-bis(6-methoxy-3-pyridinyl)pyrido[3,2-c][1]benzazocine

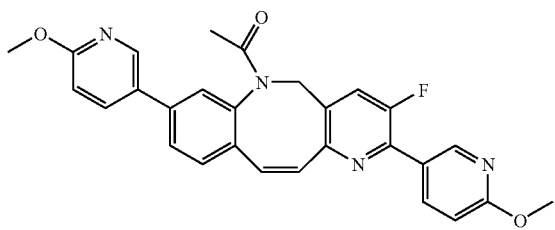

The title compound was obtained as a by-product during the preparation of Example 7. HPLC $R_t$=3.582 min; LCMS Found: (M+H)$^+$=483.

Example 22

6-Acetyl-5,6-dihydro-2,8-bis(6-methoxy-3-pyridinyl)pyrido[3,2-c][1]benzazocine.

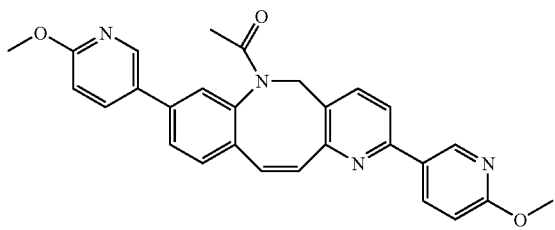

The title compound was obtained as a by-product during the preparation of Example 18. HPLC $R_t$=3.159 min; LCMS Found: (M+H)$^+$=465.

Example 23

6-Acetyl-3-fluoro-5,6-dihydro-2-(6-methoxy-3-pyridinyl)pyrido[3,2-c][1]benzazocine-8-carbonitrile

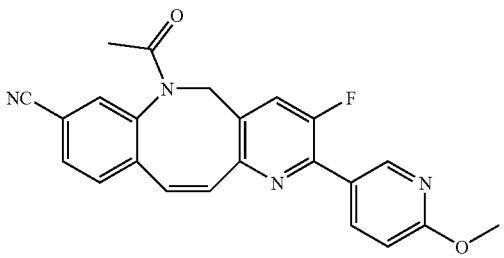

A mixture of Example 7 (10 mg, 0.024 mmol), Zn(CN)$_2$ (2.8 mg, 0.024 mmol) and a catalytic amount of Pd(PPh$_3$)$_4$ in toluene (0.3 mL) was heated at 130° C. under N$_2$ for 40 minutes. Additional Zn(CN)$_2$ and Pd(PPh$_3$)$_4$ were added, and the mixture was heated for an additional 4 hours. The reaction mixture was cooled to room temperature, concentrated, and the residue was purified by flash chromatography (SiO$_2$, 0% to 30% EtOAc/CH$_2$Cl$_2$) followed by trituration with cold Et$_2$O to give the title compound (1.7 mg, 18%). HPLC $R_t$=2.922 min; LCMS Found: (M+H)$^+$=401.

Example 24

6-Acetyl-5,6-dihydropyrido[4,3-c][1]benzazocine

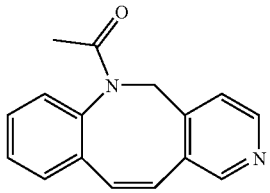

24A. Preparation of (3-iodo-pyridin-4-yl)-methanol

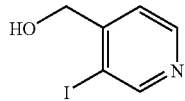

Compound 24A (142 mg, 33%) was prepared from 3-iodo-isonicotinic acid hydrochloride (522 mg, 1.83 mmol) ) using a procedure similar to the synthesis of 1A. HPLC $R_t$=0.34 min.

24B. Preparation of 4-bromomethyl-3-iodo-pyridine hydrobromide

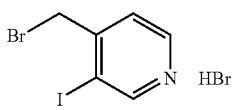

A mixture of 24A (142 mg, 0.604 mmol) and PBr$_3$ (0.61 mL, 1M in CH$_2$Cl$_2$, 0.61 mmol) in THF (5 mL) was heated to reflux for 30 minutes. The reaction mixture was cooled to room temperature, $CH_2Cl_2$ was added and the mixture was filtered. The solid was rinsed with $CH_2Cl_2$ and dried to give 24B (198.2 mg, 86.6%). HPLC $R_t$=1.756 min.

24C. Preparation of 6-Acetyl-5,6-dihydropyrido[4,3-c][1]benzazocine

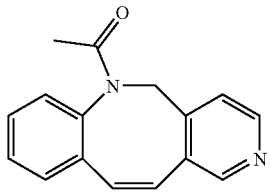

Compound 24C was prepared from 24A and bb in two steps by a route analogous to that used for the preparation of 1D. HPLC $R_t$=1.383 min; LCMS Found: $(M+H)^+$=251.

Example 25

6-Acetyl-3-chloro-5,6-dihydropyrido[4,3-c][1]benzazocine

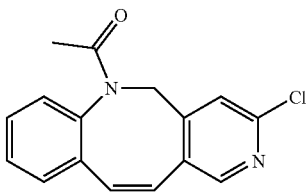

25A. Preparation of 5-tert-butoxycarbonylamino-2-chloro-isonicotinic acid

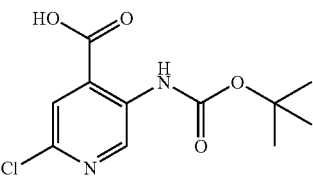

A stirred solution of (6-chloro-pyridin-3-yl)-carbamic acid tert-butyl ester (3.28 g, 14.3 mmol) and TMEDA (6.7 mL, 44.4 mmol) in $Et_2O$ (100 mL) at −78° C. was treated with n-BuLi (4.3 mL, 10 M, 43 mmol). After stirring the mixture at −78° C. for 2 hours $CO_2$ was bubbled into the reaction and the solution was warmed to 0° C. Water was added and the mixture was extracted with EtOAc. The aqueous layer was acidified and extracted with $Et_2O$. The $Et_2O$ layer was washed with brine, dried ($MgSO_4$) and the solvent was removed in vacuo. The residual solid was triturated with Hexane/$Et_2O$ to give 25A (1.38 g, 35%) HPLC $R_t$=2.98 min.

25B. Preparation of 2-chloro-5-iodo-isonicotinic acid

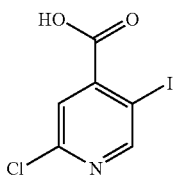

Compound 25A (1.0 g, 3.67 mmol) was added slowly to TFA (15 mL) and stirred at room temperature for 30 minutes. The TFA was removed in vacuo and the residue was treated with $H_2O$ (100 mL) and $H_2SO_4$ (15 mL). The mixture was cooled to 0° C. and $KNO_2$(0.343 g, 4 mmol) was added. The reaction was stirred at 0° C. for 1 hour and then KI (1.2 g, 7.22 mmol) was added. The mixture was heated to 70° C. for 20 minutes then cooled back to 0° C. The solid precipitate was filtered, washed with water and dried in vacuo to give 25B (0.78 g, 75%). HPLC $R_t$=1.54 min.

25C. Preparation of (2-Chloro-5-iodo-pyridin-4-yl)-methanol

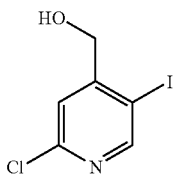

Compound 25C (0.38 g, 51%) was prepared from 25B (0.78 g, 2.75 mmol) using a procedure similar to the synthesis of 1A. HPLC $R_t$=1.74 min.

25D. Preparation of 4-bromomethyl-2-chloro-5-iodo-pyridine

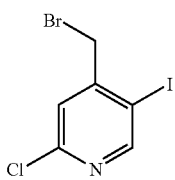

Compound 25D (0.28 g, 60%) was prepared from 25C (0.38 g, 1.4 mmol) using a procedure similar to the synthesis of 1B. HPLC $R_t$=2.72 min.

25E. Preparation of 6-Acetyl-3-chloro-5,6-dihydro-pyrido[4,3-c][1]benzazocine

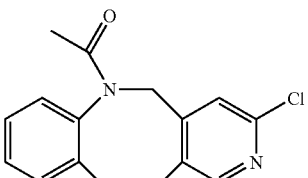

Compound 25E was prepared from 25D and bb in two steps by a route analogous to that used for the preparation of 1D. HPLC $R_t$=2.506 min; LCMS Found: $(M+H)^+$=285.

Example 26

6-Acetyl-5,6-dihydro-3-phenylpyrido[4,3-c][1]benzazocine

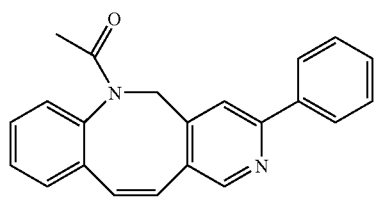

The title compound (12.0 mg, 70%) was prepared from 25E (15.0 mg, 0.053 mmol) and phenylboronic acid (9.6 mg, 0.079 mmol) by a route analogous to that used for the preparation of 2B. HPLC $R_t$=2.356 min; LCMS Found: (M+H)$^+$=327.

Example 27

6-Acetyl-3,8-dichloro-5,6-dihydropyrido[4,3-c][1]benzazocine

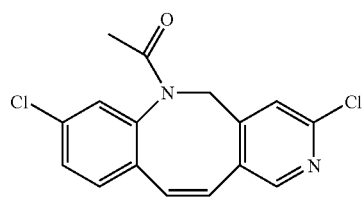

The title compound was prepared from 25D and 6C in two steps by a route analogous to that used for the preparation of 1D. HPLC $R_t$=2.809 min; LCMS Found: (M+H)$^+$=319.

Example 28

6-Acetyl-8-chloro-5,6-dihydro-3-phenylpyrido[4,3-c][1]benzazocine

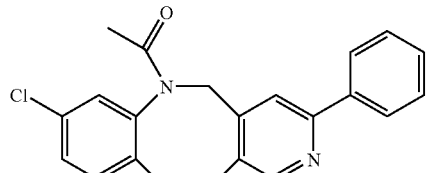

The title compound (1.6 mg, 11.5%) was prepared from Example 27 (12.3 mg, 0.039 mmol) and phenylboronic acid (9.6 mg, 0.079 mmol) by a route analogous to that used for the preparation of 2B. HPLC $R_t$=2.742 min; LCMS Found: (M+H)$^+$=361.

Example 29

6-Acetyl-5,6-dihydro-3,8-diphenylpyrido[4,3-c][1]benzazocine

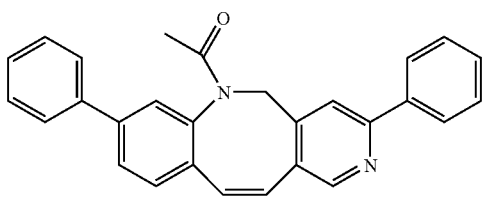

The title compound was obtained as a by-product (1.2 mg, 7.7%) when the compound in Example 28 was prepared from 6D and 2A. HPLC $R_t$=3.222 min; LCMS Found: (M+H)$^+$=403.

Example 30

6-Acetyl-3-(2-acetylphenyl)-5,6-dihydropyrido[4,3-c][1]benzazocine

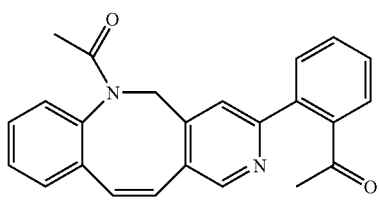

The title compound (12.0 mg, 70%) was prepared from 25E (16.0 mg, 0.055 mmol) and 2-acetylphenylboronic acid (13.8 mg, 0.079 mmol) by a route analogous to that used for the preparation of 2B. HPLC $R_t$=2.05 min; LCMS Found: (M+H)$^+$=367.

Example 31

6-Acetyl-3,9-dichloro-5,6-dihydropyrido[4,3-c][1]benzazocine

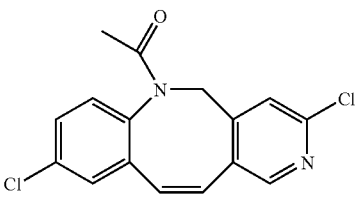

The title compound was prepared from 25D and 9B in two steps by a route analogous to that used for the preparation of 1D. HPLC $R_t$=2.836 min; LCMS Found: (M+H)$^+$=319.

Example 32

6-Acetyl-9-chloro-5,6-dihydro-3-phenylpyrido[4,3-c][1]benzazocine

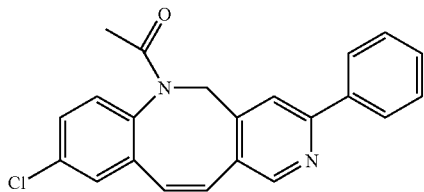

The title compound (5.1 mg, 29%) was prepared from Example 31 (15 mg, 0.047 mmol) and phenylboronic acid (8.6 mg, 0.071 mmol) by a route analogous to that used for the preparation of 2B. HPLC $R_t$=2.806 min; LCMS Found: $(M+H)^+$=361.

Examples 33 to 38

The following compounds in Table 1 have been synthesized utilizing the procedures described in Example 32 starting from Example 31 and commercially available boronic acids or Examples 83-85.

TABLE 1

| Example No. | $R_7$ | $R_{10}$ | Compound name | [M + H] | HPLC Ret Time (min) |
|---|---|---|---|---|---|
| 33 | Cl | 2-acetylphenyl | 6-Acetyl-3-(2-acetylphenyl)-9-chloro-5,6-dihydropyrido[4,3-c][1]benzazocine | 403 | 2.32 |
| 34 | Cl | 2-methoxyphenyl | 6-Acetyl-9-chloro-5,6-dihydro-3-(2-methoxyphenyl)pyrido[4,3-c][1]benzazocine | 391 | 3.00 |
| 35 | Cl | 2-[(dimethylamino)sulfonyl]phenyl | 6-Acetyl-9-chloro-3-[2-[(dimethylamino)sulfonyl]phenyl]-5,6-dihydropyrido[4,3-c][1]benzazocine | 468 | 3.21 |
| 37 | Cl | 2-acetamidophenyl | N-[2-(6-Acetyl-9-chloro-5,6-dihydropyrido[4,3-c][1]benzazocin-3-yl)phenyl]acetamide, trifluoroacetic acid salt (1:1) | 418 | 3.45 |

TABLE 1-continued

| Example No. | $R_7$ | $R_{10}$ | Compound name | [M + H] | HPLC Ret Time (min) |
|---|---|---|---|---|---|
| 38 | Cl | (2-methylsulfonylamino)phenyl | 6-Acetyl-9-chloro-5,6-dihydro-3-[2-[(methylsulfonyl)amino]phenyl]pyrido[4,3-c][1]benzazocine | 454 | 3.58 |

Example 39

6-Acetyl-9-chloro-5,6-dihydro-3-[2-(1-hydroxyethyl)phenyl]pyrido[4,3-c][1]benzazocine

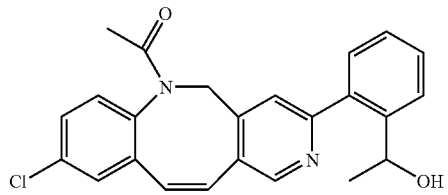

To compound 33 (26 mg, 0.064 mmol) in THF (3 mL) at 0° C. was added lithiumborohydride (2.1 mg, 0.09 mmol). The reaction was stirred for 2 hours at room temperature. The reaction was quenched with ice and concentrated. The residue was purified by flash chromatography (SiO2, EtOAc) to give a yellow solid. HPLC $R_t$=3.35 min. m/z=387 (M+H$^+$).

Example 40

6-Acetyl-9-chloro-5,6-dihydro-3-[2-(1-methoxyethyl)phenyl]pyrido[4,3-c][1]benzazocine, trifluoroacetic acid salt (1:1)

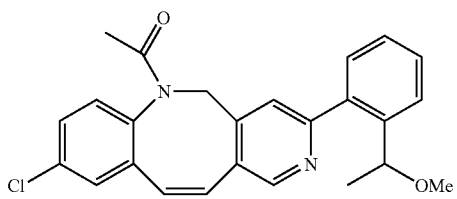

To compound 39 (9 mg, 0.02 mmol) in THF (1 mL) was added sodium hydride (60% suspension in mineral oil). The reaction mixture was stirred overnight. The mixture was concentrated and purified by preparative reversed-phase HPLC to give the title compound as a oil. HPLC $R_t$=3.66 min.

Example 41

11-Acetyl-11,12-dihydro-3-phenylpyrido[3,4-c][1]benzazocine

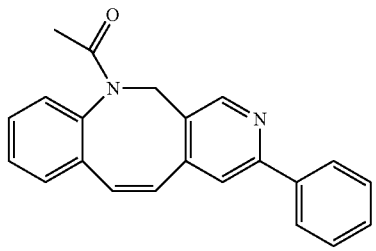

41A. Preparation of (4,6-dichloro-pyridin-3-yl)-methanol

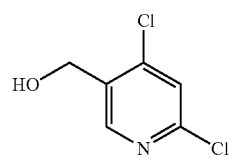

Compound 41A (2.5 g, 60%) was prepared from 4,6-dichloro-nicotinic acid (4.5 g, 23.4 mmol) using a procedure similar to the synthesis of 1A.

41B. Preparation of 2,4-dichloro-5-chloromethyl-pyridine

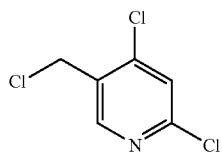

To a stirred solution of 41A (2.5 g, 14 mmol) in CH$_2$Cl$_2$ (20 mL) was added slowly SOCl$_2$ (1.2 mL, 14 mmol) at room temperature. The reaction was stirred for 15 minutes, cooled to 0° C. and washed with saturated aqueous NaHCO$_3$. The CH$_2$Cl$_2$ layer was dried (MgSO$_4$), concentrated in vacuo and purified by flash chromatography (SiO$_2$, CH$_2$Cl$_2$) to give 41B (1.3 g, 47%).

41C. Preparation of N-(4,6-dichloro-pyridin-3-ylmethyl)-N-(2-vinyl-phenyl)-acetamide

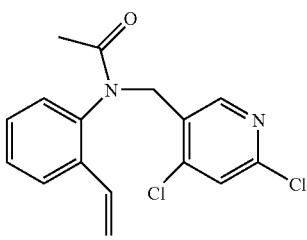

Compound 41C (210 mg, 82%) was prepared from 41B (157 mg, 0.8 mmol) and bb (129 mg, 0.8 mmol) using a procedure similar to the synthesis of 1C.

41D. Preparation of 1-(3-chloro-12H-2,11-diaza-dibenzo[a,e]cycloocten-11-yl)-ethanone

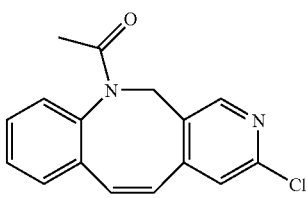

Compound 41D (117 mg, 63%) was prepared from 41C (210 mg, 0.65 mmol) using a procedure similar to the synthesis of 1D. HPLC R$_t$=2.519 min; LCMS Found: (M+H)$^+$=285.

41E. Preparation of 11-Acetyl-11,12-dihydro-3-phenylpyrido[3,4-c][1]benzazocine

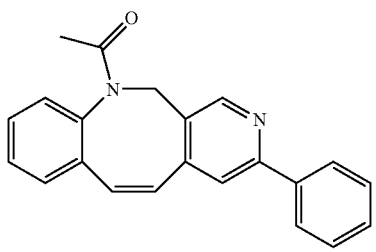

Compound 41E (10.7 mg, 47%) was prepared from 41D (20 mg, 0.070 mmol) and phenylboronic acid (12.8 mg, 0.105 mmol) by a route analogous to that used for the preparation of 2B. HPLC R$_t$=2.286 min; LCMS Found: (M+H)$^+$=327.

Example 42

11-Acetyl-11,12-dihydro-3-(6-methoxy-3-pyridinyl)pyrido[3,4-c][1]benzazocine

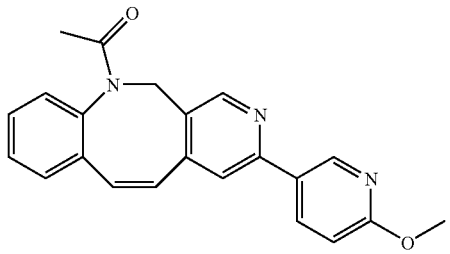

The title compound (16.3 mg, 65%) was prepared from 41D (20 mg, 0.07 mmol) and 2A (24.7 mg, 0.105 mmol) by a route analogous to that used for the preparation of 2B. HPLC R$_t$=2.453 min; LCMS Found: (M+H)$^+$=358.

Example 43

11-Acetyl-11,12-dihydro-3-[6-(4-morpholinyl)-3-pyridinyl]pyrido[3,4-c][1]benzazocine

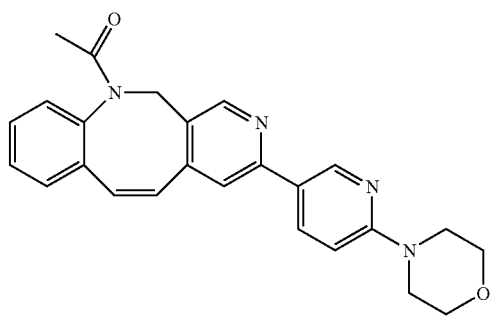

The title compound (3.5 mg, 12%) was prepared from 41D (20 mg, 0.07 mmol) and 5A (30.5 mg, 0.105 mmol) by a route analogous to that used for the preparation of 2B. HPLC R$_t$=2.153 min; LCMS Found: (M+H)$^+$=413.

Example 44

11-Acetyl-3,9-dichloro-11,12-dihydropyrido[3,4-c][1]benzazocine

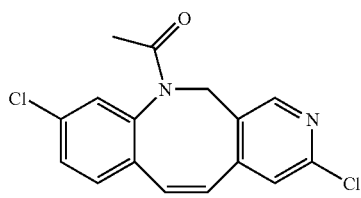

The title compound (70.6 mg, 54%) was prepared from 6C (80 mg, 0.41 mmol) and 41B (80 mg, 0.41 mmol) in two steps by a route analogous to that used for the preparation of 1D. HPLC R$_t$=2.782 min; LCMS Found: (M+H)$^+$=319.

Example 45

11-Acetyl-9-chloro-11,12-dihydro-3-(6-methoxy-3-pyridinyl)pyrido[3,4-c][1]benzazocine

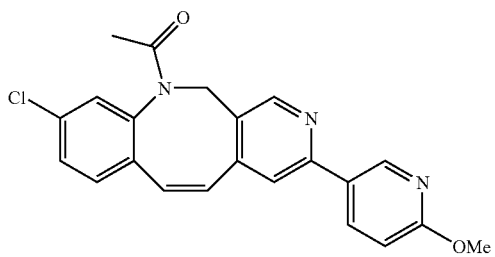

The title compound was prepared from Example 44 (16.1 mg, 0.051 mmol) and 2A (17.8 mg, 0.076 mmol) by a route analogous to that used for the preparation of 2B. HPLC $R_t$=2.712 min; LCMS Found: $(M+H)^+$=392.

Example 46

11-Acetyl-11,12-dihydro-3,9-bis(6-methoxy-3-pyridinyl)pyrido[3,4-c][1]benzazocine

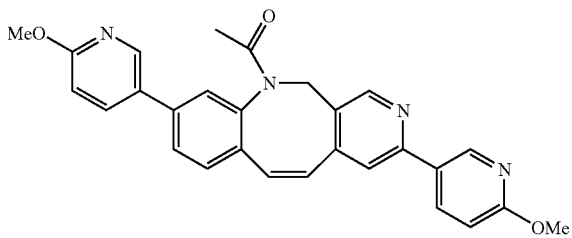

The title compound was obtained as a by-product when the compound in Example 45 was prepared (21%). HPLC $R_t$=2.929 min; LCMS Found: $(M+H)^+$=465.

Example 47

11-Acetyl-9-chloro-11,12-dihydro-3-[6-(4-morpholinyl)-3-pyridinyl]pyrido [3,4-c][1]benzazocine

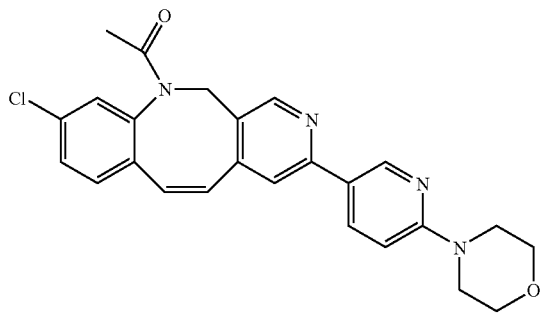

The title compound (18.9 mg, 61%) was prepared from Example 44 (22.0 mg, 0.069 mmol) and 5A (21.0 mg, 0.072 mmol) by a route analogous to that used for the preparation of 2B. HPLC $R_t$=2.386 min; LCMS Found: $(M+H)^+$=447.

Example 48

11-Acetyl-3,8-dichloro-11,12-dihydropyrido[3,4-c][1]benzazocine

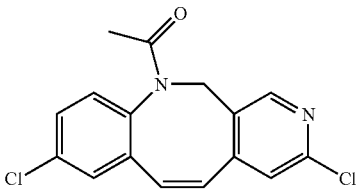

The title compound (67.6 mg, 52%) was prepared from 9B (80 mg, 0.41 mmol) and 41B (80 mg, 0.41 mmol) in two steps by a route analogous to that used for the preparation of 1D. HPLC $R_t$=2.886 min; LCMS Found: $(M+H)^+$=319.

Example 49

11-Acetyl-8-chloro-11,12-dihydro-3-(6-methoxy-3-pyridinyl)pyrido[3,4-c][1]benzazocine

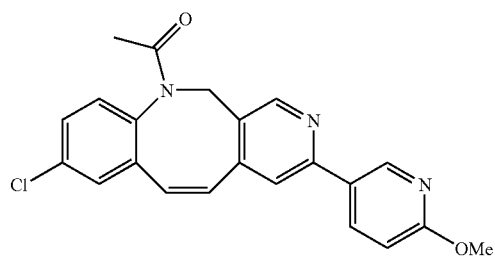

The title compound (3.0 mg, 13%) was prepared from Example 48 (17.9 mg, 0.056 mmol) and 2A (19.8 mg, 0.084 mmol) by a route analogous to that used for the preparation of 2B. HPLC $R_t$=2.839 min; LCMS Found: $(M+H)^+$=392.

Example 50

11-Acetyl-8-chloro-11,12-dihydro-3-[6-(4-morpholinyl)-3-pyridinyl]pyrido [3,4-c][1]benzazocine

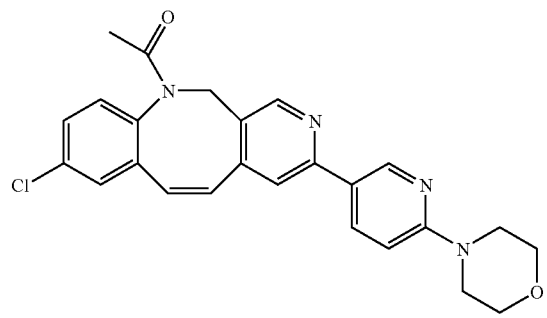

The title compound (19.2 mg, 62%) was prepared from the Example 48 (22.0 mg, 0.069 mmol) and 5A (21.0 mg, 0.072 mmol) by a route analogous to that used for the preparation of 2B. HPLC $R_t$=2.429 min; LCMS Found: $(M+H)^+$=447.

Example 51

11-Acetyl-11,12-dihydropyrido[2,3-c][1]benzazocine

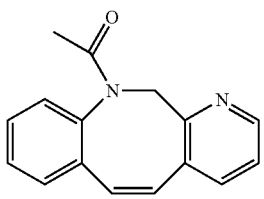

51A. Preparation of (3-iodo-pyridin-2-yl)-methanol

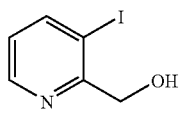

Compound 51A (10 mg, 10%) was prepared from 3-iodo-pyridine-2-carboxylic acid (100 mg, 0.4 mmol)) using a procedure similar to the synthesis of 1A. HPLC $R_t$=0.3 min

51B. Preparation of 2-bromomethyl-3-iodo-pyridine

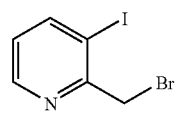

Compound 51B (9.7 mg, 76%) was prepared from 51A (10 mg, 0.04 mmol) using a procedure similar to the synthesis of 2B. HPLC $R_t$=2.22 min.

51C. Preparation of N-(3-iodo-pyridin-2-ylmethyl)-N-(2-vinyl-phenyl)-acetamide

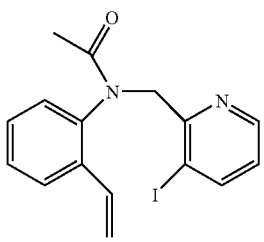

Compound 51C (8.5 mg, 70%) was prepared from bb (5.2 mg, 0.032 mmol) and 51B (9.7 mg, 0.33 mmol) by a route analogous to that used for the preparation of 1C. HPLC $R_t$=2.929 min.

51D. Preparation of 11-Acetyl-11,12-dihydropyrido[2,3-c][1]benzazocine

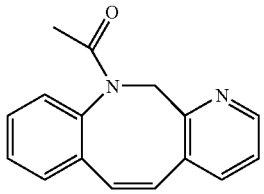

Compound 51D (3.1 mg, 55%) was prepared from 51C (8.5 mg, 0.0225 mmol) by a route analogous to that used for the preparation of 1D. HPLC $R_t$=1.503 min; LCMS Found: $(M+H)^+$=251.

Example 52

11-Acetyl-11,12-dihydro-3-(6-methoxy-3-pyridinyl)pyrido[2,3-c][1]benzazocine

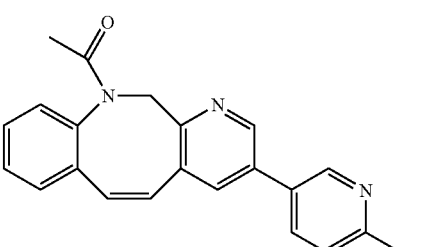

52A. Preparation of 3,5-dibromo-2-methyl-pyridine

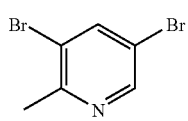

To a solution of 3,5-dibromo-6-methyl-pyridin-2-ylamine (2.0 g, 7.5 mmol) in THF (75 mL) was added t-butylnitrite (1.5 mL, 12.6 mmol) and the reaction was heated to reflux for 2 hours. The reaction was concentrated in vacuo and purified by flash chromatography (SiO$_2$, CH$_2$Cl$_2$) to give 52A (0.8 g 42%). HPLC $R_t$=2.77 min.

52B. Preparation of 3,5-dibromo-2-bromomethyl-pyridine

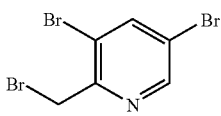

To a solution of 52A (1.25 g, 4.98 mmol) in CCl$_4$ (7 ML) was added NBS (0.89 g, 4.98 mmol) followed by catalytic AIBN and the mixture was heated to reflux for 4 hours. The reaction was cooled to room temperature, filtered and concentrated in vacuo. The residue was purified by flash chromatography (SiO$_2$, 10% CH$_2$Cl$_2$/Hexane then 50% CH$_2$Cl$_2$/Hexane) to give 52B (0.90 g, 55%). HPLC $R_t$=2.85 min.

52C. Preparation of 1-(3-bromo-12H-1,11-diaza-dibenzo[a,e]cycloocten-11-yl)-ethanone

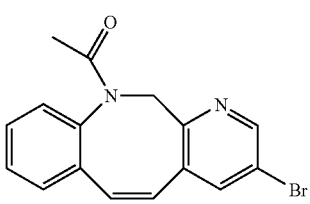

Compound 52C (46.6 mg, 16%) was prepared from bb (147 mg, 0.91 mmol) and 52B (300 mg, 0.91 mmol) in two steps by a route analogous to that used for the preparation of 1D.

52D. Preparation of 11-Acetyl-11,12-dihydro-3-(6-methoxy-3-pyridinyl)pyrido[2,3-c][1]benzazocine

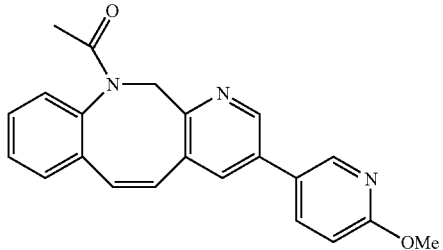

Compound 52D (20.9 mg, 91%) was prepared from 52C (20 mg, 0.061 mmol) and 2A (14.3 mg, 0.061 mmol) by a route analogous to that used for the preparation of 2B. HPLC $R_t$=2.419 min; LCMS Found: $(M+H)^+$=358.

Examples 53 to 54

The following compounds in Table 2 have been synthesized utilizing the procedures described in Example 52 from 6C or 9B.

55A. Preparation of 3-Bromo-6-chloro-2-methyl-pyridine

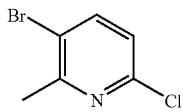

To a solution of 5-bromo-6-methyl-pyridin-2-ylamine (2.0 g, 10.6 mmol) in concentrated HCl (10 mL) was added NaNO$_2$ (1.1 g, 15.9 mmol) at room temperature. The reaction was stirred for 2 hours, then cooled to 0° C., made basic with NaOH and extracted with Et$_2$O. The Et$_2$O layer was dried (MgSO$_4$) and concentrated in vacuo to give 55A (0.63 g, 28%). HPLC $R_t$=2.29 min.

55B. Preparation of 3-Bromo-2-bromomethyl-6-chloro-pyridine

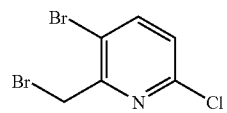

Compound 55B (0.33 g, 45%) was prepared from 55A (0.53 g, 2.57 mmol) using a procedure similar to the synthesis of 52B. HPLC $R_t$=2.47 min.

TABLE 2

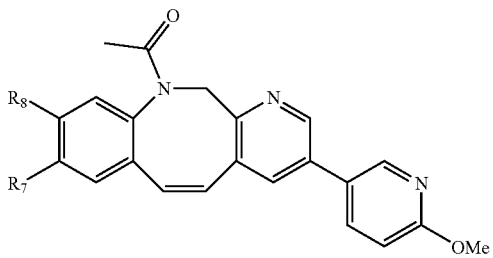

| Example No. | R$_8$ | R$_7$ | Compound name | [M + H] | HPLC Ret Time (min) |
|---|---|---|---|---|---|
| 53 | Cl | H | 11-Acetyl-9-chloro-11,12-dihydro-3-(6-methoxy-3-pyridinyl)pyrido[2,3-c][1]benzazocine | 392 | 2.742 |
| 54 | H | Cl | 11-Acetyl-8-chloro-11,12-dihydro-3-(6-methoxy-3-pyridinyl)pyrido[2,3-c][1]benzazocine | 392 | 2.876 |

Example 55

11-Acetyl-11,12-dihydro-2-phenylpyrido[2,3-c][1]benzazocine

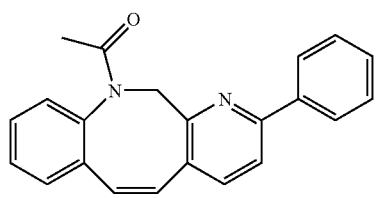

55C. Preparation of 1-(2-chloro-12H-1,11-diaza-dibenzo[a,e]cycloocten-11-yl)-ethanone

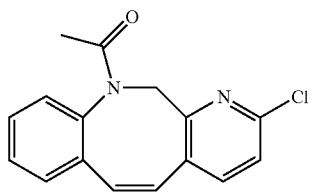

Compound 55C (27.7 mg, 28%) was prepared from bb (56.4 mg, 0.35 mmol) and 55B (100 mg, 0.35 mmol) in two steps by a route analogous to that used for the preparation of 1D.

55D. Preparation of 11-Acetyl-11,12-dihydro-2-phenylpyrido[2,3-c][1]benzazocine

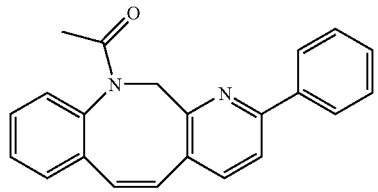

Compound 55D (6.0 mg, 100%) was prepared from 55C (5.0 mg, 0.018 mmol) and phenylboronic acid (2.2 mg, 0.018 mmol) by a route analogous to that used for the preparation of 2B. HPLC $R_t$=2.729 min; LCMS Found: (M+H)$^+$=327.

Examples 56 to 57

The following compounds in Table 3 have been synthesized utilizing the procedures described in preparation of Example 55 from 6C or 9B.

TABLE 3

| Example No. | $R_8$ | $R_7$ | Compound name | [M + H] | HPLC Ret Time (min) |
|---|---|---|---|---|---|
| 56 | Cl | H | 11-Acetyl-9-chloro-11,12-dihydro-2-phenylpyrido[2,3-c][1]benzazocine | 361 | 3.152 |
| 57 | H | Cl | 11-Acetyl-8-chloro-11,12-dihydro-2-phenylpyrido[2,3-c][1]benzazocine | 361 | 3.236 |

Example 58

11-Acetyl-2-(2-acetylphenyl)-11,12-dihydropyrido[2,3-c][1]benzazocine

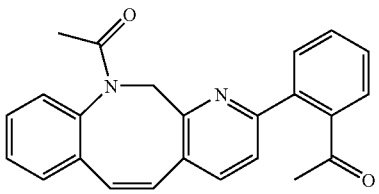

The title compound (6.1 mg, 92%) was prepared from 55C (5.0 mg, 0.018 mmol) and 2-acetylphenylboronic acid (2.9 mg, 0.018 mmol) by a route analogous to that used for the preparation of 2B. HPLC $R_t$=2.363 min; LCMS Found: (M+H)$^+$=369.

Examples 59 to 60

The following compounds in Table 4 have been synthesized utilizing the procedures described for the preparation of Example 58 from the corresponding chloride and 2-acetylphenylboronic acid.

TABLE 4

| Example No. | $R_8$ | $R_7$ | Compound name | [M + H] | HPLC Ret Time (min) |
|---|---|---|---|---|---|
| 59 | Cl | H | 11-Acetyl-2-(2-acetylphenyl)-9-chloro-11,12-dihydropyrido[2,3-c][1]benzazocine | 403 | 2.729 |
| 60 | H | Cl | 11-Acetyl-2-(2-acetylphenyl)-8-chloro-11,12-dihydropyrido[2,3-c][1]benzazocine | 403 | 2.812 |

Example 61

2-(11-Acetyl-11,12-dihydropyrido[2,3-c][1]benzazocin-2-yl)-N-methyl-benzamide

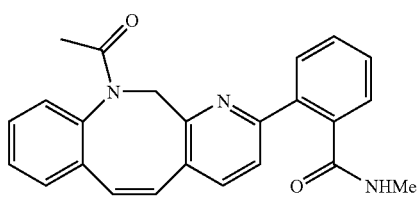

61A. Preparation of 2-(11-Acetyl-11,12-dihydro-1,11-diaza-dibenzo[a,e]cycloocten-2-yl)-benzoic acid

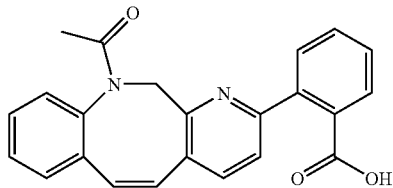

Compound 61A was prepared from 55C (17 mg, 0.060 mmol) and 2-carboxyphenylboronic acid (10 mg, 0.060 mmol) by a route analogous to that used for the preparation of 2B.

61B. Preparation of 2-(11-Acetyl-11,12-dihydropyrido[2,3-c][1]benzazocin-2-yl)-N-methyl-benzamide

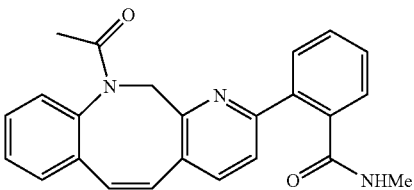

A mixture of 61A, MeNH$_2$·HCl (20 mg, 0.30 mmol), BOP (37 mg, 0.084 mmol) and Et$_3$N (50 μl, 0.036 mmol) was stirred at room temperature for 30 minutes. The reaction mixture was concentrated and purified by flash chromatography (SiO$_2$, 100% CH$_2$Cl$_2$ then 100% EtOAc) to give 61B (11.1 mg, 48% for two steps). HPLC R$_t$=2.063 min; LCMS Found: (M+H)$^+$=384.

61C. Preparation of 2-(6-Acetyl-9-chloro-5,6-dihydropyrido[4,3-c][1]benzazocin-3-yl)-N-methyl-benzamide

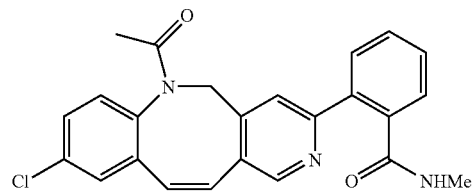

Example 61C was prepared in a manner analogous to Example 61 starting with Example 31. HPLC R$_t$=1.62 min (b) m/z=419 (M+H$^+$).

Examples 62 to 63

The following compounds in Table 5 have been synthesized utilizing the procedures described for preparation of Example 61B from the corresponding chloride.

TABLE 5

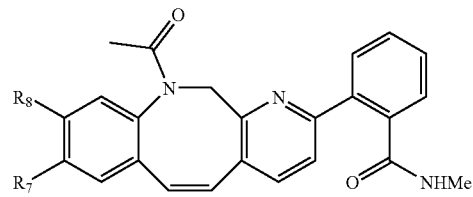

| Example No. | R$_8$ | R$_7$ | Compound name | [M + H] | HPLC Ret Time (min) |
|---|---|---|---|---|---|
| 62 | Cl | H | 2-(11-Acetyl-9-chloro-11,12-dihydropyrido[2,3-c][1]benzazocin-2-yl)-N-methyl-benzamide | 418 | 2.453 |
| 63 | H | Cl | 2-(11-Acetyl-8-chloro-11,12-dihydropyrido[2,3-c][1]benzazocin-2-yl)-N-methyl-benzamide | 418 | 2.539 |

Example 64

6-Acetyl-2-chloro-5,6-dihydropyrimido[5,4-c][1]benzazocine

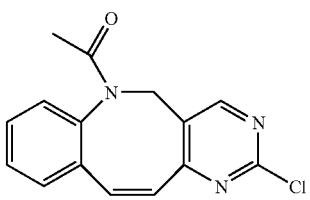

64A. Preparation of 2,4-dichloro-5-chloromethyl-pyrimidine

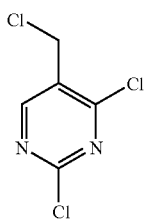

To a solution of 5-hydroxymethyl-pyrimidine-2,4-diol (0.60 g, 4.2 mmol) in POCl₃ (20 mL) was added Et₃N (0.2 mL) and the mixture was heated to reflux for 2 hours. The reaction was concentrated in vacuo and the residue dissolved in EtOAc, washed with saturated aqueous NaHCO₃, dried (MgSO₄) and concentrated in vacuo. The residue was purified by flash chromatography (SiO₂, 100% CH₂Cl₂) to give 64A (0.26 g, 31%).

64B. Preparation of 6-Acetyl-2-chloro-5,6-dihydropyrimido[5,4-c][1]benzazocine

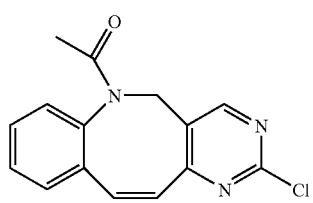

Compound 64B (66.1 mg, 46%) was prepared from 64A (0.10 g, 0.5 mmol) and bb (82 mg, 0.5 mmol) in two steps by a route analogous to that used for the preparation of 1D. HPLC $R_t$=2.286 min; LCMS Found: (M+H)⁺=286.

Examples 65 to 66

The following compounds in Table 6 have been synthesized utilizing the procedures described in preparation of Example 64B from 6C or 9B and 64A.

TABLE 6

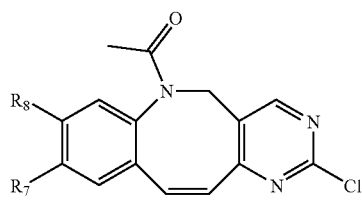

| Example No. | R₈ | R₇ | Compound name | [M + H] | HPLC Ret Time (min) |
|---|---|---|---|---|---|
| 65 | Cl | H | 6-Acetyl-2,8-dichloro-5,6-dihydropyrimido[5,4-c][1]benzazocine | 320 | 2.536 |
| 66 | H | Cl | 6-Acetyl-2,9-dichloro-5,6-dihydropyrimido[5,4-c][1]benzazocine | 320 | 2.676 |

Examples 67 to 70

The following compounds in Table 7 have been synthesized from their corresponding chloride 64-66 and 2A by a route analogous to that used for the preparation of 2B. Compound 70 (BMS-572773) was obtained as a by-product when compound 69 (BMS-572772) was prepared.

TABLE 7

| Example No. | $R_8$ | $R_7$ | Compound name | [M + H] | HPLC Ret Time (min) |
|---|---|---|---|---|---|
| 67 | H | H | 6-Acetyl-5,6-dihydro-2-(6-methoxy-3-pyridinyl)pyrimido[5,4-c][1]benzazocine | 359 | 3.062 |
| 68 | H | Cl | 6-Acetyl-9-chloro-5,6-dihydro-2-(6-methoxy-3-pyridinyl)pyrimido[5,4-c][1]benzazocine | 393 | 3.386 |
| 69 | Cl | H | 6-Acetyl-8-chloro-5,6-dihydro-2-(6-methoxy-3-pyridinyl)pyrimido[5,4-c][1]benzazocine | 393 | 3.279 |
| 70 | (6-methoxy-3-pyridinyl) | H | 6-Acetyl-5,6-dihydro-2,8-bis(6-methoxy-3-pyridinyl)pyrimido[5,4-c][1]benzazocine | 466 | 3.502 |

Examples 71 to 75

The following compounds in Table 8 have been synthesized from their corresponding olefins by a route analogous to that used for the preparation of compound 3.

TABLE 8

| Example No. | Structure | Compound name | [M + H] | HPLC Ret Time (min) |
|---|---|---|---|---|
| 71 | 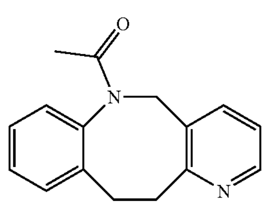 | 6-Acetyl-5,6,11,12-tetrahydropyrido[3,2-c][1]benzazocine | 253 | 1.28 |
| 72 | 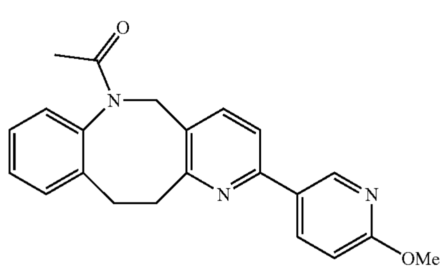 | 6-Acetyl-5,6,11,12-tetrahydro-2-(6-methoxy-3-pyridinyl)pyrido[3,2-c][1]benzazocine | 360 | 2.156 |

TABLE 8-continued

| Example No. | Structure | Compound name | [M + H] | HPLC Ret Time (min) |
|---|---|---|---|---|
| 73 | 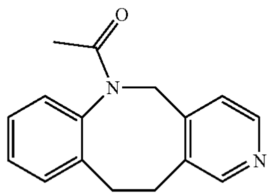 | 6-Acetyl-5,6,11,12-tetrahydropyrido[4,3-c][1]benzazocine | 253 | 1.323 |
| 74 | 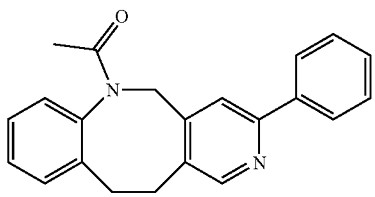 | 6-Acetyl-5,6,11,12-tetrahydro-3-phenylpyrido[4,3-c][1]benzazocine | 329 | 1.986 |
| 75 | 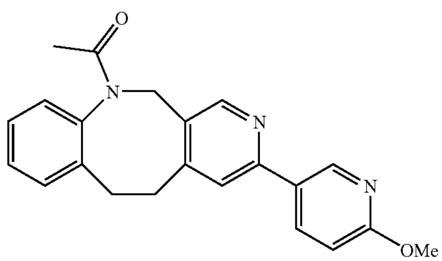 | 11-Acetyl-5,6,11,12-tetrahydro-3-(6-methoxy-3-pyridinyl)pyrido[3,4-c][1]benzazocine | 360 | 2.099 |

Example 76

6-Acetyl-3-(2-acetylphenyl)-9-chloro-5,6-dihydro-pyrido[3,2-c][1]benzazocine

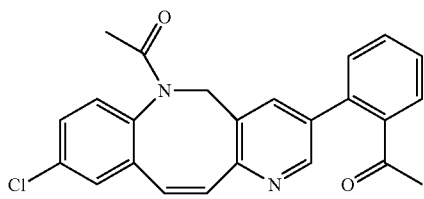

76A. Preparation of 5-Bromo-2-chloro-3-methyl-pyridine

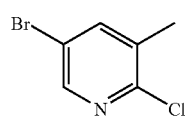

Compound 76A (1.8 g, 67%) was prepared using a procedure similar to the synthesis of 55A from 5-bromo-3-methyl-pyridin-2-ylamine.

76B. Preparation of 5-Bromo-3-bromomethyl-2-chloro-pyridine

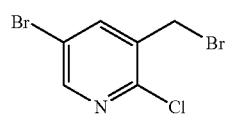

Compound 76B (0.46 g, 33%) was prepared from 76A (1.0 g, 4.9 mmol) using a procedure similar to the synthesis of 55B.

76C. Preparation of N-(5-Bromo-2-chloro-pyridin-3-ylmethyl)-N-(4-chloro-2-vinyl-phenyl)-acetamide

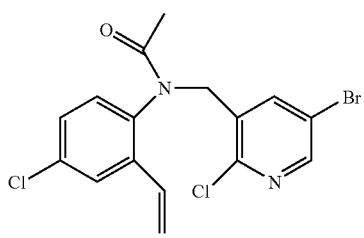

Compound 76C (0.19 g, 94%) was prepared from 76B (0.145 g, 0.51 mmol) and 9B (0.1 mg, 0.51 mmol) using a procedure similar to the synthesis of 1C.

76D. Preparation of 1-(3-Bromo-9-chloro-5H-1,6-diaza-dibenzo[a,e]cycloocten-6-yl)-ethanone

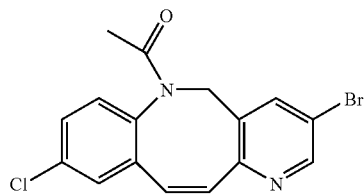

Compound 76E (22 mg, 47%) was prepared from 76C (50 mg, 0.13 mmol) by a route analogous to that used for the preparation of 1D.

76F. Preparation of 6-Acetyl-3-(2-acetylphenyl)-9-chloro-5,6-dihydro-pyrido[3,2-c][1]benzazocine

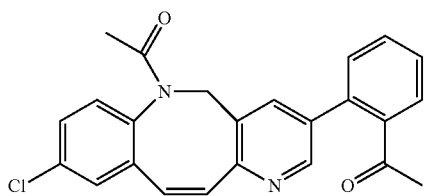

Compound 76F (23 mg, 6%) was prepared from 76E (20 mg, 0.055 mmol) and 2-Acetylphenylboronic acid (2.2 mg, 0.018 mmol) by a route analogous to that used for the preparation of 2B. HPLC $R_t$=1.99 min(b); LCMS Found: $(M+H)^+$=403.

Example 77

6-Acetyl-9-chloro-3-[2-[(dimethylamino)sulfonyl]phenyl]-5,6-dihydropyrido[3,2-c][1]benzazocine, trifluoroacetic acid salt (1:1)

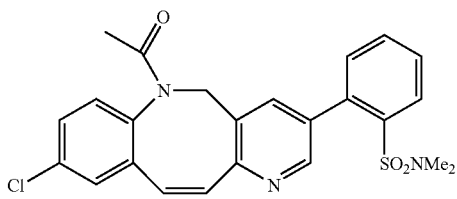

77A. Preparation of 4-Bromomethyl-2-chloro-5-iodo-pyridine

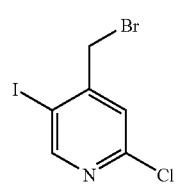

Compound 77A was prepared from (2-Chloro-5-iodo-pyridin-4-yl)-methanol (0.2 g, 1.38 mmol) using a procedure similar to the synthesis of 1B.

77B. Preparation of N-(2-Chloro-5-iodo-pyridin-4-ylmethyl)-N-(4-chloro-2-vinyl-phenyl)-acetamide

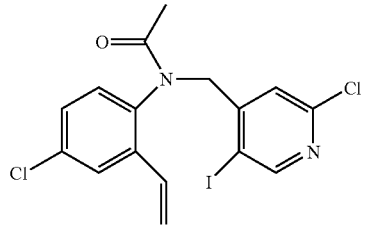

Compound 77B was prepared from 77A (0.75 mg, 0.22 mmol) and 76C (0.44 g, 0.22 mmol) using a procedure similar to the synthesis of 1C.

77C. Preparation 1-(3,9-Dichloro-5H-2,6-diaza-dibenzo[a,e]cycloocten-6-yl)-ethanone

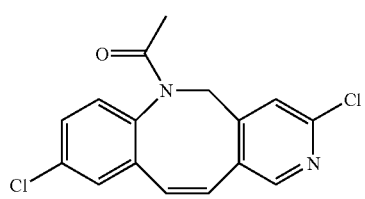

Compound 77C (26 mg, 73%) was prepared from 77B (50 mg, 0.13 mmol) by a route analogous to that used for the preparation of 1D.

77D. Preparation of 6-Acetyl-9-chloro-3-[2-[(dimethylamino)sulfonyl]phenyl]-5,6-dihydropyrido[3,2-c][1]benzazocine

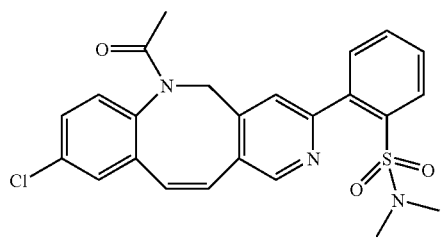

Compound 77D was prepared from 77C (15 mg, 0.047 mmol) and the corresponding boronic acid (16.2 mg, 0.07 mmol) by a route analogous to that used for the preparation of 2B. HPLC $R_t$=3.10 min; LCMS Found: $(M+H)^+$=468.

Example 78

12-Acetyl-5,6,11,12-tetrahydro-9-phenyl-pyrido[2,3-c][2]benzazocine

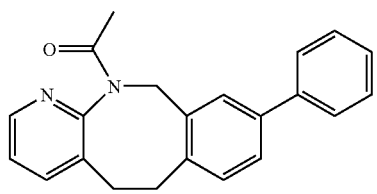

78A. Preparation of 3-Bromo-pyridin-2-ylamine

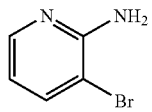

To a stirred solution of N-(3-Bromo-pyridin-2-yl)-2,2-dimethyl-propionamide[a] (2.52g, 9.80 mmol) in methanol (15 mL) was added 3N KOH aqueous solution (6.70 mL, 20.1 mmol). This reaction mixture was heated at 80° C. for 16 h, cooled and concentrated in vacuo. The crude product was diluted with water (40 mL), saturated with NaCl, and extracted with EtOAc (3×70mL). The combined EtOAc extracts were dried (MgSO$_4$), filtered and concentrated in vacuo to give desired 3-Bromo-pyridin-2-ylamine 78A in 88% yield.

[a] Bulletin des Societes Chimiques Belges, 97(1), 51-3; 1988. JCS Perkin Trans I, 1999, P 1505-1510

78B. Preparation of N-(3-Bromo-pyridin-2-yl)-acetamide

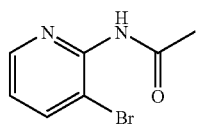

3-Bromo-pyridin-2-ylamine (1.00 g, 5.78 mmol) was dissolved in acetic anhydride (12.4 mL). This solution was heated at 100° C. for 16 h and cooled to room temperature. The mixture was concentrated in vacuo, diluted with EtOAc (100 mL) and poured into a mixture of ice and saturated NaHCO$_3$ solution (150 mL). This mixture was then saturated with solid NaHCO$_3$ and extracted with EtOAc (3×150 mL). The combined EtOAc extracts were dried (MgSO$_4$), filtered and concentrated in vacuo to give 1.49 g of N-(3-Bromo-pyridin-2-yl)-acetamide in a quantitative yield. HPLC $R_t$=1.79 min (YMC S5 ODS column 4.6×50 mm, 10-90% aqueous methanol over 4 minutes containing 0.2% phosphoric acid, 4 mL/min, monitoring at 220 nm) LC/MS: M+H$^+$=215.

78C. Preparation of N-(3-Vinyl-pyridin-2-yl)-acetamide

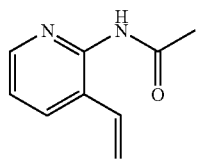

To a stirred mixture of N-(3-Bromo-pyridin-2-yl)-acetamide (1.20 g, 5.58 mmol) in anhydrous toluene (40 mL) under argon was added Tri-n-butyl(vinyl)tin (3.25 mL, 11.1 mmol) and Bis(triphenylphosphine)Palladium dichloride (0.40g, 0.57 mmol). This mixture was heated at 95° C. for 30 minutes and cooled to room temperature. This mixture was then diluted with saturated NaHCO$_3$ solution (100 mL) and extracted with EtOAc (3×120 mL). The combined EtOAc extracts were dried (MgSO$_4$), filtered and concentrated in vacuo. This was purified by a ISCO auto CombiFlash with a RediSep 35 g column, eluted with CH$_2$Cl$_2$-EtOAc, detected at 220 nM to give 420 mg of N-(3-Vinyl-pyridin-2-yl)-acetamide 78C in 46% yield.

78D. Preparation of 2-iodo-5-bromobenzyl bromide

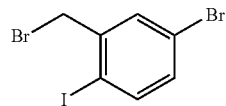

To a stirred mixture of alcohol 2-iodo-5-bromobenzyl alcohol (9.14 g, 29.2 mmol) in of CH$_3$Cl (150 mL) under argon was added 1M PBr$_3$ in CH$_2$Cl$_2$ (35.0 mL, 35.0 mmol). The reaction mixture was stirred at room temperature for 20 minutes and then poured into a mixture of ice and saturated NaHCO$_3$ solution (300 mL). The pH was adjusted to basic by addition of solid NaHCO$_3$. This aqueous layer was extracted with EtOAc (1×600 mL, 2×400 mL). The combined EtOAc extracts were washed with brine (1×100 mL). The organic layer was dried (MgSO$_4$), filtered and concentrated in vacuo to give 2-iodo-5-bromobenzyl bromide (5.69 g, 52%). $^1$H NMR (CDCl$_3$): δ=7.68 (d, 1H, J=8.80 Hz), 7.59 (s, 1H), 7.18 (d, 1H, J=8.80 Hz), 4.51 (s, 2H). HPLC: $R_t$=3.87 min.

78E. Preparation of N-(5-Bromo-2-iodo-benzyl)-N-(3-vinyl-pyridin-2-yl)-acetamide

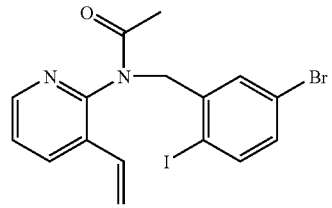

To a stirred solution of N-(3-Vinyl-pyridin-2-yl)-acetamide 78D (122 mg, 0.75 mmol) and 4-Bromo-2-bromomethyl-1-iodo-benzene (285 mg, 0.75 mmol) in anhydrous DMF (6 mL) under argon was added 95% NaH (21 mg, 0.83 mmol). This mixture was stirred at room temperature for 4.5 h and diluted with saturated NaHCO$_3$ solution. This was extracted with EtOAc (4×60 mL). The combined EtOAc extracts were washed with brine (30 mL), dried (MgSO$_4$), filtered and concentrated in vacuo. This was purified by a ISCO auto CombiFlash with a RediSep 10 g column, eluted with CH$_2$Cl$_2$-EtOAc, detected at 220 nM to give 90 mg of desired N-(5-Bromo-2-iodo-benzyl)-N-(3-vinyl-pyridin-2-yl)-acetamide 78E in 29% yield. HPLC $R_t$=3.48 min (YMC S5 ODS column 4.6×50 mm, 10-90% aqueous methanol over 4 minutes containing 0.2% phosphoric acid, 4 mL/min, monitoring at 220 nm) LC/MS: M+H=457.

78F. Preparation of 12-Acetyl-9-bromo-11,12-dihydro-pyrido[2,3-c][2]benzazocine

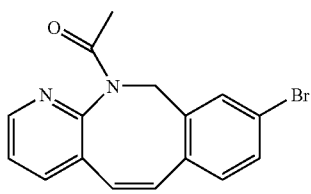

To a stirred mixture of N-(5-Bromo-2-iodo-benzyl)-N-(3-vinyl-pyridin-2-yl)-acetamide E (60.0 mg, 0.13 mmol) and triethyl amine (55.0 μL, 0.39 mmol) in anhydrous DMF (1.4 mL) under argon was added Palladium dichloride (4.60 mg, 26 µmol). This mixture was heated at 65° C. for 1 h, cooled and diluted with saturated NaHCO₃ solution (20 mL). The mixture was extracted with EtOAc (4×30 mL). The combined EtOAc extracts were washed with water (3×10 mL), brine (1×10 mL), dried (MgSO₄), filtered and concentrated in vacuo. This was purified by a ISCO auto CombiFlash with a RediSep 4 g column, eluted with CH₂Cl₂-EtOAc, detected at 254 nM to give 33 mg of 78F in 77% yield. HPLC R$_t$=3.04 min (YMC S5 ODS column 4.6×50 mm, 10-90% aqueous methanol over 4 minutes containing 0.2% phosphoric acid, 4 mL/min, monitoring at 220 nm) LC/MS: M+H=329.

78G. Preparation of 12-Acetyl-11,12-dihydro-9-phenyl-pyrido[2,3-c][2]benzazocine

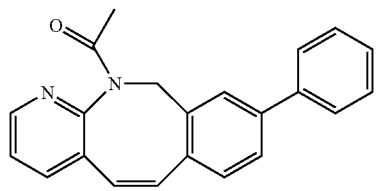

To a stirred mixture of 78F (30.0 mg, 91 µmol) in toluene (0.75 mL) and EtOH (0.45 mL) under argon was added 2M Na₂CO₃ solution (0.45 mL), tetrakis(triphenylphosphine)palladium (0) (6 mg) and phenyl boronic acid (16.7 mg, 0.13 mmol). This mixture was heated at 100° C. for 20 minutes and cooled to room temperature. This mixture was diluted with saturated NaHCO₃ solution (15 mL) and extracted with EtOAc (3×25 mL). The combined EtOAc extracts were washed with brine (1×10 mL), dried (MgSO₄), filtered and concentrated in vacuo. This was purified by a ISCO auto CombiFlash with a RediSep 4 g column, eluted with CH₂Cl₂-EtOAc, detected at 254 nM to give 22 mg of impure compound. This was further purified by a Shimadzu auto prep HPLC, employing 30% to 100% 10 minute gradient elution with 0.1%TFA in MeOH-water solvent system, 220 nM detection, 20 mL/min elution with a YMC ODS S5 20×100 mm column to give 17.7 mg of 78G in 60% yield. HPLC R$_t$=3.48 min (YMC S5 ODS column 4.6×50 mm, 10-90% aqueous methanol over 4 minutes containing 0.2% phosphoric acid, 4 mL/min, monitoring at 220 nm) LC/MS: M+H=327.

Example 78

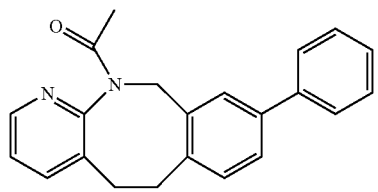

To a stirred solution of 78G (15.0 mg, 45.9 µmol) in MeOH (10 mL) under argon was added 10% Pd/C (8 mg). The atmosphere was switched to H₂ by several vacuum-fill cycles. The mixture was stirred at room temperature for 45 minutes. The catalyst was filtered off through a 4 micron polycarbonate filter and rinsed with MeOH (2×10 mL) and CH₂Cl₂ (2×10 mL). The filtrate was concentrated in vacuo to give 8.8 mg of 78 in 59% yield. HPLC R$_t$=3.25 min (YMC S5 ODS column 4.6×50 mm, 10-90% aqueous methanol over 4 minutes containing 0.2% phosphoric acid, 4 mL/min, monitoring at 220 nm) LC/MS: M+H=329.

The following compounds were prepared in a manner analogous to that described for 78 starting from the appropriate aminopyridine.

Example 79

5-Acetyl-5,6-dihydro-pyrido[3,2-c][2]benzazocine

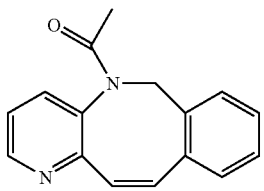

HPLC R$_t$=1.65 min (YMC S5 ODS column 4.6×50 mm, 10-90% aqueous methanol over 4 minutes containing 0.2% phosphoric acid, 4 mL/min, monitoring at 220 nm) LC/MS: M+H=251

Example 80

5-Acetyl-5,6-dihydro-pyrido[4,3-c][2]benzazocine

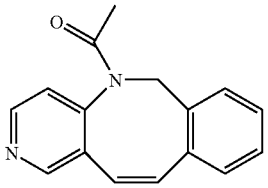

HPLC R$_t$=1.79 min (YMC S5 ODS column 4.6×50 mm, 10-90% aqueous methanol over 4 minutes containing 0.2% phosphoric acid, 4 mL/min, monitoring at 220 nm) LC/MS: M+H=489

Example 81

12-Acetyl-9-bromo-11,12-dihydro-pyrido[3,4-c][2]benzazocine

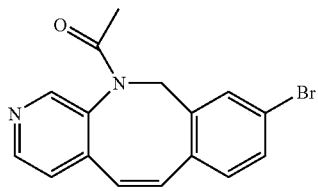

HPLC R$_t$=2.49 min (YMC S5 ODS column 4.6×50 mm, 10-90% aqueous methanol over 4 minutes containing 0.2% phosphoric acid, 4 mL/min, monitoring at 220 nm) LC/MS: M+H=329

Example 82

12-Acetyl-9-(2-acetylphenyl)-11,12-dihydro-pyrido[3,4-c][2]benzazocine

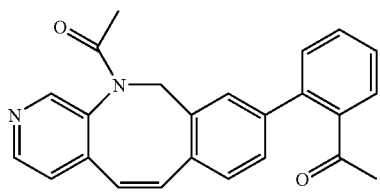

HPLC R$_t$=2.62 min (YMC S5 ODS column 4.6×50 mm, 10-90% aqueous methanol over 4 minutes containing 0.2% phosphoric acid, 4 mL/min, monitoring at 220 nm) LC/MS: M+H=369.

Example 83

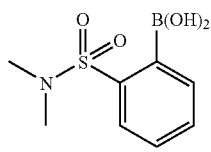

83A. Preparation of N,N-Dimethyl-benzenesulfonamide

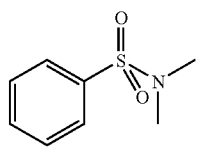

A solution of phenylsulfonyl chloride (10 mL, 78 mmol) in THF (50 mL) was cooled to 0° C. and treated dropwise with dimethylamine (20 mL) as a 40% solution in water maintaining a temperature below 50° C. The reaction was warmed to room temperature for one hour and poured into water. The solution was concentrated to remove THF and the residue was cooled to 0° C. The resulting solid was filtered and dried in vacuo to afford 83A (14 g, 97%).

Example 83

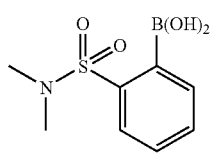

A solution of 83A (3.08 g, 16.6 mmol) in Et$_2$O (50 mL) was cooled to −78° C. To this reaction mixture was added nBuLi (12.5 mL, 20 mmol, 1.6 M in hexanes) dropwise. The resulting solution was warmed to room temperature and stirred for one hour. The reaction was cooled to −78° C. and treated with triisopropyl borate (5.36 mL, 23.2 mmol) dropwise over 30 minutes. The reaction mixture was warmed to room temperature overnight then quenched with 1N HCl and stirred for one hour. The mixture was extracted with Et$_2$O and the organics were washed with 1M NaOH. The aqueous layer was neutralized with 1 N HCl and extracted with Et$_2$O, dried (Na$_2$SO$_4$), filtered and concentrated to afford 83.

Example 84

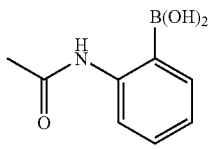

84A. Preparation of 2-Nitrophenyl boronic acid

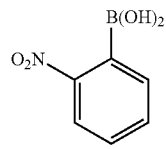

A solution of phenyl boronic acid (5.0 g, 41 mmol) in acetic anhydride (50 mL) at −15° C. was treated with nitric acid (2.5 mL) dropwise over 30 minutes maintaining a temperature below −10° C. The reaction was allowed to warm to room temperature overnight, then poured onto ice. The resulting solution was concentrated to 25 mL and water (50 mL) was added. The mixture was again concentrated. This procedure was repeated five times. The solid that developed was filtered and dried. The crude product was purified by flash chromatography (SiO$_2$, 2% EtOH/CH$_2$Cl$_2$) to afford the desired product (1.0 g, 15%).

84B. Preparation of 2-Aminophenyl boronic acid

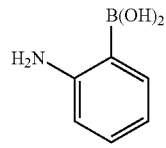

A mixture of 84A (1.0 g, 6 mmol) and 10% Pd/C (50 mg) in EtOH (50 mL) was hydrogenated in a Paar shaker at 1 bar for 8 hours. The mixture was filtered through a pad of celite and the filtrate was concentrated. The resulting residue was triturated with hexanes and the resulting solid was filtered to afford 84B (0.4g, 50%).

Example 84

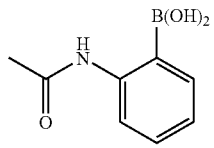

A solution of 84B (200 mg, 1.45 mmol) in CH$_2$Cl$_2$ (1 mL) was treated with Et$_3$N (0.126 mL) and acetyl chloride (0.11 mL). The reaction mixture was stirred at room temperature for two hours. Upon completion the mixture was concentrated and precipitated from water. The precipitate was dried in vacuo to afford the desired compound (70 mg, 39%).

Example 85

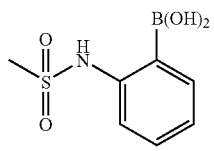

A solution of 84B (200 mg, 1.45 mmol) in CH$_2$Cl$_2$ (1 mL) was treated with Et$_3$N (0.35 mL) and methanesulfonyl chloride (0.10 mL). The reaction mixture was stirred at room temperature for two hours. Upon completion the mixture was concentrated, water was added and the mixture was extracted with CH$_2$Cl$_2$. The organic extracts were dried (Na$_2$SO$_4$), filtered and concentrated to afford the desired compound (50 mg, 16%).

What is claimed is:

1. A compound of formula I:

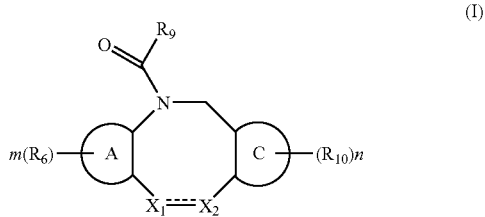

(I)

or an enantiomer, diastereomer, tautomer or pharmaceutically acceptable salt thereof, wherein the symbols have the following meanings and are, for each occurrence, independently selected:

x$_1$----x$_2$ is —CR$_1$=CR$_3$— or —CR$_1$R2—CR$_3$R$_4$—;

A ring and C ring are each independently phenyl or 5-6 membered unsaturated heterocyclic ring having one or two nitrogen heteroatoms, provided that at least one of said A ring and C ring is said 5-6 membered unsaturated heterocyclic ring;

R$_2$, R$_4$, R$_6$ and R$_{10}$ are each independently hydrogen, halogen, cyano, nitro, alkyl or substituted alkyl, alkenyl or substituted alkenyl, alkynyl or substituted alkynyl, cycloalkyl or substituted cycloalkyl, cycloalkenyl or substituted cycloalkenyl, heterocycle or substituted heterocycle, aryl or substituted aryl, OR$_a$, SR$_a$, S(=O) R$_e$, S(=O)$_2$R$_e$, S(=O)$_2$OR$_e$, NR$_b$R$_c$, NR$_b$S(=O)$_2$R$_e$, S(=O)$_2$NR$_b$R$_c$, C(=O)OR$_e$, C(=O)R$_a$, C(=O)NR$_b$R$_c$, OC(=O)R$_a$, OC(=O)NR$_b$R$_c$, NR$_b$C(=O)OR$_e$, NR$_d$C(O)NR$_b$R$_c$, NR$_d$S(=O)$_2$NR$_b$R$_c$, or NR$_b$C(=O)R$_a$, wherein: R$_2$ and R$_4$ together may optionally form a 3-7 membered optionally substituted carbocyclic ring or 3-7 membered optionally substituted heterocyclic ring;

R$_a$ is hydrogen, alkyl or substituted alkyl, alkenyl or substituted alkenyl, alkynyl or substituted alkynyl, cycloalkyl or substituted cycloalkyl, cycloalkenyl or substituted cycloalkenyl, heterocycle or substituted heterocycle, or aryl or substituted aryl;

R$_b$, R$_c$ and R$_d$ are independently hydrogen, alkyl or substituted alkyl, cycloalkyl or substituted cycloalkyl, heterocycle or substituted heterocycle, or aryl or substituted aryl, or said R$_b$ and R$_c$ together with the N to which they are bonded optionally form a heterocycle or substituted heterocycle;

R$_e$ is alkyl or substituted alkyl, alkenyl or substituted alkenyl, alkynyl or substituted alkynyl, cycloalkyl or substituted cycloalkyl, cycloalkenyl or substituted cycloalkenyl, heterocycle or substituted heterocycle, or aryl or substituted aryl;

R$_1$ and R$_3$ are each independently hydrogen, cyano, nitro, alkyl or substituted alkyl, alkenyl or substituted alkenyl, alkynyl or substituted alkynyl, cycloalkyl or substituted cycloalkyl, heterocycle or substituted heterocycle, aryl or substituted aryl, OR$_a$, SR$_a$, S(=O)R$_e$, S(=O)$_2$R$_e$, C(=O)OR$_e$, C(=O)R$_a$, NR$_b$R$_c$, NR$_b$C(=O)R$_a$, NR$_b$C(=O)OR$_e$, C(=O)NR$_b$R$_c$, OC(=O)R$_a$, or OC(=O)NR$_b$R$_c$, wherein R$_1$ and R$_3$ together may optionally form a 3-7 membered optionally substituted carbocyclic ring or 3-7 membered optionally substituted heterocyclic ring;

R$_9$ is H, alkyl or substituted alkyl, cycloalkyl or substituted cycloalkyl, cycloalkenyl or substituted cycloalkenyl, heterocycle or substituted heterocycle, aryl or substituted aryl, OR$_e$, or NR$_b$R$_c$;

m is 2, 3, or 4; and n is 2, 3, or 4.

2. The compound of claim 1, wherein:

A ring and C ring are each independently phenyl or 6-membered unsaturated heteroaryl ring having one or two nitrogen heteroatoms, provided that at least one of said A ring and said C ring is said 6-membered unsaturated heteroaryl ring; and R$_9$ is H, alkyl or substituted alkyl, or cycloalkyl or substituted cycloalkyl.

3. The compound of claim 1, wherein:

R$_6$ and R$_{10}$ are each independently hydrogen, halogen, cyano, nitro, alkyl or substituted alkyl, alkenyl or substituted alkenyl, alkynyl or substituted alkynyl, cycloalkyl or substituted cycloalkyl, heterocycle or substituted heterocycle, aryl or substituted aryl, OR$_a$, SR$_a$, S(=O)R$_e$, S(=O)$_2$R$_e$, S(=O)$_2$OR$_e$, NR$_b$R$_c$, NR$_b$S(=O)$_2$R$_e$, S(=O)$_2$NR$_b$R$_c$, C(=O)OR$_e$, C(=O)R$_a$, C(=O)NR$_b$R$_c$, OC(=O)R$_a$, OC(O)NR$_b$R$_c$, NR$_b$C(=O)OR$_e$, NR$_d$C(=O)NR$_b$R$_c$, NR$_d$S(=O)$_2$NR$_b$R$_c$, or NR$_b$C(=O)R$_a$;

R$_2$ and R$_4$ are each independently hydrogen, cyano, alkyl or substituted alkyl, cycloalkyl or substituted cycloalkyl, heterocycle or substituted heterocycle, aryl or substituted aryl, OR$_a$, SR$_a$, S(=O)R$_e$, S(=O)$_2$R$_e$, NR$_b$R$_c$, NR$_b$S(=O)$_2$R$_e$, S(=O)$_2$NR$_b$R$_c$, C(=O)OR$_e$, C(=O)R$_a$, C(=O)NR$_b$R$_c$, OC(=O)R$_a$, OC(=O)NR$_b$ R$_c$, NR$_b$C(=O)OR$_e$, NR$_d$C(=O)NR$_b$R$_c$, NR$_d$S(=O)$_2$ NR$_b$R$_c$, or NR$_b$C(=O)R$_a$, wherein R$_2$ and R$_4$ together may optionally form a 3-6 membered optionally substituted carbocyclic ring or 3-6 membered optionally substituted heterocyclic ring;

R$_1$ and R$_3$ are each independently hydrogen, cyano, alkyl or substituted alkyl, alkenyl or substituted alkenyl, alkynyl or substituted alkynyl, cycloalkyl or substituted cycloalkyl, heterocycle or substituted heterocycle, aryl or substituted aryl, OR$_a$, SR$_a$, S(=O)R$_e$, S(=O)$_2$R$_e$, C(=O)OR$_e$, C(=O)R$_a$, NR$_b$R$_c$, NR$_b$C(=O)R$_a$, C(=O)NR$_b$R$_c$, OC(=O)R$_a$, or OC(=O)NR$_b$R$_c$, wherein R$_1$ and R$_3$ together may optionally form a 3-6 membered optionally substituted carbocyclic ring or 3-6 membered optionally substituted heterocyclic ring; and R$_9$ is H, C$_1$-C$_4$ alkyl or substituted C$_1$-C$_4$ alkyl, or cycloalkyl or substituted cycloalkyl.

4. The compound of claim 1, wherein x$_1$----x$_2$ is —CR$_1$=CR$_3$—.

5. The compound of claim 4, wherein R$_9$ is H, methyl, CF$_3$, ethyl, isopropyl, or cyclopropyl.

6. The compound of claim 5, wherein R$_1$, R$_2$, R$_3$ and R$_4$ are each independently hydrogen.

7. The compound of claim 6, wherein R$_6$ is hydrogen, halogen, cyano, nitro, SMe, S(=O)$_2$Me, or OMe.

8. The compound of claim 1, wherein: x$_1$----x$_2$ is —CR$_1$R$_2$—CR$_3$R$_4$—;

A ring and C ring are each independently phenyl or 6-membered unsaturated heteroaryl ring having one or two nitrogen heteroatoms, provided that at least one of said A ring and said C ring is said 6-membered unsaturated heteroaryl ring;

R$_6$ and R$_{10}$ are each independently hydrogen, halogen, cyano, nitro, alkyl or substituted alkyl, alkenyl or substituted alkenyl, alkynyl or substituted alkynyl, cycloalkyl or substituted cycloalkyl, heterocycle or substituted heterocycle, aryl or substituted aryl, OR$_a$, SR$_a$, S(=O)R$_e$, S(=O)$_2$R$_e$, S(=O)$_2$OR$_e$, NR$_b$R$_c$, NR$_b$S(=O)$_2$R$_e$, S(=O)$_2$NR$_b$R$_c$, C(=O)OR$_e$, C(=O)R$_a$, C(=O)NR$_b$R$_c$, OC(=O)R$_a$, OC(=O)NR$_b$R$_c$, NR$_b$C(=O)OR$_e$, NR$_d$C(=O)NR$_b$R$_c$, NR$_d$S(=O)$_2$NR$_b$R$_c$, or NR$_b$C(=O)R$_a$;

R$_2$ and R$_4$ are each independently hydrogen, cyano, alkyl or substituted alkyl, cycloalkyl or substituted cycloalkyl, heterocycle or substituted heterocycle, aryl or substituted aryl, OR$_a$, SR$_a$, S(=O)R$_e$, S(=O)$_2$R$_e$, NR$_b$R$_c$, NR$_b$S(=O)$_2$R$_e$, S(=O)$_2$NR$_b$R$_c$, C(=O)OR$_e$, C(=O)R$_a$, C(=O)NR$_b$R$_c$, OC(=O)R$_a$, OC(=O)NR$_b$R$_c$, NR$_b$C(=O)OR$_e$, NR$_d$C(=O)NR$_b$R$_c$, NR$_d$S(=O)$_2$NR$_b$R$_c$, or NR$_b$C(=O)R$_a$, wherein R$_2$ and R$_4$ together may optionally form a 3-6 membered optionally substituted carbocyclic ring or 3-6 membered optionally substituted heterocyclic ring;

R$_1$ and R$_3$ are each independently hydrogen, cyano, alkyl or substituted alkyl, alkenyl or substituted alkenyl, alkynyl or substituted alkynyl, cycloalkyl or substituted cycloalkyl, heterocycle or substituted heterocycle, aryl or substituted aryl, OR$_a$, SR$_a$, S(=O)R$_e$, S(=O)$_2$R$_e$, C(=O)OR$_e$, C(=O)R$_a$, NR$_b$R$_c$, NR$_b$C(=O)R$_a$, C(=O)NR$_b$R$_c$, OC(=O)R$_a$, or OC(=O)NR$_b$R$_c$;

R$_9$ is H, C$_1$-C$_4$ alkyl or substituted C$_1$-C$_4$ alkyl, or cycloalkyl or substituted cycloalkyl.

9. The compound of claim 8, wherein R$_9$ is H, methyl, CF$_3$, ethyl, isopropyl, or cyclopropyl.

10. The compound of claim 9, wherein R$_1$, R$_2$, R$_3$ and R$_4$ are each independently hydrogen.

11. The compound of claim 10, wherein R$_6$ is hydrogen, halogen, cyano, nitro, —SMe, —S(=O)$_2$Me, or —OMe.

12. The compound of claim 1, wherein:

A ring and C ring are each independently phenyl, pyridinyl, or pyrimidinyl, provided that at least one of said A ring and said C ring is pyridinyl or pyrimidinyl;

R$_6$ and R$_{10}$ are each independently hydrogen, cyano, nitro, alkyl or substituted alkyl, alkenyl or substituted alkenyl, alkynyl or substituted alkynyl, cycloalkyl or substituted cycloalkyl, heterocycle or substituted heterocycle, aryl or substituted aryl, OR$_a$, SR$_a$, S(=O)R$_e$, S(=O)$_2$R$_e$, S(=O)$_2$OR$_e$, NR$_b$R$_c$, NR$_b$S(=O)$_2$R$_e$, S(=O)$_2$NR$_b$R$_c$, C(=O)OR$_e$, C(=O)R$_a$, C(=O)NR$_b$R$_c$, OC(=O)R$_a$, OC(=O)NR$_b$R$_c$, NR$_b$C(=O)OR$_e$, NR$_d$C(=O)NR$_b$R$_c$, NR$_d$S(=O)$_2$NR$_b$R$_c$, or NR$_b$C(=O)R$_a$;

R$_2$ and R$_4$ are each independently hydrogen, cyano, alkyl or substituted alkyl, cycloalkyl or substituted cycloalkyl, heterocycle or substituted heterocycle, aryl or substituted aryl, OR$_a$, SR$_a$, S(=O)R$_e$, S(=O)$_2$R$_e$, NR$_b$R$_c$, NR$_b$S(=O)$_2$R$_e$, S(=O)$_2$NR$_b$R$_c$, C(=O)OR$_e$, C(=O)R$_a$, C(=O)NR$_b$R$_c$, OC(=O)R$_a$, OC(=O)NR$_b$R$_c$, NR$_b$C(=O)OR$_e$, NR$_d$C(=O)NR$_b$R$_c$, NR$_d$S(=O)$_2$NR$_b$R$_c$, NR$_b$C(=O)R$_a$, wherein R$_2$ and R$_4$ together may optionally form a 3-6 membered optionally substituted carbocyclic ring or 3-6 membered optionally substituted heterocyclic ring;

R$_1$ and R$_3$ are each independently hydrogen, cyano, alkyl or substituted alkyl, alkenyl or substituted alkenyl, alkynyl or substituted alkynyl, cycloalkyl or substituted cycloalkyl, heterocycle or substituted heterocycle, aryl or substituted aryl, OR$_a$, SR$_a$, S(=O)R$_e$, S(=O)$_2$R$_e$, C(=O)OR$_e$, C(=O)R$_a$, NR$_b$R$_c$, NR$_b$C(=O)R$_a$, C(=O)NR$_b$R$_c$, OC(=O)R$_a$, or OC(=O)NR$_b$R$_c$, wherein R$_1$ and R$_3$ together may optionally form a 3-6 membered optionally substituted carbocyclic ring or 3-6 membered optionally substituted heterocyclic ring;

R$_9$ is H, C$_1$-C$_4$ alkyl or substituted C$_1$-C$_4$ alkyl, or cycloalkyl or substituted cycloalkyl.

13. The compound of claim 12, wherein R$_9$ is H, methyl, CF$_3$, ethyl, isopropyl, or cyclopropyl.

14. The compound of claim 13, wherein R$_1$, R$_2$, R$_3$ and R$_4$ are each independently hydrogen.

15. The compound of claim 14, wherein R$_6$ is hydrogen, halogen, cyano, nitro, SMe, S(=O)$_2$Me, or OMe.

16. The compound of claim 1 having the following structure Ia,

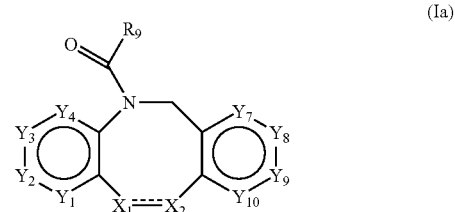

(Ia)

wherein:
Y$_1$, Y$_4$, Y$_7$ and Y$_{10}$ are each independently CH or N;
Y$_2$ is CR$_7$ or N;
Y$_3$ is CR$_8$ or N;
Y$_8$ is CR$_{10}$ or N;
Y$_9$ is CR$_{11}$ or N;
provided that at least one of Y$_1$, Y$_2$, Y$_3$, Y$_4$, Y$_7$, Y$_8$, Y$_9$ and Y$_{10}$ is N;

$R_7$, $R_8$, $R_{10}$ and $R_{11}$ are each independently hydrogen, halogen, cyano, nitro, alkyl or substituted alkyl, alkenyl or substituted alkenyl, alkynyl or substituted alkynyl, cycloalkyl or substituted cycloalkyl, heterocycle or substituted heterocycle, aryl or substituted aryl, $OR_a$, $SR_a$, $S(=O)R_e$, $S(=O)_2R_e$, $S(=O)_2OR_e$, $NR_bR_c$, $NR_bS(=O)_2R_e$, $S(=O)_2NR_bR_c$, $C(=O)OR_e$, $C(=O)R_a$, $C(=O)NR_bR_c$, $OC(=O)R_a$, $OC(=O)NR_bR_c$, $NR_bC(=O)OR_e$, $NR_dC(=O)NR_bR_c$, $NR_dS(=O)_2NR_bR_c$, or $NR_bC(=O)R_a$;

$R_2$ and $R_4$ are each independently hydrogen, cyano, alkyl or substituted alkyl, cycloalkyl or substituted cycloalkyl, heterocycle or substituted heterocycle, aryl or substituted aryl, $OR_a$, $SR_a$, $S(=O)R_e$, $S(=O)_2R_e$, $NR_bR_c$, $NR_bS(=O)_2R_e$, $S(=O)_2NR_bR_c$, $C(=O)OR_e$, $C(=O)R_a$, $C(=O)NR_bR_c$, $OC(=O)R_a$, $OC(=O)NR_bR_c$, $NR_bC(=O)OR_e$, $NR_dC(=O)NR_bR_c$, $NR_dS(=O)_2NR_bR_c$, or $NR_bC(=O)R_a$, wherein $R_2$ and $R_4$ together may optionally form a 3-6 membered optionally substituted carbocyclic ring or 3-6 membered optionally substituted heterocyclic ring;

$R_1$ and $R_3$ are each independently hydrogen, cyano, alkyl or substituted alkyl, alkenyl or substituted alkenyl, alkynyl or substituted alkynyl, cycloalkyl or substituted cycloalkyl, heterocycle or substituted heterocycle, aryl or substituted aryl, $OR_a$, $SR_a$, $S(=O)R_e$, $S(=O)_2R_e$, $C(=O)OR_e$, $C(=O)R_a$, $NR_bR_c$, $NR_bC(=O)R_a$, $C(=O)NR_bR_c$, $OC(=O)R_a$, or $OC(=O)NR_bR_c$, wherein $R_1$ and $R_3$ together may optionally form a 3-6 membered optionally substituted carbocyclic ring or 3-6 membered optionally substituted heterocyclic ring; and $R_9$ is H, $C_1$-$C_4$ alkyl or substituted $C_1$-$C_4$ alkyl, or cycloalkyl or substituted cycloalkyl.

17. The compound of claim 16, wherein $R_9$ is H, methyl, $CF_3$, ethyl, isopropyl, or cyclopropyl.

18. The compound of claim 17, wherein $R_1$, $R_2$, $R_3$ and $R_4$ are each independently hydrogen.

19. The compound of claim 18, wherein $R_7$ and $R_8$ are each independently hydrogen, halogen, cyano, nitro, SMe, $S(=O)_2Me$, or OMe.

20. The compound of claim 1 having the following structure Ib,

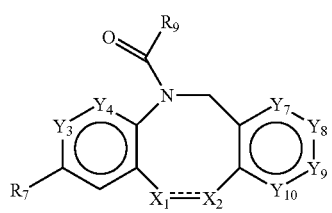

(Ib)

$Y_4$, $Y_7$ and $Y_{10}$ are each independently CH or N;
$Y_3$ is $CR_8$ or N;
$Y_8$ is $CR_{10}$ or N;
$Y_9$ is $CR_{11}$ or N;
provided that the total number of N atoms among $Y_3$, $Y_4$, $Y_7$, $Y_8$, $Y_9$ and $Y_{10}$ is one, two, or three;

$R_7$, $R_8$, $R_{10}$ and $R_{11}$ are each independently hydrogen, halogen, cyano, alkyl or substituted alkyl, cycloalkyl or substituted cycloalkyl, heterocycle or substituted heterocycle, aryl or substituted aryl, $OR_e$, $SR_e$, $S(=O)R_e$, $S(=O)_2R_e$, $NR_bR_c$, $C(=O)OR_e$, $C(=O)R_a$, $C(=O)NR_bR_c$, $NR_bC(=O)OR_e$, $NR_bC(=O)R_a$;

$R_2$ and $R_4$ are each independently hydrogen, $C_1$-$C_4$ alkyl or substituted $C_1$-$C_4$ alkyl, or $R_2$ and $R_4$ together may optionally form a 3-6 membered optionally substituted carbocyclic ring or 3-6 membered optionally substituted heterocyclic ring;

$R_1$ and $R_3$ are each independently hydrogen, cyano, nitro, alkyl or substituted alkyl, alkenyl or substituted alkenyl, alkynyl or substituted alkynyl, cycloalkyl or substituted cycloalkyl, heterocycle or substituted heterocycle, aryl or substituted aryl, $OR_a$, $SR_a$, $S(=O)R_e$, $S(=O)_2R_e$, $C(=O)OR_e$, $C(=O)R_a$, $NR_bR_c$, $NR_bC(=O)R_a$, $C(=O)NR_bR_c$, $OC(=O)R_a$, or $OC(=O)NR_bR_c$, wherein $R_1$ and $R_3$ together may optionally form a 3-7 membered optionally substituted carbocyclic ring or 3-7 membered optionally substituted heterocyclic ring; and $R_9$ is H, $C_1$-$C_4$ alkyl or substituted $C_1$-$C_4$ alkyl, or cycloalkyl or substituted cycloalkyl.

21. The compound of claim 20, wherein $R_9$ is H, methyl, $CF_3$, ethyl, isopropyl, or cyclopropyl.

22. The compound of claim 21, wherein $R_1$, $R_2$, $R_3$ and $R_4$ are each independently hydrogen.

23. The compound of claim 22, wherein $R_7$ and $R_8$ are each independently hydrogen, halogen, cyano, nitro, SMe, $S(=O)_2Me$, or OMe.

24. A pharmaceutical composition comprising at least one compound according to claim 1 and a pharmaceutically-acceptable carrier or diluent.

25. A pharmaceutical composition of claim 24, further comprising at least one other anti-cancer agent or cytotoxic agent.

26. The pharmaceutical composition of claim 25, wherein said anti-cancer or cytotoxic agent is selected from the group consisting of tamoxifen, toremifene, raloxifene, droloxifene, iodoxifene, megestrol acetate, anastrozole, letrozole, borazole, exemestane, flutamide, nilutamide, bicalutamide, cyproterone acetate, gosereline acetate, leuprolide, finasteride, metalloproteinase inhibitors, inhibitors of urokinase plasminogen activator receptor function, growth factor antibodies, growth factor receptor antibodies, bevacizumab, cetuximab, tyrosine kinase inhibitors, serine/threonine kinase inhibitors, methotrexate, 5-fluorouracil, purine and adenosine analogues, cytosine arabinoside, doxorubicin, daunomycin, epirubicin, idarubicin, mitomycin-C, dactinomycin, mithramycin, cisplatin, carboplatin, nitrogen mustard, melphalan, chlorambucil, busulphan, cyclophosphamide, ifosfamide, nitrosoureas, thiotepa, vincristine, vinorelbine, vinblastine, vinflunine, paclitaxel, docetaxel, epothilone analogs, discodermolide analogs, eleutherobin analogs, etoposide, teniposide, amsacrine, topotecan, flavopyridols, proteasome inhibitors including bortezomib and biological response modifiers, androgen receptor antagonists, LH/RH antagonists, taxane analogues, and estrogen receptor antagonists.

27. A method of inhibiting the activity of 17β-hydroxysteroid dehydrogenase type 3 enzyme which comprises administering to a mammalian species in need thereof an effective amount of at least one compound according to claim 1.

28. A method for treating prostate cancer comprising administering a mammalian species in need thereof a therapeutically effective amount of at least one compound according to claim 1.

29. The method of claim 28, further comprising administering to a mammalian species in need thereof, a therapeutically effective amount of at least one other anti-cancer or cytotoxic agent in combination with at least one compound according to claim 1.

30. The method of claim 29, wherein said anti-cancer or cytotoxic agent is selected from the group consisting of tamoxifen, toremifene, raloxifene, droloxifene, iodoxifene, megestrol acetate, anastrozole, letrozole, borazole, exemestane, flutamide, nilutamide, bicalutamide, cyproterone acetate, gosereline acetate, leuprolide, finasteride, metalloproteinase inhibitors, inhibitors of urokinase plasminogen activator receptor function, growth factor antibodies, growth factor receptor antibodies, bevacizumab, cetuximab, tyrosine kinase inhibitors, serine/threonine kinase inhibitors, methotrexate, 5-fluorouracil, purine and adenosine analogues, cytosine arabinoside, doxorubicin, daunomycin, epirubicin, idarubicin, mitomycin-C, dactinomycin, mithramycin, cisplatin, carboplatin, nitrogen mustard, melphalan, chlorambucil, busulphan, cyclophosphamide, ifosfamide, nitrosoureas, thiotepa, vincristine, vinorelbine, vinblastine, vinflunine, paclitaxel, docetaxel, taxane analogues, epothilone analogs, discodermolide analogs, eleutherobin analogs, etoposide, teniposide, amsacrine, topotecan, flavopyridols, proteasome inhibitors, androgen receptor antagonists, LH/RH antagonists, and estrogen receptor antagonists.

\* \* \* \* \*

UNITED STATES PATENT AND TRADEMARK OFFICE
CERTIFICATE OF CORRECTION

PATENT NO. : 7,378,426 B2
APPLICATION NO. : 11/066407
DATED : May 27, 2008
INVENTOR(S) : Gavai et al.

It is certified that error appears in the above-identified patent and that said Letters Patent is hereby corrected as shown below:

In Column 83, Line 56:

"$X_1=X_2$ is -$CR_1$=$CR_3$- or -$CR_1R2$-$CR_3R_4$-;"

should read -- $X_1=X_2$ is -$CR_1$=$CR_3$- or -$CR_1R_2$-$CR_3R_4$-; --

Signed and Sealed this

Twenty-third Day of September, 2008

JON W. DUDAS
*Director of the United States Patent and Trademark Office*